US012685461B2

(12) United States Patent
Tshitoyan et al.

(10) Patent No.: US 12,685,461 B2
(45) Date of Patent: Jul. 21, 2026

(54) WEARABLE DEVICE USING SPATIALLY SCANNED STIMULATED RAMAN SPECTROSCOPY FOR RELIABLE DETECTION OF BLOOD ANALYTE CONCENTRATIONS

(71) Applicant: Google LLC, Mountain View, CA (US)

(72) Inventors: Vahe Tshitoyan, Pleasanton, CA (US); Cheongyuen William Tsang, Union City, CA (US); Rafeed A. Chaudhury, San Francisco, CA (US); Kelly Elizabeth Dobson, Mountain View, CA (US)

(73) Assignee: GOOGLE LLC, Mountain View, CA (US)

( * ) Notice: Subject to any disclaimer, the term of this patent is extended or adjusted under 35 U.S.C. 154(b) by 358 days.

(21) Appl. No.: 18/255,747

(22) PCT Filed: Jul. 29, 2022

(86) PCT No.: PCT/US2022/038922
§ 371 (c)(1),
(2) Date: Jun. 2, 2023

(87) PCT Pub. No.: WO2024/025564
PCT Pub. Date: Feb. 1, 2024

(65) Prior Publication Data
US 2024/0374178 A1 Nov. 14, 2024

(51) Int. Cl.
*A61B 5/1455* (2006.01)
*A61B 5/145* (2006.01)
(Continued)

(52) U.S. Cl.
CPC ........ *A61B 5/14546* (2013.01); *A61B 5/1455* (2013.01); *H01S 5/4031* (2013.01); *H01S 5/423* (2013.01)

(58) Field of Classification Search
CPC .......................... A61B 5/1455; A61B 5/14532
See application file for complete search history.

(56) References Cited

U.S. PATENT DOCUMENTS

2002/0169368 A1 11/2002 Hwang et al.
2013/0216114 A1 8/2013 Courtney et al.
(Continued)

FOREIGN PATENT DOCUMENTS

CN 103096791 5/2013
CN 109561931 4/2019
(Continued)

OTHER PUBLICATIONS

International Search Report for PCT/US2022/038922, mailed on Mar. 3, 2023, 5 pages.
(Continued)

*Primary Examiner* — Marjan Fardanesh
(74) *Attorney, Agent, or Firm* — DORITY & MANNING P.A.

(57) ABSTRACT

The present disclosure provides methods, systems, and devices for non-invasively measuring a level of an analyte in a user using Stimulated Raman Scattering. A device can include a Raman pump source that emits pump light toward a tissue at a pump wavelength and a Stokes source that emits Stokes light toward the tissue at one or more Stokes wavelengths. The device can further include one or more mirrors and lenses. The device can further include a beam controller that controls the one or more mirrors and the one or more lenses to target the pump light emitted by the Raman pump source and the Stokes light emitted by the Stokes source at an optimal target location. The device can further include a photodetector that measures light that emanates from the tissue. The device can further include a processor that estimates the level of the analyte in the user.

17 Claims, 35 Drawing Sheets

(51) Int. Cl.
  *H01S 5/40* (2006.01)
  *H01S 5/42* (2006.01)

(56) References Cited

U.S. PATENT DOCUMENTS

| | | |
|---|---|---|
| 2016/0157757 A1 | 6/2016 | Murthy |
| 2018/0132766 A1 | 5/2018 | Lee et al. |
| 2021/0025758 A1 | 1/2021 | Katz |
| 2024/0390055 A1 | 11/2024 | Pearson et al. |

FOREIGN PATENT DOCUMENTS

| | | |
|---|---|---|
| CN | 208872669 | 5/2019 |
| KR | 2022/0037547 | 3/2022 |
| WO | WO 2021/116766 A1 | 6/2021 |

OTHER PUBLICATIONS

International Preliminary Report on Patentability for Application No. PCT/US2022/038922, mailed Feb. 13, 2025, 7 pages.
Chinese Search Report Corresponding to Application No. 2022800088161 on Mar. 9, 2026.

RAMAN SCATTERED LIGHT 0.000001%

RAYLEIGH SCATTERED LIGHT

BREAKDOWN OF SCATTERED LIGHT

SPONTANEOUS RAMAN SPECTRUM (ETHANOL)

RAMAN INTENSITY

RAYLEIGH SCATTERED LIGHT

STOKES RAMAN SCATTERED LIGHT

ANTI-STOKES RAMAN SCATTERED LIGHT

| WAVENUMBER (cm⁻¹) | -1000 | -800 | -600 | -400 | -200 | 0 | 200 | 400 | 600 | 800 | 1000 |
|---|---|---|---|---|---|---|---|---|---|---|---|
| WAVENUMBER (nm) | 505 | 510 | 516 | 521 | 526 | 532 | 538 | 544 | 550 | 556 | 562 |

- RAYLEIGH IN CENTER (1,000,000X > STOKES)
- DISCRETE PEAKS PROVIDE MEASUREMENT SPECIFICITY

SPONTANEOUS

STIMULATED

FIBER WITH PUMP 112 AND
STOKES SOURCES 116

OPTICAL FILTER
1304

PUMP

STOKES

10 μm

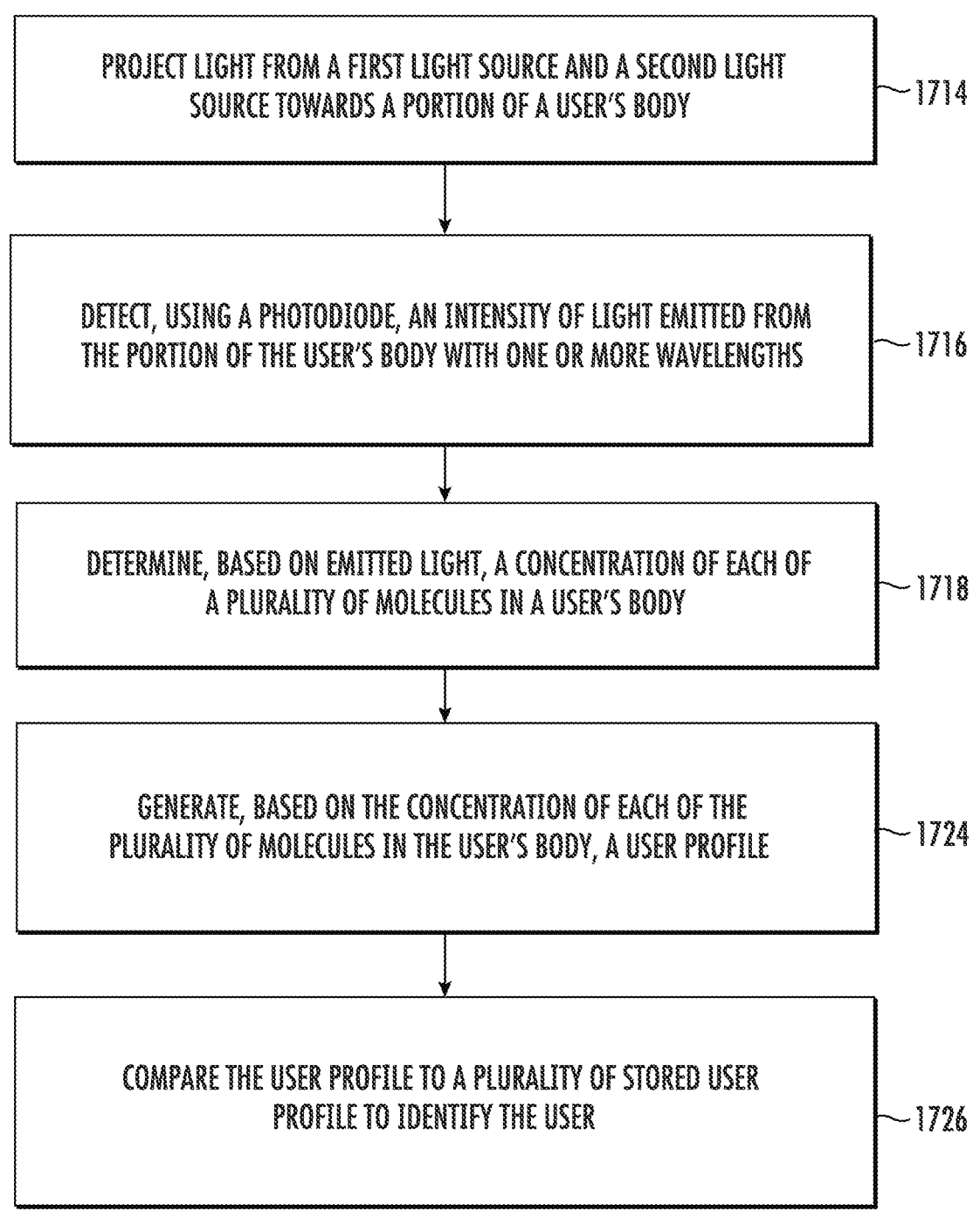

PROJECT LIGHT FROM A FIRST LIGHT SOURCE AND A SECOND LIGHT SOURCE TOWARDS A PORTION OF A USER'S BODY ~1714

DETECT, USING A PHOTODIODE, AN INTENSITY OF LIGHT EMITTED FROM THE PORTION OF THE USER'S BODY WITH ONE OR MORE WAVELENGTHS ~1716

DETERMINE, BASED ON EMITTED LIGHT, A CONCENTRATION OF EACH OF A PLURALITY OF MOLECULES IN A USER'S BODY ~1718

GENERATE, BASED ON THE CONCENTRATION OF EACH OF THE PLURALITY OF MOLECULES IN THE USER'S BODY, A USER PROFILE ~1724

COMPARE THE USER PROFILE TO A PLURALITY OF STORED USER PROFILE TO IDENTIFY THE USER ~1726

FIG. 17

OUTPUT DATA

1844

DATA ANALYSIS MODEL
1810

INPUT DATA

1842

EMIT, USING A PUMP LASER, PUMP LIGHT INTO A SKIN SURFACE OF THE PATIENT — 1812

EMIT, USING A STOKES LASER, STOKES LIGHT INTO THE SKIN SURFACE — 1814

MEASURE, USING A PHOTODETECTOR, LIGHT THAT IS EMANATING BACK OUT THE SKIN SURFACE — 1816

PROCESS THE MEASURED LIGHT TO PROVIDE AN ESTIMATED GLUCOSE LEVEL OF THE PATIENT — 1818

2400 ⟍

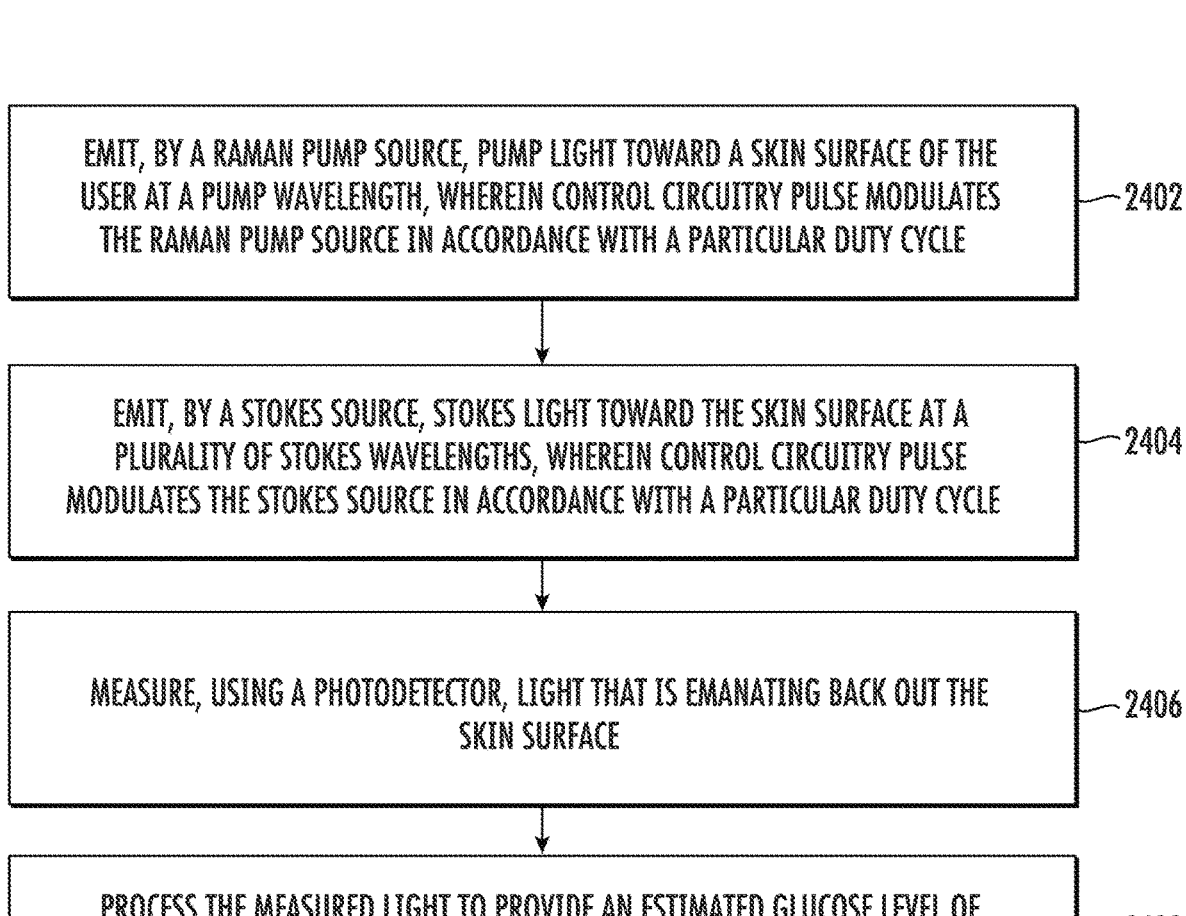

EMIT, BY A RAMAN PUMP SOURCE, PUMP LIGHT TOWARD A SKIN SURFACE OF THE USER AT A PUMP WAVELENGTH, WHEREIN CONTROL CIRCUITRY PULSE MODULATES THE RAMAN PUMP SOURCE IN ACCORDANCE WITH A PARTICULAR DUTY CYCLE ⟍ 2402

EMIT, BY A STOKES SOURCE, STOKES LIGHT TOWARD THE SKIN SURFACE AT A PLURALITY OF STOKES WAVELENGTHS, WHEREIN CONTROL CIRCUITRY PULSE MODULATES THE STOKES SOURCE IN ACCORDANCE WITH A PARTICULAR DUTY CYCLE ⟍ 2404

MEASURE, USING A PHOTODETECTOR, LIGHT THAT IS EMANATING BACK OUT THE SKIN SURFACE ⟍ 2406

PROCESS THE MEASURED LIGHT TO PROVIDE AN ESTIMATED GLUCOSE LEVEL OF THE PATIENT ⟍ 2408

FIG. 25

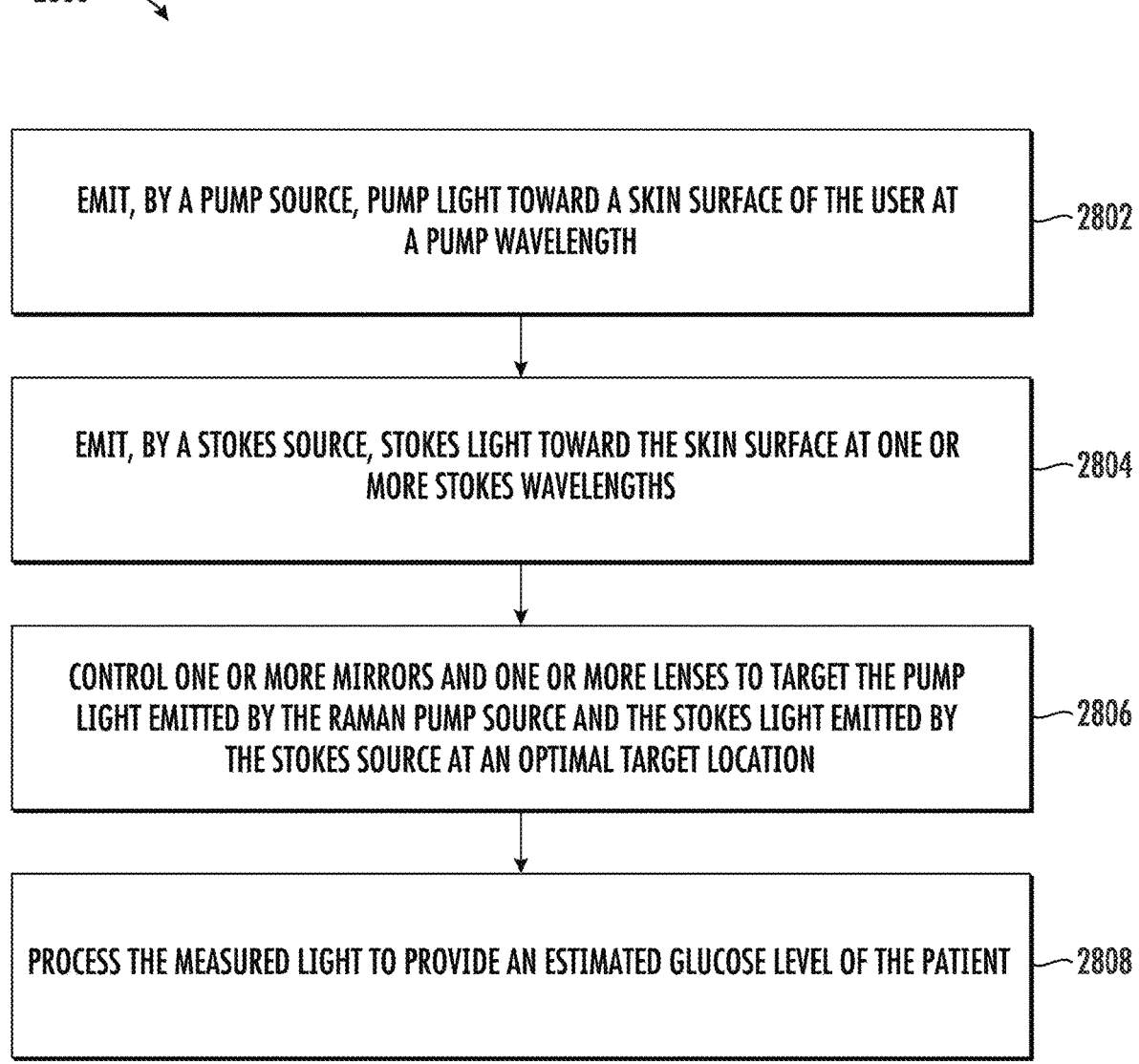

2800

EMIT, BY A PUMP SOURCE, PUMP LIGHT TOWARD A SKIN SURFACE OF THE USER AT A PUMP WAVELENGTH ⎯2802

EMIT, BY A STOKES SOURCE, STOKES LIGHT TOWARD THE SKIN SURFACE AT ONE OR MORE STOKES WAVELENGTHS ⎯2804

CONTROL ONE OR MORE MIRRORS AND ONE OR MORE LENSES TO TARGET THE PUMP LIGHT EMITTED BY THE RAMAN PUMP SOURCE AND THE STOKES LIGHT EMITTED BY THE STOKES SOURCE AT AN OPTIMAL TARGET LOCATION ⎯2806

PROCESS THE MEASURED LIGHT TO PROVIDE AN ESTIMATED GLUCOSE LEVEL OF THE PATIENT ⎯2808

FIG. 28

WEARABLE DEVICE USING SPATIALLY SCANNED STIMULATED RAMAN SPECTROSCOPY FOR RELIABLE DETECTION OF BLOOD ANALYTE CONCENTRATIONS

PRIORITY CLAIM

This application is based upon and claims the right of priority under 35 U.S.C. § 371 to International Application No. PCT/US2022/038922 filed on Jul. 29, 2022, which is incorporated by reference herein.

FIELD

The present disclosure relates generally to the non-invasive monitoring of molecules in a body of a user.

BACKGROUND

A number of human medical conditions exist that may result in a need to measure an amount of particular molecule present in an individual. For example, it is currently estimated that around 463 million adults have diabetes. For many of these individuals, periodic monitoring of the amount of glucose present in their bloodstream is a part of normal life in order to avoid serious medical complications. Traditionally, to measure the chemical makeup internal to a user's body, invasive measuring methods (e.g., such as sample tissue extraction or blood draw) have been used. Example techniques include finger-prick blood glucometry and transdermal continuous glucose monitoring (CGM). These systems are often painful and/or expensive to use. For users that have to repeatedly take such measurements, the pain and expense associated with glucose monitoring can significantly affect their quality of life.

SUMMARY

Aspects and advantages of embodiments of the present disclosure will be set forth in part in the following description, or may be learned from the description, or may be learned through practice of the embodiments.

One example embodiment includes a device for non-invasively measuring a level of an analyte in a user using Stimulated Raman Scattering. The device can include a Raman pump source that emits pump light toward a tissue of the user at a pump wavelength. The device further includes a Stokes source that emits Stokes light toward the tissue at one or more Stokes wavelengths. The device further includes one or more mirrors. The device further includes one or more lenses. The device further includes a beam controller that controls the one or more mirrors and the one or more lenses to target the pump light emitted by the Raman pump source and the Stokes light emitted by the Stokes source at an optimal target location. The device further includes a photodetector that measures light that emanates from the tissue. The device further includes a processor that processes the measured light to provide an estimated analyte level of the analyte in the user.

Another example aspect of the present disclosure is a computer-implemented method for non-invasively measuring a level of an analyte in a user using Stimulated Raman Scattering. The method comprises emitting, by a Raman pump source, pump light toward a tissue of the user at a pump wavelength. The method further comprises emitting, by a Stokes source, Stokes light toward the tissue at one or more Stokes wavelengths. The method further comprises controlling, by a beam controller, one or more mirrors and one or more lenses to target the pump light emitted by the Raman pump source and the Stokes light emitted by the Stokes source at an optimal target location. The method further comprises measuring, by a photodetector, light that emanates from the tissue. The method further comprises processing, by a processor, the measured light to provide an estimated analyte level of the analyte in the user.

Another example aspect of the present disclosure is an analyte estimation system. The system includes a Raman pump source that emits pump light toward a tissue of the user at a pump wavelength. The system further includes a Stokes source that emits Stokes light toward the tissue at one or more Stokes wavelengths. The system further includes one or more mirrors and one or more lenses. The system further includes a beam controller that controls the one or more mirrors and the one or more lenses to target the pump light emitted by the Raman pump source and the Stokes light emitted by the Stokes source at an optimal target location. The system further includes a photodetector that measures light that emanates from the tissue. The system further includes a processor that processes the measured light to provide an estimated analyte level of the analyte in the user.

Other example aspects of the present disclosure are directed to systems, apparatus, computer program products (such as tangible, non-transitory computer-readable media but also such as software which is downloadable over a communications network without necessarily being stored in non-transitory form), user interfaces, memory devices, and electronic devices for measuring stimulated Raman scattering using an embedded computing system.

These and other features, aspects and advantages of various embodiments will become better understood with reference to the following description and appended claims. The accompanying drawings, which are incorporated in and constitute a part of this specification, illustrate embodiments of the present disclosure and, together with the description, serve to explain the related principles.

BRIEF DESCRIPTION OF THE DRAWINGS

A detailed discussion of embodiments directed to one of ordinary skill in the art are set forth in the specification, which refers to the appended figures, in which:

FIG. 17 is a flowchart depicting an example process of detecting molecules within a target in accordance with example embodiments of the present disclosure;

FIG. 20 is a diagram of an analyte detection system that causes light from different sources to be collinear in accordance with example embodiments of the present disclosure;

FIG. 25 is a flowchart depicting an example process of detecting analytes within a target tissue in accordance with example embodiments of the present disclosure.

FIG. 28 is a flowchart depicting an example process of detecting analytes within a target tissue in accordance with example embodiments of the present disclosure.

DETAILED DESCRIPTION

Figure 1:
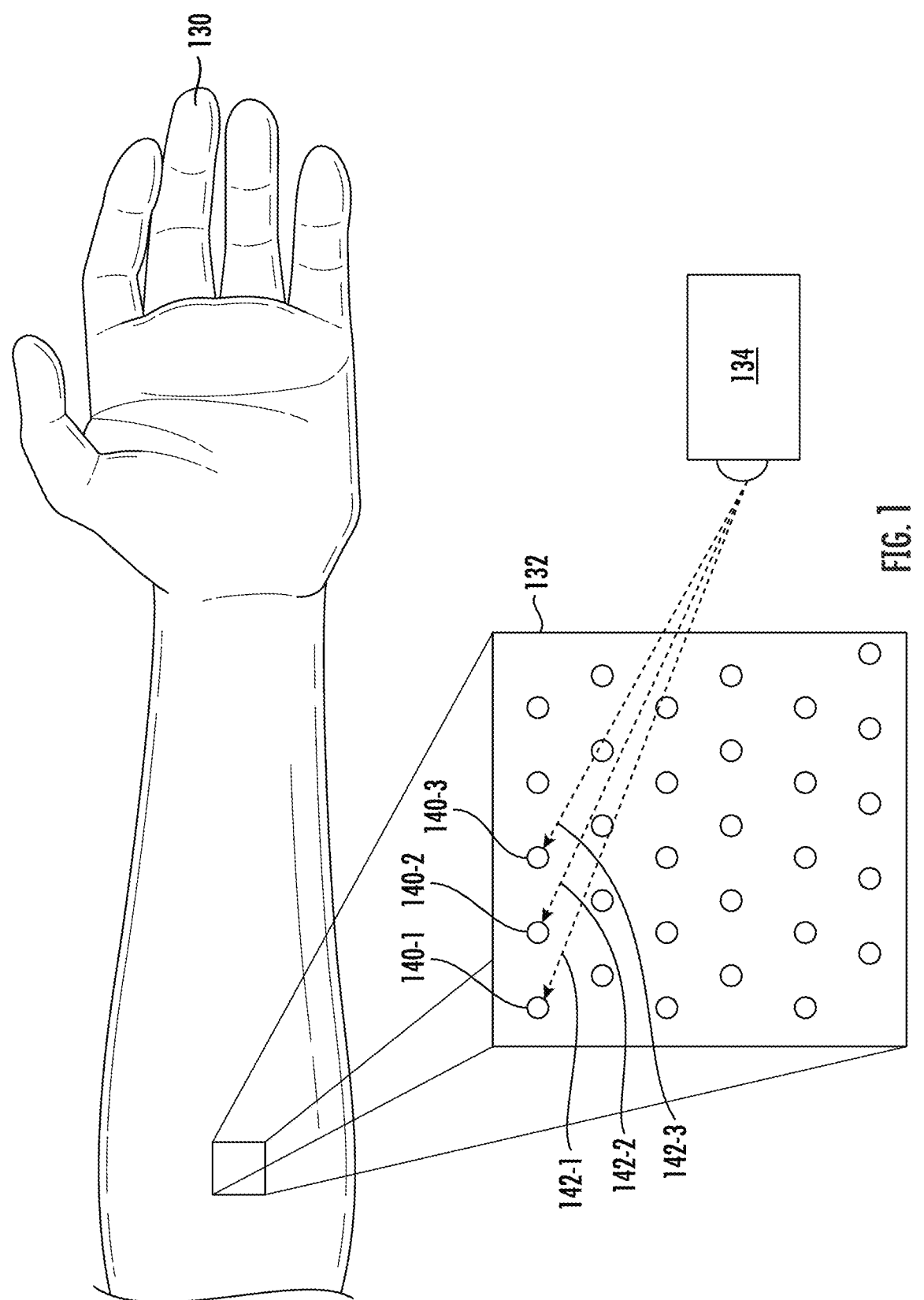
FIG. 1 illustrates an example analyte estimation system for scanning an area of the arm of a user non-invasively in accordance with example embodiments of the present disclosure.

Reference now will be made in detail to embodiments, one or more examples of which are illustrated in the drawings. Each example is provided by way of explanation of the embodiments, not limitation of the present disclosure. In fact, it will be apparent to those skilled in the art that various modifications and variations can be made to the embodiments without departing from the scope or spirit of the present disclosure. For instance, features illustrated or described as part of one embodiment can be used with another embodiment to yield a still further embodiment. Thus, it is intended that aspects of the present disclosure cover such modifications and variations.

Generally, the present disclosure is directed towards a system for improving the performance of an analyte measurement system that non-invasively monitors one or more analytes internal to the body of a user. For example, an analyte measurement system for monitoring analytes in accordance with example embodiments can estimate the amount of an analyte in a target material (e.g., the tissue of a user) using Raman spectroscopy, by projecting light into a target material and measuring the wavelengths and intensity of the light that is emitted out of the material. To ensure that the power density of the light is high enough to result in measurable Raman scattering, the area at which the projected light is targeted can be very small (e.g., a diameter around a micrometer). As a result, small variations in the specific area of the tissue that is targeted by the light sources can significantly affect the ability of the analyte measurement system to accurately measure the amount of analyte present because the type of tissue (also referred herein as the composition of tissue) can differ greatly. As a result, the analyte measurement system can identify an optimal target location within the tissue of a user and then control the targeting of the light sources (e.g., with one or more mirrors and one or more lenses) to focus on the optimal target location. Accurately targeting a portion of tissue within the skin of a user can result in improved accuracy and efficiency in measuring analytes within the target material.

Thus, an analyte measurement system can be improved by using one or more mirrors and one or more lenses to control the one or more beams projected by the pump light source and the one or more Stokes light source in such a way as to specifically target an optimal target location within the tissue of a user. To do so, the analyte measurement system can include a beam controller that controls the area targeted by the light sources (e.g., by controlling the one or more mirrors and the one or more lenses).

To identify the optimal target location within the tissue of the user, the analyte detection system can perform sparse sampling of the area of tissue that the analyte measurement system can access. For example, a target location may have a diameter of 1 micrometer in order to achieve a desired density of light. To identify an optimal target location, the system may sample 1 micrometer areas across a region spanning 200 micrometers by 200 micrometers in order to identify an optimal target location for measurement. An optimal target location can be a location of tissue that exhibits a measurement response that enables identification of a particular analyte. The various areas sampled within the sampling region can be compared to identify the area exhibiting the best response characteristics. In some examples, the optimal target location can be dependent on the specific analyte that the system seeks to detect. Thus, the system can store data that relates the optimal type of tissue for each potential analyte. For example, if the target analyte is glucose, the optimal type of tissue can be the interior of a blood vessel. The system may compare the measurement response of the different areas in a sampling region to identify an interior blood vessel region. In other examples, the optimal type of tissue can vary.

An optimal target location may be a location that provides an accurate measurement of the presence of a particular analyte. the system can store an identification of tissue types that result in the most accurate measurements of the presence of particular analytes in the user's tissue. This data can be stored in a database accessible to the analyte measurement system. The analyte measurement system can compare the data in the database to the types of tissue determined when the system performs sparse sampling. In some examples, factors other than tissue type can be used to determine the optimal target location. For example, the depth within the tissue of a particular location can be used in determining the optimal target location. For example, if two locations have the same tissue type, the analyte measurement system can select the location having less depth within the tissue of the user.

The sparse sampling can be accomplished by defining an area that can be targeted by the analyte measurement system and determining a plurality of points arranged in a three-dimensional grid to cover the area. The three-dimensional grid (or target sampling grid) can include points at different positions relative to the surface of the skin (along the x-axis and the y-axis) and at different depths within the skin (along the z-axis). For each respective point in the target sampling grid, the analyte detection system can, using the beam controller, project light at the respective point. The analyte detection system can measure the absorption of light at the respective point.

In some examples, size of the central grid can be determined by the characteristics of the lasers, the mirrors, and the lenses that can be controlled to target the laser. For example, the targeting sampling grid can be 200 micrometers by 200 micrometers. The analyte measurement system can space the sampling points out every five micrometers along the surface of the target sampling grid in two dimensions. In addition, the analyte measurement system can sample at different depths within the tissue. For example, the target sampling grid can include three depth layers, with each layer 5 micrometers deeper than the other, such that the first layer is on the surface, the second layer is 5 micrometers deep into the tissue, and the third is 10 micrometers deep into the tissue. Other dimensions of the target sampling grid and the depth of the target sampling can be used.

The absorption of different wavelengths of light can be used to determine the types of material in that issue that is being sampled. For example, different materials can absorb different wavelengths of light and can emit different wavelengths of light. The amount and intensity of light emitted from that issue can be measured and compared to the amount and intensity of light wavelengths transmitted into the light to determine the amount of different labs length that has been absorbed.

By comparing the absorption of different wavelengths and comparing it tissue type wavelength absorption data, the analyte measurement system can estimate the type of the tissue at that location. For example, the location can be one or more of: interstitial fluid, cells associated with the epidermis, cells associate with the dermis, fat cells, glands, nerve cells, blood vessels, follicles, and so on. The analyte estimation system can use the same light sources and photodetector to perform the sparse sampling as is used during analyte detection. However, the amount and intensity of light used can be reduced during the sparse sampling process. In this way, the analyte estimation system can use less power to quickly identify the type of tissue at a plurality of points within a particular area.

In some examples, the type of tissue at a particular location can affect the accuracy of the analyte measurement system. Thus, the analyte measurement system can select a specific location based on the sparse scanning that has a tissue type that is most conducive to accurately measuring the analyte of interest. The selected location can be stored as the optimal target location for measuring the analyte. The analyte measurement system can, using the beam controller, focus the beams from one or more light sources (e.g., the Raman pump source and one or more Stokes sources) at the optimal target location. A photodetector can measure the light emitted from the target location. Based on the emitted light, the analyte measurement system can determine the amount of a particular analyte in the body of the user.

More generally, Raman spectroscopy uses Raman scattering to determine whether an analyte is present in a particular target material (e.g., the tissue of a user). Raman scattering is an optical process where excitation light can be projected into a target sample by a light source (e.g., a pump laser). Molecules within the target sample can be excited to a higher energy state by the incoming excitation light. The molecule that has been excited can emit a photon, thus lowering the energy of the molecule to a lower energy level. In some examples, the higher energy state can be a virtual excited state such that the molecule is never actually excited to that state. Instead, both the excitation and the relaxation (when the photon is emitted) occur simultaneously via the virtual state.

The specific wavelengths present in photons generated by Raman scattering can be determined by the vibrational modes of the chemical bonds of the molecule that was excited by the excitation light and the wavelength of the incoming light. A system that uses Raman scattering to determine the presence of an analyte can implement either spontaneous Raman scattering or stimulated Raman scatter-
ing. It should be noted that other types of Raman scattering
can be used to perform the systems and methods described
herein.

An analyte detection system can be included in a com-
puting device and can be used to identify the amount and/or
density of a particular analyte in a user's tissue. In some
examples, the analyte detection system can be integrated
into a wearable computing device. Such a wearable com-
puting device can include a smartwatch, a fitness band, or
any other type of wearable computing device. In some
examples, a wearable computing device can be worn such
that the analyte detection system can be placed directly
against the skin of a user. In this way, the analyte detection
system can unobtrusively measure an analyte without spe-
cial action taken by the user.

The analyte detection system can include a Raman pump
source that projects light at a particular wavelength (e.g.,
850 nanometers). A detector can measure light reflected at
the wavelength of the Raman pump source. This can be the
light that was not Raman scattered and instead has the same
wavelength as the light generated by the pump laser. The
peak that is detected at the wavelength (e.g., 850 nanome-
ters) emitted by the Raman pump source can be referred to
as a Rayleigh peak. Rayleigh scattering can refer to light that
is emitted by the target sample and has the same wavelength
as the pump light. Rayleigh scattering is much more com-
mon than Raman scattering and thus the intensity of light at
the Rayleigh peak can be higher than the intensity measured
for light that is the result of Raman scattering.

Raman scattered light can be detected at one or more
particular wavelengths or within certain ranges of wave-
lengths (depending on the specific analytes to be measured).
This light is the result of spontaneous Raman scattering in
which the light emitted by the target material has a different
wavelength than the light produced by the pump laser. The
range of wavelengths generated by Raman scattering by a
particular molecule can be referred to as the Stokes range of
that molecule for emitted photons that have a higher wave-
length than the originally projected photons or the anti-
Stokes range for photons that have a lower wavelength than
the originally projected photons.

To increase the amount of Raman scattered light, one or
more Stokes lasers can be included in the analyte detection
system and can project light into the target material. In some
examples, the Stokes source(s) can provide light over a
wavelength range that is associated with an analyte. The
Stokes source can be a broadband light source that provides
light at all wavelengths within the wavelength range. As a
result of the presence of one or more Stokes sources, the
Raman response can be significantly higher. As a result, the
presence of an analyte can more easily be identified.

An important factor that determines the amount of Raman
scattered light that occurs (and is therefore more easily
detected) is the power density of the light projected into the
area of the target tissue. As such, the light from the light
sources can be focused on a relatively small area of the
user's tissue (to increase the power density in that small
area). For example, the targeted area can have a diameter
that is approximately 1 micrometer. When the light is
focused on a small area in the tissue, the type of the tissue
at that location can significantly impact the effectiveness of
the system in identifying the presence, amount, and/or
density of an analyte.

Thus, the analyte detection system can identify the type of
tissue at a variety of different locations within the possible
target zone. In this way, the analyte detection system can identify a specific location that has an optimal tissue type to
detect a particular analyte. To do so, the analyte detection
system can perform a sparse sampling process. To perform
the sparse sampling process, the analyte detection system
can determine a three-dimensional area which can be tar-
geted by the one or more light sources (e.g., the Raman
pump source and the one or more Stokes sources). The
three-dimensional area that can be targeted can be based on
the control mechanisms available to the beam controller. For
example, one or more mirrors can be included in or acces-
sible to the analyte detection system. The one or more
mirrors can be tilted such that the light generated by the one
or more light sources can be targeted at different points
along the surface of the tissue of a user. The total possible
targeting range (e.g., in the direction defined by an x-axis
and a y-axis) can be the boundaries of the area which can be
targeted.

In addition, one or more lenses can be included that can
be adjusted to control the focus depth of the light sources.
The one or more lenses can be moved closer together or
farther apart, thus adjusting the depth at which the light is
focused. In some examples, one or more of the lenses is
fixed and one or more can be moved up or down by rotation
of a screw. In some examples, the adjustable lenses are
circular such that rotating the lenses will not affect the light
as it passes through. The degree to which the lenses can
adjust the focus depth of the light sources can determine the
depth of the area which can be targeted (e.g., the z-axis of
the area).

A target sampling grid of points can be generated to cover
the entire area that can be targeted at a particular density. In
some examples, a higher density of points can be used to get
a higher resolution of the type of tissue in the area. However,
increasing the number of points can result in increased time
and power used.

Once the target sampling grid of points has been estab-
lished, the analyte detection system can emit light from one
or more of the light sources (e.g., the Raman pump light
and/or the Stokes light) at each grid location. In some
examples, when used to determine the type of tissue at a
particular location, the light sources operate at lower power
and for a smaller amount of time than when used to perform
analyte detection. In this way, the time and power used to
identify the type of the tissue at each point in the sparse
sampling grid can be reduced. In some examples, the analyte
detection system can project light at each point in the grid of
points sequentially. To do so, the beam controller can adjust
the one or more light sources to target a respective point.
One or more of the Raman pump light source and the one or
more Stokes light sources can be engaged to emit light at the
respective point. The photodetector can then determine the
frequencies that are absorbed by the respective point based
on the frequencies of light that are detected. Any frequency
of light that is projected and not detected by the photo
detector can be determined to be absorbed. Similarly, if the
intensity of light in one or more particular frequencies is
reduced relative to other frequencies, the system can deter-
mine that the light at those frequencies is at least partially
absorbed. This process can then be repeated for each point
in the target sampling grid of points.

The analyte detection system can detect the light that is
absorbed by the respective point. As noted above, the
photodetector can detect the light emitted out of the tissue
and determine which wavelengths were absorbed. In some
examples, the wavelengths that were determined to be
absorbed at each respective point in the target sampling grid
can be analyzed. Different types of tissue can absorb different frequencies of light. As a result, the absorbed wavelengths of light can be used to estimate the type of the tissue at the respective point of the target sampling grid. The analyte detection system can store the type of tissue that has been estimated for each point in the target sampling grid. In some examples, each time the analyte detection system detects analytes in the tissue of a user it can perform a new sparse sampling of the target area.

In other examples, the analyte detection system can store tissue type data for future use. In this way, a map of the type of a user's tissue can be generated. In some examples, once a map of the type of a user's body is generated, the analyte detection system can scan fewer points in the target sampling grid and use that data to accurately determine which portion of a user's tissue is currently within the target area. Thus, if the analyte detection system is included in a user computing device such as a fitness band or smartwatch, small changes in the position of the user computing device will not result in the need for a new scan of all points. Instead, a scan of a reduced number of points can enable the analyte detection system to determine the current position of the user computing device from a relatively small number of possible positions that are already well mapped.

In some examples, the user computing device can include an accelerometer to measure the motion of the user computing device, both in absolute terms and relative to the body of a user. In this way, the user computing device can determine whether to perform a new scan (if significant motion relative to the user's body has occurred) or not.

In some examples, the analyte detection system can select a point from the plurality of points in the target sampling grid as an optimal target location. In some examples, the optimal target location can be selected based on the type of tissue at that location and/or the specific analyte that is being detected. Thus, some analytes are more readily detected in blood vessels or interstitial fluids.

Once the optimal target location is determined, the beam controller can target the light sources (e.g., the Raman pump source and the one or more Stokes sources) at the optimal target location. The analyte detection system can measure the light emitted by the tissue to detect the presence of one or more analytes as discussed above.

Embodiments of the disclosed technology provide a number of technical effects and benefits, particularly in the area of detecting analytes in the target material. In particular, embodiments of the disclosed technology provide improved techniques for detecting analytes in the tissue of a user. For example, one particular technical problem that arises in the area of analyte detection is that detection is more readily accomplished in some types of tissue than others. When the light source is focused on a very small area of tissue, focusing on a tissue type that is not optimal for detecting analytes can result in failure to accurately detect the analyte. To overcome this problem, the disclosed technology describes using an initial scan to determine the type of tissue at a plurality of different points and selecting a point with an appropriate type. Doing so increases the accuracy and effectiveness of the analyte estimation system while reducing total power consumption. Reducing power consumption while improving the accuracy and effectiveness of the system results in a significant benefit to the users.

With reference to the figures, example embodiments of the present disclosure will be discussed in further detail.

FIG. 1 illustrates an example analyte estimation system for scanning an area of the arm of a user non-invasively in accordance with example embodiments of the present disclosure. In this example, the analyte measurement system can measure the analyte in tissue of the arm 130 of the user. One or more light sources 134 of the analyte measurement system can project light onto any portion of the scanning region 132 of the arm of the user.

The analyte measurement system can initially determine an optimal target location for the projected light within the scanning region 132 that the light can be projected. To determine which particular area of the total area 132 the one or more light sources 134 should target, the analyte measurement system can initially sample the total area 132. To do so, the one or more light sources 134 can be targeted at a series of locations. for example, the locations can include 140-1, 140-2, and 140-3. Many more locations are shown but are not labeled for ease of discussion. The one or more light sources 134 can first target 142-1 the first location 140-1. The one or more light sources 134 can subsequently target 142-2 the second location 140-2. The one or more light sources 134 can subsequently target 142-3 the second location 140-3. The one or more light sources 134 can continue to target each location in the grid. For each location, one or more light sources 134 can project light at the location. A light detector can then measure the amount, wavelengths, and intensity of light emitted from the target location. By comparing the wavelengths and intensity of the emitted light, the analyte detection system can determine the light absorption characteristics of the targeted location.

Figure 2A:
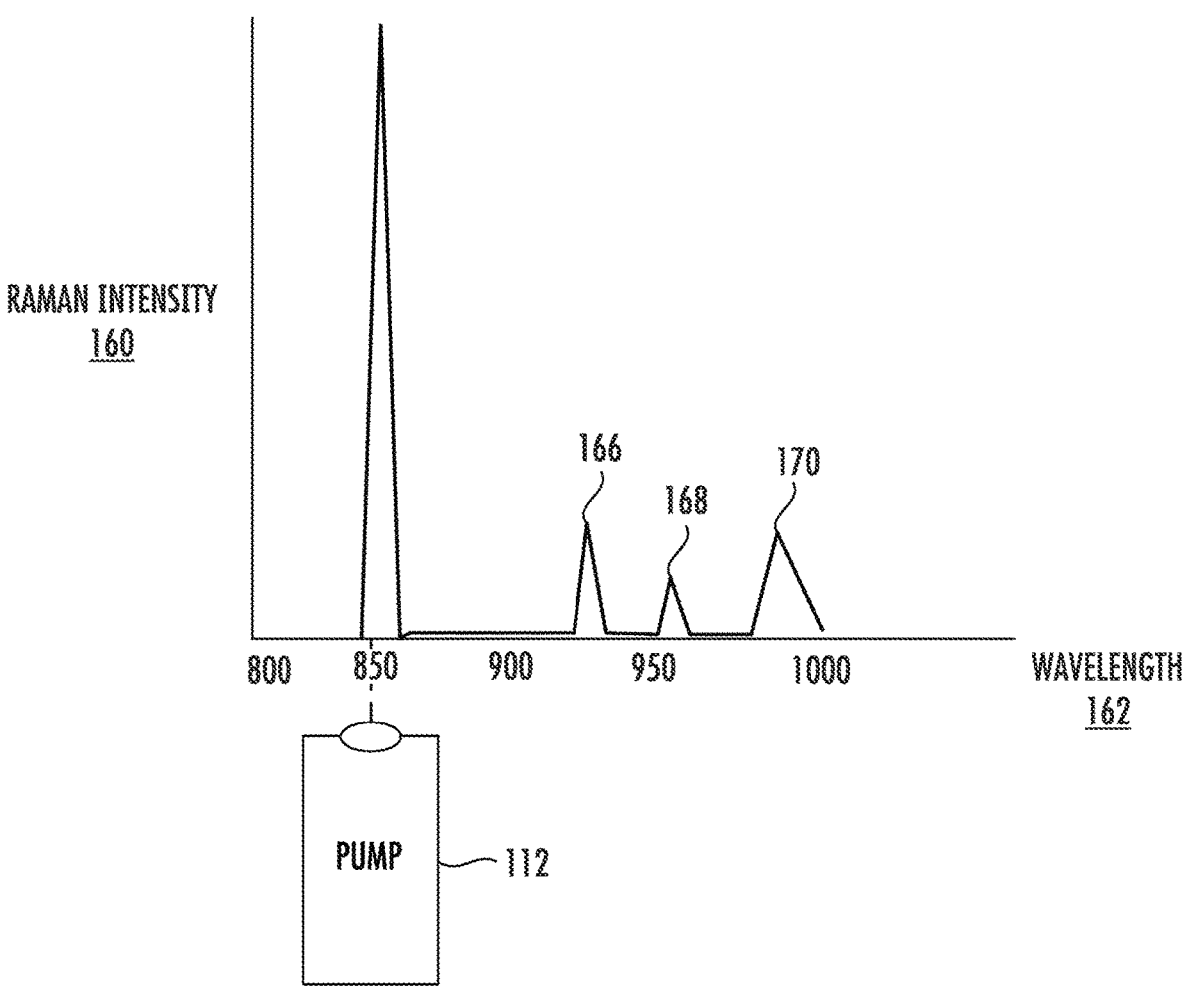
FIG. 2A illustrates a graph of the wavelength and intensity of light resulting from spontaneous Raman scattering when light is projected into a target material.

FIG. 2A illustrates a graph of the wavelength 162 and intensity 160 of light resulting from spontaneous Raman scattering when light is projected into a target material. In this example, a pump laser 112 can project light at a particular wavelength (e.g., 850 nanometers). As seen in the example graph, light with high intensity is measured at the wavelength of the pump laser 112. This represents the light that was not Raman scattered and instead has the same wavelength as the light generated by the pump laser 112. The peak that is detected at the particular wavelength (e.g., 850 nanometers) emitted by the Raman pump source can be referred to as a Rayleigh peak. Rayleigh scattering can refer to light that is emitted by the target sample and has the same wavelength as the pump light. Rayleigh scattering is much more common than Raman scattering and thus the intensity of light at the Rayleigh peak can be higher than the intensity measured for light that is the result of Raman scattering.

In this particular example, Raman scattered light is detected between approximately the wavelengths of 900 nanometers and 1000 nanometers. However, other ranges of wavelengths can be measured depending on the specific analyte to be measured. This light is the result of spontaneous Raman scattering in which the light emitted by the target material has a different wavelength than the light produced by the pump laser 112. The range of wavelengths generated by Raman scattering by a particular molecule can be referred to as the Stokes range of that molecule for emitted photons that have a higher wavelength than the originally projected photons or the anti-Stokes range for photons that have a lower wavelength than the originally projected photons. The specific features of the detected Stokes range, including but not limited to the wavelengths at which peak intensity is measured, can be analyzed to generate a Raman signature for the molecule. The Raman signature can represent specific features of a detected Stokes range (e.g., peaks) that are associated with a particular molecule. In this manner, the Raman signature can allow a specific molecule to be identified by analyzing the Stokes range that results when the specific molecule is present in the target material. Not pictured is the anti-Stokes range which can occur on the other side of the Rayleigh peak and represents Raman scattering in which the emitted light has a wavelength lower than the light generated by the pump laser 112. Although much of the present disclosure will be described in terms of the Stokes range, it will be appreciated that the disclosed concepts may be utilized with wavelengths within the anti-Stokes range.

In FIG. 2A, three peaks (166, 168, and 170) are present in the Stokes range. This information, as well as other information about the Stokes range, can be used to determine whether a particular analyte is present in the target material and at what concentrations. However, the amount of Raman scattering that occurs with spontaneous Raman scattering is very low. As a result, the information needed to identify a molecule by its corresponding Stokes range or Raman signature can be difficult to detect.

Figure 2B:
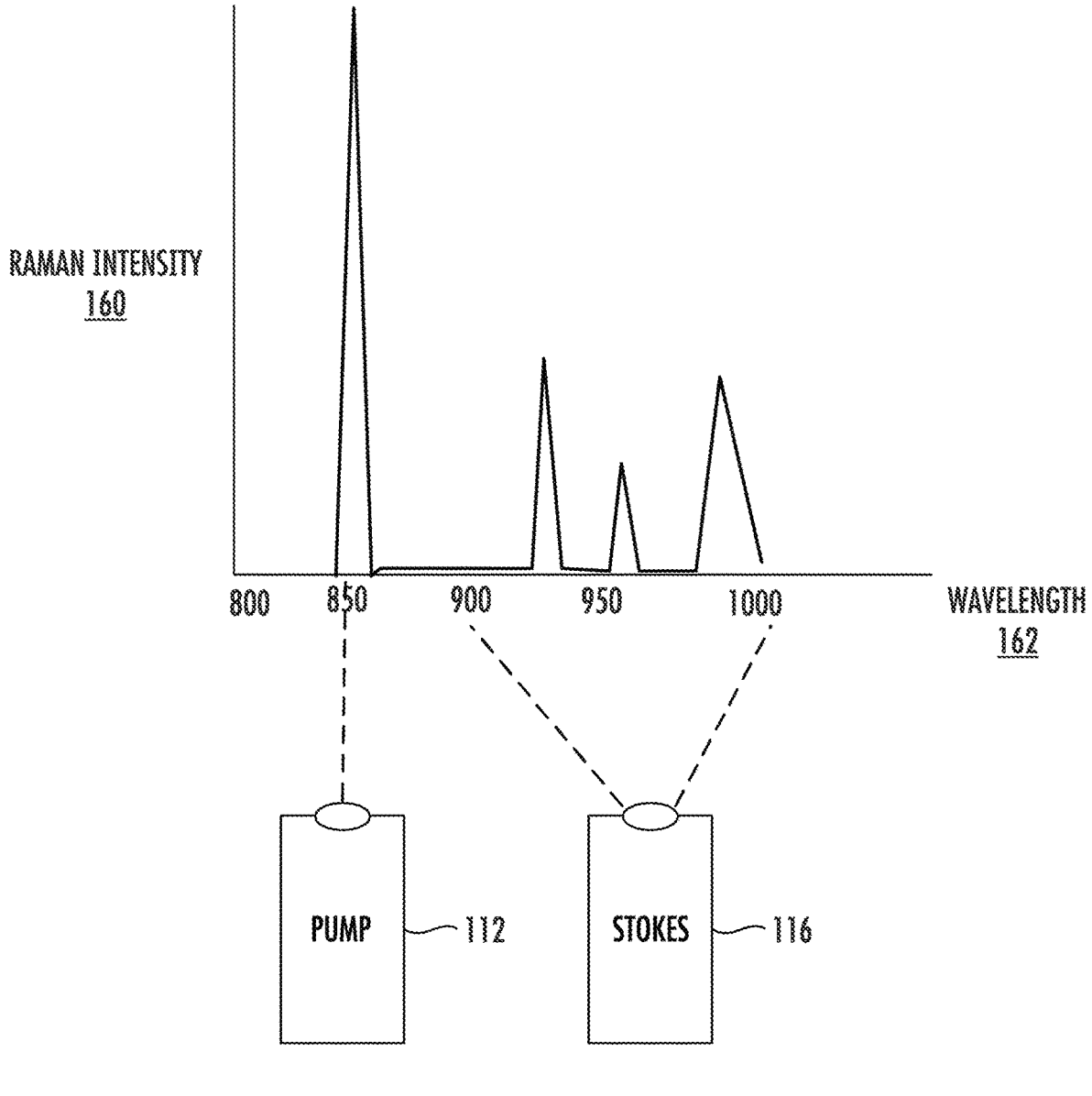
FIG. 2B illustrates a graph of the wavelength and intensity of light resulting from stimulated Raman scattering when light is projected into a target material.

FIG. 2B illustrates a graph of the wavelength 162 and intensity 160 of light resulting from stimulated Raman scattering when light is projected into a target material. In addition to the pump laser 112, one or more Stokes lasers 116 can project light into a target material. In some examples, the Stokes source(s) 116 can provide light over a wavelength range that is associated with an analyte. Traditionally, the Stokes source can be an LED that provides broadband light at all wavelengths within the wavelength range when the LED is turned on.

As a result of the Stokes laser 116, the Raman response is significantly higher. As a result, the Stokes range, and therefore the Raman signature, of the molecule can more easily be detected and the analyte can more easily be identified.

Figure 2C:
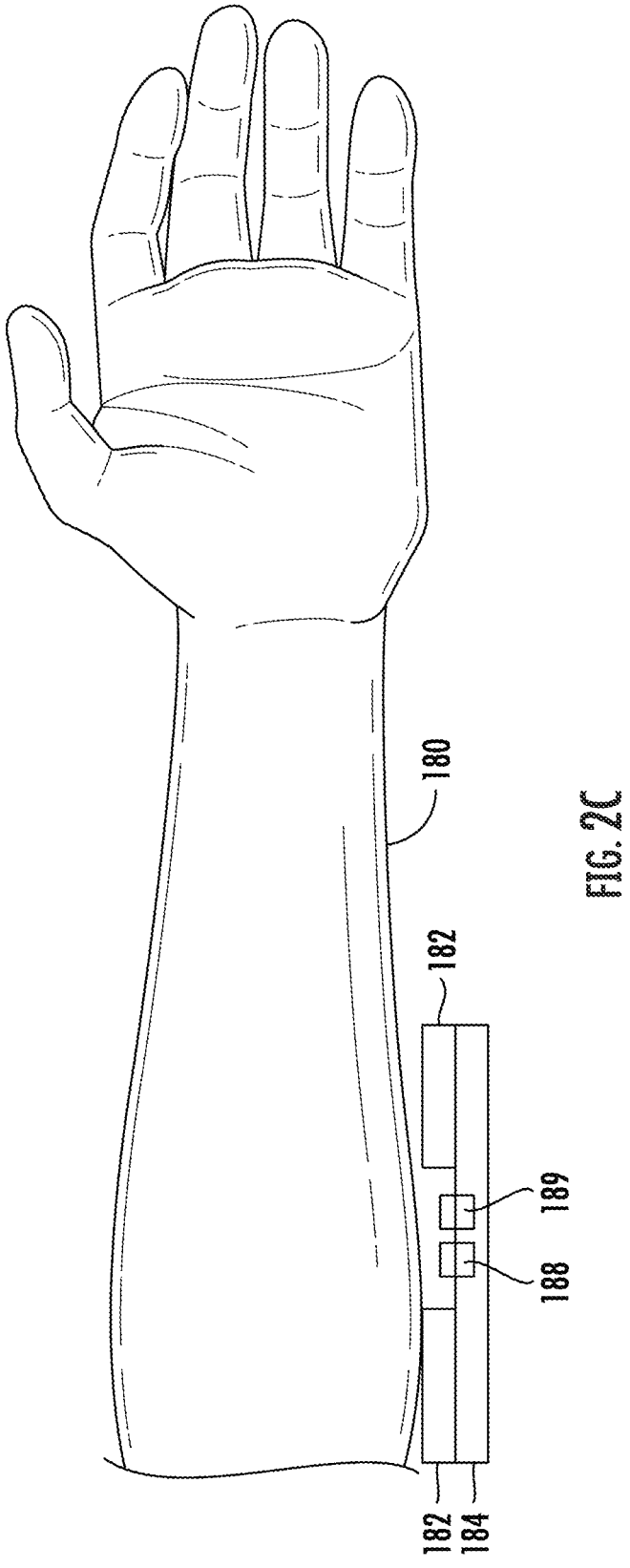
FIG. 2C illustrates an example analyte estimation system for measuring the analyte in the arm of a user non-invasively in accordance with example embodiments of the present disclosure.

FIG. 2C illustrates an example analyte estimation system for non-invasively measuring the analyte in the arm of a user in accordance with example embodiments of the present disclosure. A pump laser 188 (e.g., a first light source) can project light into the target material 180. In this example, the target material 180 is the skin and other tissue of the arm of a user. The projected light can be generated by the pump laser 188 at a first wavelength. The analyte estimation system can also include one or more Stokes lasers 189. To facilitate stimulated Raman scattering, the one or more Stokes lasers 189 can be configured to generate light at wavelengths associated with the Raman signature of a target analyte. The pump laser 188 and the one or more Stokes lasers 189 can be vertical-cavity surface-emitting lasers (VCSELs) and can be integrated into a printed circuit board (PCB) 184.

The one or more Stokes lasers 189 can be narrow-band light sources. The pump laser 188 also can be a narrow-band light source in some examples. As used herein, a narrow-band light source can project light such that the photons have wavelengths that fall within a narrow range of wavelengths relative to the relevant wavelength range (e.g., Stokes range) associated with the Raman-scattered radiation for the analyte of interest. In some examples, a narrowband light source can be defined based on the percentage of that wavelength range that is generated at a particular point in time. For example, a narrowband laser can generate light that falls within a bandwidth that is 10% of the total wavelength range that the laser can project. For example, if a particular Stokes laser 189 is tunable such that it can generate light within the range of 500 nanometers to 1500 nanometers, a narrowband laser can project light such the wavelength of each photon falls within a 100-nanometer range (e.g., 10% of the total range of the laser). In another example, a narrowband laser can be defined as a laser that projects light with a wavelength bandwidth of 1% of the total wavelength range of the laser. With this definition, the narrowband laser can produce light that falls within a 10-nanometer range (e.g., such that all the projected light has a wavelength within five nanometers of the target wavelength).

In some examples, the Stokes laser 189 can be a single tunable laser that can sweep a narrowband laser over the range of wavelengths that the tunable laser can produce. In some examples, the tunable laser can sweep over the wavelengths in the Stokes range of the target analyte. In another example, the Stokes laser 189 can include a plurality of laser diodes, each of which generates a narrowband of light centered around a wavelength in the Stokes range of the target analyte.

In some examples, the narrowband VCSEL light sources can be tunable over a relatively small range (e.g., approximately 5 nm range) using temperature and electrical current. In this way, the narrowband VSCEL light sources can be enabled to obtain a larger range without the extra components that are typically included in a tunable laser such as additional mechanical components integrated in the chip (e.g., MEMS mirrors) to allow for the wider tunability.

In some examples, other configurations can be used. For example, the analyte estimation system can include more than one pump laser combined with a tunable Stokes laser. Thus, the analyte estimation system can include. 2 pump lasers 188 that are 20 nm apart, and a single tunable Stokes laser 189 that can be tuned over a 20 nm range, resulting in a total of 40 nm range of possible Raman shifts. Additionally, or alternatively, with 3 pump lasers 20 nm apart the range can be tripled. Additionally, or alternatively, one or more fixed wavelength Stokes lasers 189 and a tunable pump laser 188.

The light projected by the pump laser 188 can excite one or more molecules within the target material 180 (e.g., electrons within the molecules are raised to a higher energy level). The molecules can return to a lower energy level and emit one or more photons. A photodetector 182 can detect light emitted from the target material 180. The detected light can be represented in a graph of the intensity of the light at various wavelengths.

The detected light can form a Stokes range for the molecule that was excited by incident light. The spectral intensity at wavelengths across the Stokes range for a particular analyte can form a specific Raman signature. In some examples, a Raman signature can be associated with a specific pattern based on the wavelengths at which peaks are detected, the spacing between peaks, and/or the intensity of light that is detected at one or more wavelengths. The features detected in the Stokes range can be compared to predetermined Raman signatures to determine one or more analytes present in the target material.

Data representing the Stokes range can include information representing the amount of light or intensity of light at each wavelength in a range of wavelengths included in the Stokes range. The data representing the Stokes range can be analyzed to determine one or more features, including peak wavelengths (e.g., wavelengths at which the measured intensity is higher than other nearby wavelengths), troughs, the distances between peaks, the distances between each peak wavelength, and the wavelength of the pump laser, and so on.

Figure 2D:
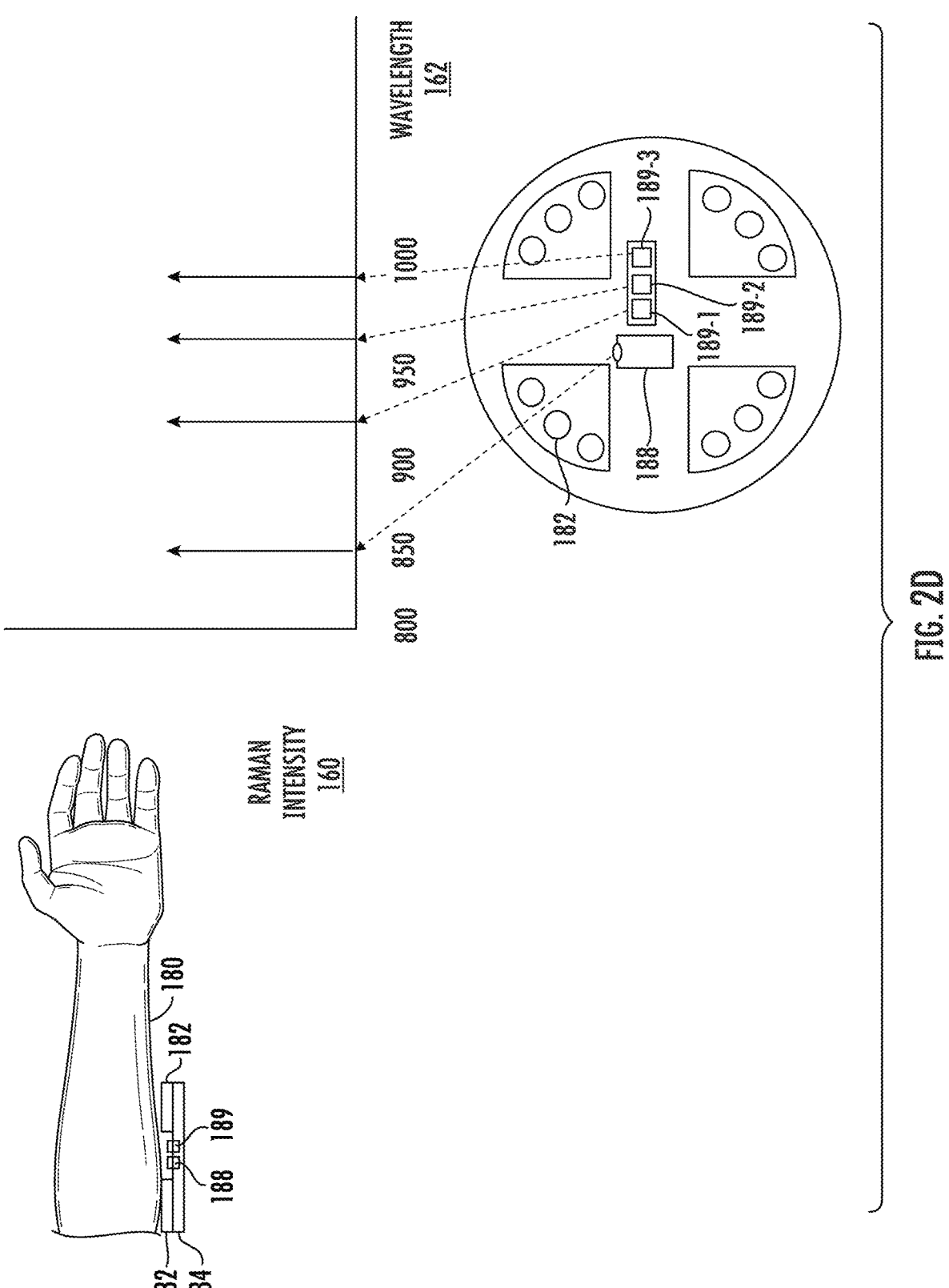
FIG. 2D illustrates an example analyte estimation system with multiple laser diodes for generating light at a particular wavelength within a Stokes range in accordance with an example embodiment of the present disclosure.

FIG. 2D illustrates an example analyte estimation system with multiple laser diodes generating light at one or more particular wavelengths within a Stokes range in accordance with an example embodiment of the present disclosure. As with FIG. 1C, a pump laser 188 can project light into a target material. A plurality of Stokes lasers (189-1, 189-2, and 189-3) can project narrowband light into the target material 180 with a center wavelength different from the center wavelength of the pump laser 188. Photodetectors 182 can be placed such that they measure light being emitted by analytes in the target material 180.

The Stokes lasers 189 can each generate narrow-band light (e.g., the light generated by the Stokes lasers falls within a particular wavelength band which can be represented as a percentage of the total wavelength range of the Stokes laser or as a specific wavelength number such as within 1 nanometer of the target wavelength) for a different wavelength within the Stokes range. In one example embodiment, the pump laser (e.g., the first light source) and the Stokes lasers (e.g., one or more second light sources) are VCSELs that each use 40 milliwatts of power. In other examples, different lasers that use different amounts of power can be used.

It should be noted that light can be measured based on its wavenumber rather than its wavelength. Wavenumber can represent the spatial frequency of an electromagnetic wave and can be measured relative to a base value (e.g., in this case, the light produced by the pump laser can be considered to have a wavenumber of 0 and the light produced by the one or more second sources can be given a wavenumber relative to the wavenumber of the light produced by the pump laser).

Figure 2E:
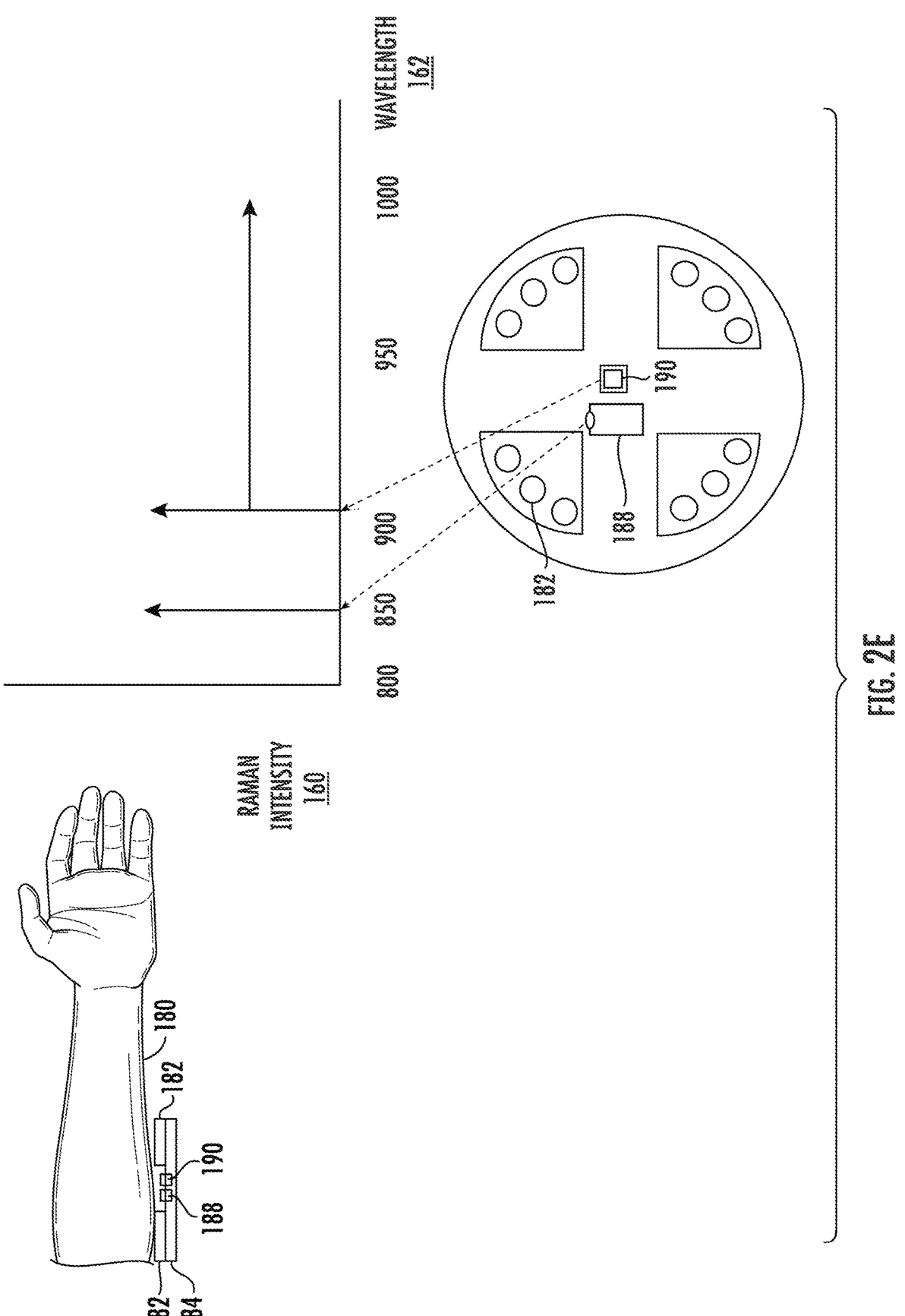
FIG. 2E illustrates an example analyte estimation system with a single tunable Stokes laser for generating light at different wavelengths within a Stokes range as needed in accordance with an example embodiment of the present disclosure.

FIG. 2E illustrates an example analyte estimation system with a single tunable Stokes laser 189 generating light at different wavelengths within a Stokes range in accordance with an example embodiment of the present disclosure. As with FIG. 1C, a pump laser 188 can project light into a target material. A tunable Stokes laser 190 can generate light that can project a narrowband of light into the target material 180 that can be adjusted to any wavelength within a Stokes range of interest. In some examples, the tunable laser can start with a narrowband of light at the low end of the Stokes range and adjust the wavelengths such that they sweep along the entire Stokes range without widening the narrowband of light wavelengths at any point. Photodetectors 182 can be placed such that they measure light being emitted by analytes in the target material 180.

Figure 3:
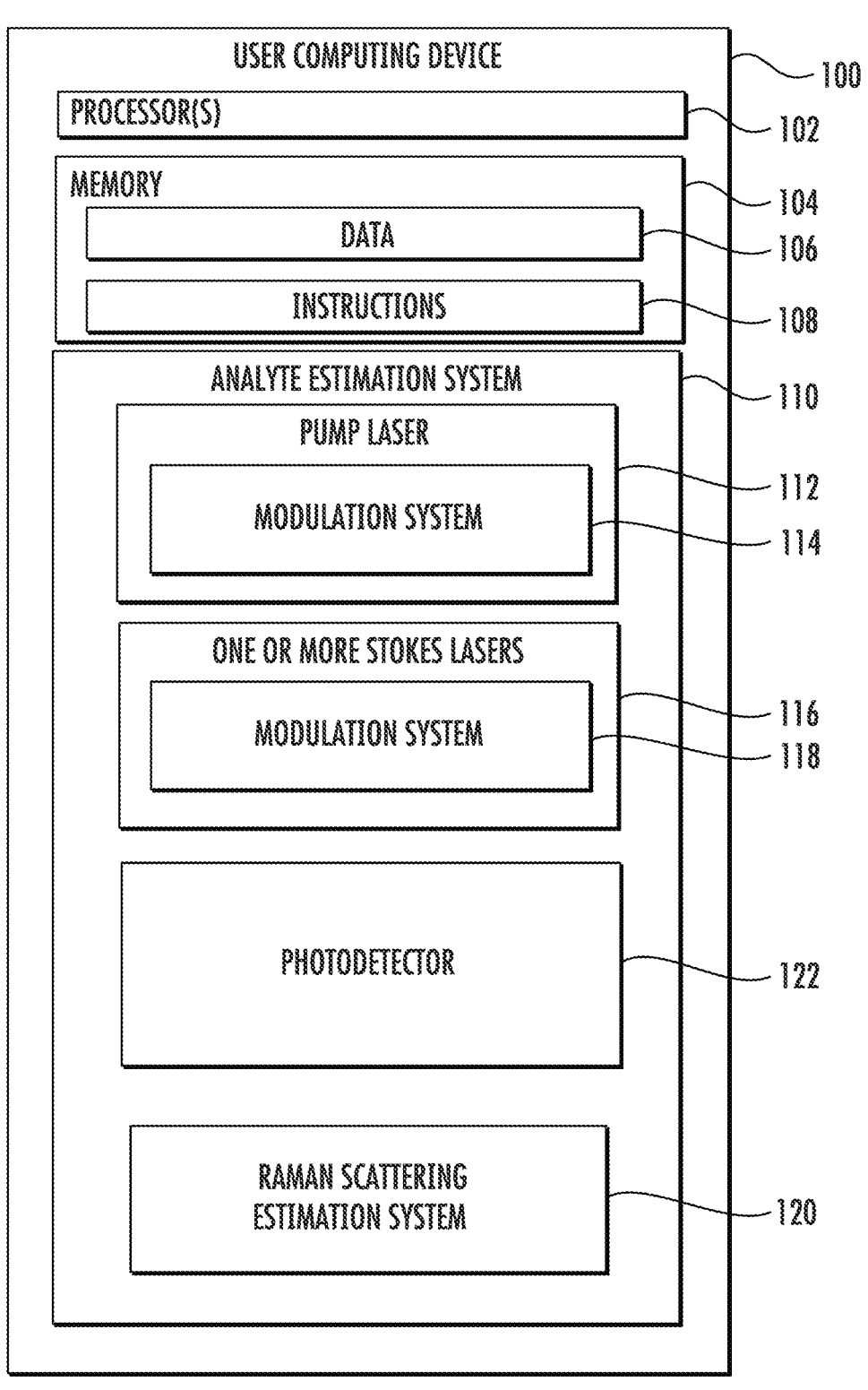
FIG. 3 illustrates an example computing environment including a user computing device in accordance with example embodiments of the present disclosure.

FIG. 3 illustrates an example computing environment including a computing device 100 in accordance with example embodiments of the present disclosure. The computing device 100 can include an analyte estimation system for non-invasively determining the presence and amount of one or more analytes internal to a user. In some examples, the computing device 100 can be a user computing device such as a smartphone or a wearable computing device. In other examples, the computing device 100 can be a computing device intended for home use and not for portability. In this example, the user computing device 100 can include one or more processors 102, memory 104, and an analyte estimation system 110.

In more detail, the one or more processors 102 can be any suitable processing device for a computing device 100. For example, such a processor can include one or more of: one or more processor cores, a microprocessor, an ASIC, an FPGA, a controller, a microcontroller, etc. The one or more processors can be one processor or a plurality of processors that are operatively connected. The memory 104 can include one or more non-transitory computer-readable storage media, such as RAM, ROM, EEPROM, EPROM, flash memory devices, etc., and combinations thereof.

In particular, in some devices, memory 104 can store instructions 108 for implementing the analyte estimation system 110. It will be appreciated that the term "system" can refer to specialized hardware, computer logic that executes on a more general processor, or some combination thereof.

Thus, a system can be implemented in hardware, application-specific circuits, firmware, and/or software controlling a general-purpose processor. In one embodiment, the system can be implemented as program code files stored on the storage device, loaded into memory, and executed by a processor or can be provided from computer program products, for example, computer-executable instructions, that are stored in a tangible computer-readable storage medium such as RAM, hard disk or optical or magnetic media.

Memory 104 can also include data 106 that can be retrieved, manipulated, created, or stored by the one or more processor(s) 102. In some example embodiments, such data can be accessed and used as input to the analyte estimation system 110. In some examples, the memory 104 can include data used to perform one or more processes and instructions that describe how those processes can be performed.

In some examples, the analyte estimation system 110 can include a pump laser 112, one or more Stokes lasers 116, a photodetector 122, and a Raman scattering estimation system 120. Although not pictured, the analyte estimation system 110 can also include an optical filter and one or more optical lenses (e.g., micro lenses) to focus the lasers on the same area (e.g., the same portion of the user's skin). The pump laser 112 (e.g., a first light source) can be a laser diode that emits light (e.g., a stream of photons) within a narrow wavelength band such that the emitted light has a particular wavelength within a certain range of the target wavelength. In some examples, the pump laser can produce narrowband light with an average wavelength of 780 nanometers. Other wavelengths of a pump laser 112 may be used, with the wavelengths of the one or more Stokes lasers 116 being determined based, at least in part, on the wavelength of the pump laser 112. In some examples, the pump laser 112 can be a vertical-cavity surface-emitting laser (VCSEL) included in a semiconductor chip. In some examples, the wavelength of the light emitted by the pump laser 112 is 850 nanometers. Other wavelengths can be used.

The pump laser 112 can include (or be associated with) a modulation system 114. The modulation system 114 can include a waveform generator that can produce a waveform that can be used to modulate the light produced by the pump laser 112. The pump laser can be referred to as a first light source. By modulating the light produced by the pump laser 112, the analyte estimation system 110 can differentiate (e.g., using a filter or lock-in amplifier) between light that the target material emits after being excited by the light that originated from the pump laser 112 and the light that the target material emits after being excited by the light that originates from the one or more Stokes lasers 116.

The one or more Stokes lasers 116 can include a tunable laser that can produce light with a wavelength within a predetermined range as needed. Thus, the tunable laser can be adjusted such that the wavelength of the light produced by the light source can change within a range. For example, in some examples, the tunable laser can be adjusted to emit light with a wavelength that can vary from 910 nanometers to 980 nanometers. In some examples, the wavelength of the light produced by the tunable laser can be determined based on the Raman signature of a particular analyte that the analyte estimation system 110 is trying to identify. In some examples, both the pump laser and the one or more Stokes lasers can use about 40 milliwatts of power to operate.

In some examples, the one or more Stokes lasers can include a modulation system 114. Thus, in some configurations, the pump laser 112 is modulated to distinguish the light produced by the pump laser 112 from the light produced by the one or more Stokes lasers 116. In other examples, the one or more Stokes lasers 116 are modulated to distinguish between the two light sources.

In some examples, the one or more Stokes lasers 116 can provide light with a wavelength tuned to the Raman signature of a particular analyte that the analyte estimation system 110 is trying to identify (e.g., glucose). By providing additional light (e.g., a stream of photons) with a wavelength determined based on the Raman signature of the analyte, the analyte estimation system 110 can enable stimulated Raman scattering to occur. Stimulated Raman scattering can result in the light provided by the one or more Stokes lasers 116 stimulating more Raman scattering than would be expected without the additional light provided by the one more Stokes lasers 116. Thus, introducing the light provided by the one or more Stokes lasers 116 can increase the detectability of a particular analyte in the sample material because the probability of Raman scattering is increased.

In some examples, the analyte estimation system 110 can include a photodetector 122. The photodetector 122 can be a sensor (e.g., a semiconductor device that converts light (e.g., photons) into electrical current) such as a photodiode. The photodiode can be configured to detect light over a range of wavelengths. In some example embodiments, light can be optically filtered such that only light within a specific wavelength range is detected by the photodetector. An amount of light can also be understood to be the number of photons detected and/or the intensity of the light measured at a particular wavelength.

In some examples, a filter can be employed to remove target-emitted light that is associated with the one or more Stokes lasers 116 such that only light originating from the pump laser 112 is detected. Similarly, an optical filter can filter out light with a wavelength associated with the pump laser 112 such that only target-emitted light that results from the Stokes lasers 116 or Raman scattering is detected by the photodetector. In some examples, a filter (or a lock-in amplifier) can remove modulated light, if the one or more Stokes lasers 116 were modulated, or unmodulated light, if the pump laser 112 was modulated.

The Raman scattering estimation system 120 can be used to detect the amount of light (e.g., the intensity of the light or the number of photons) generated by Raman scattering associated with an analyte in the sample material. In some examples, the Raman scattering estimation system 120 can determine the amount of light (e.g., either the number of photons or the intensity of the light) that has been Raman scattered to identify an analyte in the target material. In a first example, the user computing device can determine the amount of light at the pump wavelength (e.g., a first wavelength) that is lost (stimulated Raman loss). Alternatively, the user computing device can determine the amount of light at the Stokes associated wavelength that is gained (e.g., stimulated Raman gain). Either measurement or their combination can be used to estimate the amount of a particular analyte in the target material (e.g., a user's skin). A detected Stokes range can be compared to a reference spectrum to noninvasively measure the presence or absence of a target analyte.

For example, the sample material can be a portion of a user's body. The analyte can be, for example, glucose. Based on the amount of light having the predetermined second wavelength, the Raman scattering estimation system 120 can estimate the amount of the analyte in the target sample. In some examples, the estimated amount of the analyte can be presented for display to a user.

Figure 4A:
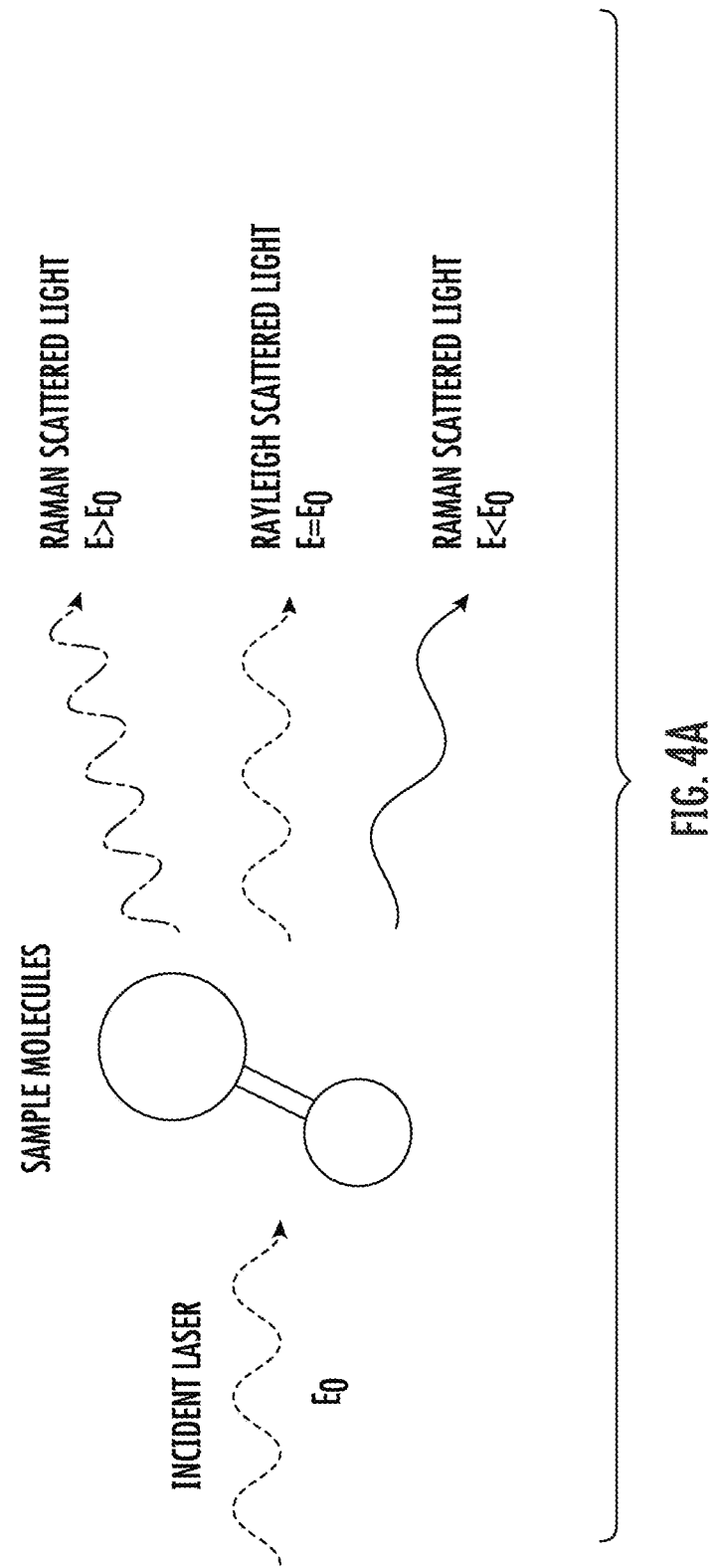
FIG. 4A illustrates an example of different types of photon scattering by matter in accordance with example embodiments of the present disclosure.

FIG. 4A illustrates an example of different types of photon scattering by matter. As seen in this example, an incoming photon 200 (e.g., the incident light) can interact with a particular sample molecule. One or more photons of the incident laser can interact with the sample molecules (e.g., with electrons in the sample molecules), temporarily raising the electron's energy level. When the energy level of the electron returns to its lower level, a photon is emitted. In some examples, this process can be referred to as scattering. Scattering can include Raleigh scattering and Raman scattering. In Raleigh scattering (which is a type of elastic scattering), the emitted photons have the same energy (and thus the same wavelength) as the incident photon but with the trajectory of the photon potentially altered. In Raman scattering, the energy level of the electron is changed, such that when the photon is emitted, the energy level (and thus the wavelength) of the photon is different than the incident photon. As a result, the presence of a particular sample molecule can be determined based on the presence or absence of Raman scattered light with particular altered wavelengths.

In some examples, the energy level of the target molecule can increase, resulting in a decrease in the energy of the Raman scattered light (referred to as Stokes Raman scattered light), or the energy level of the target and molecule can decrease, resulting in an increase in the energy of the Raman scattered light (referred to as anti-Stokes Raman scattered light).

It should be noted that, if the incident light has a consistent wavelength, the Raman scattered light will result in a particular Stokes range. The Stokes range can have a consistent Raman signature which can enable an analyte estimation system to distinguish the Raman scattering that results from one analyte from the Raman scattering that results from a second analyte. Thus, identifying the presence of a particular Raman signature can be used to estimate the presence of the target analyte and may also be used to estimate the amount of that analyte in the target substance.

Figure 4B:
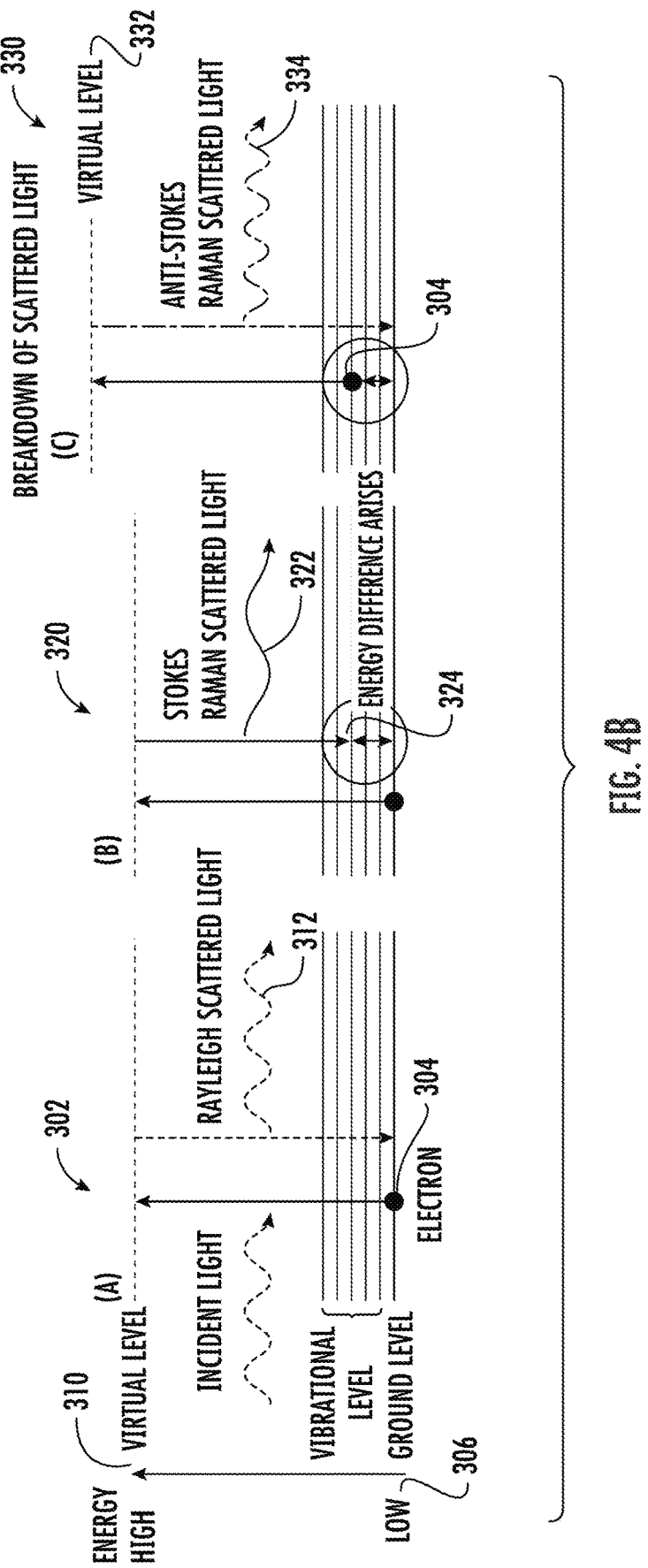
FIG. 4B illustrates an example of energy level changes of a molecule as a result of light scattering in accordance with example embodiments of the present disclosure.

FIG. 4B illustrates an example of energy level changes of an analyte as a result of light scattering. As seen herein, an electron 304 can have a first energy level 306 (e.g., a base energy level). In response to interactions with the incident light, the energy level of the electron increases. After a period of time, the electron 304 can emit a photon and return to a lower first energy level 306.

In a first example 302, the electron 304 is initially at a first energy level 306 (a low energy level). In response to the incident light, the electron 304 gains energy to a second energy level 310 higher than the first energy level 306. The electron 304 can emit the light as Rayleigh scattered light 312. In this example 302, the energy of the Rayleigh scattered light 312 is the same as the incident light (and thus has the same wavelength). The electron 304 can return to the first energy level 306 such that the total energy level of the system is maintained.

In a second example 320, the electron 304 is initially at a first energy level 306 (a low energy level). In response to the incident light, the electron 304 gains energy to a second energy level 310 higher than the first energy level 306. However, in this example, some of the energy is gained by the molecule as vibrational energy. As a result, when the Raman scattered light is emitted by the electron 304 the energy (and thus wavelength) of the emitted photon 322 is reduced but does not fall back down to the first energy level 306. Instead, the electron remains at the third energy level 324 which is higher than the first energy level 306 but lower than the second energy level 310. Thus, the total energy of the system is maintained because the electron 304 ends up at a third energy level 324 which is higher than the first energy level 306 but the scattered photon 322 is at a lower energy level than the incident light.

In a third example 330, the electron 304 is initially at a fourth energy level 332 higher than the first energy level 306. In response to the incident light, the electron 304 gains energy to a fifth energy level 334 higher than the second energy level 310. When the Raman scattered light is emitted, the electron 304 returns to the first energy level 306 having lost energy from its initial starting position at the fourth energy level 332. The scattered light 334 (referred to as anti-Stokes Raman scattered light) can have a higher energy level than the incident light.

Figure 5:
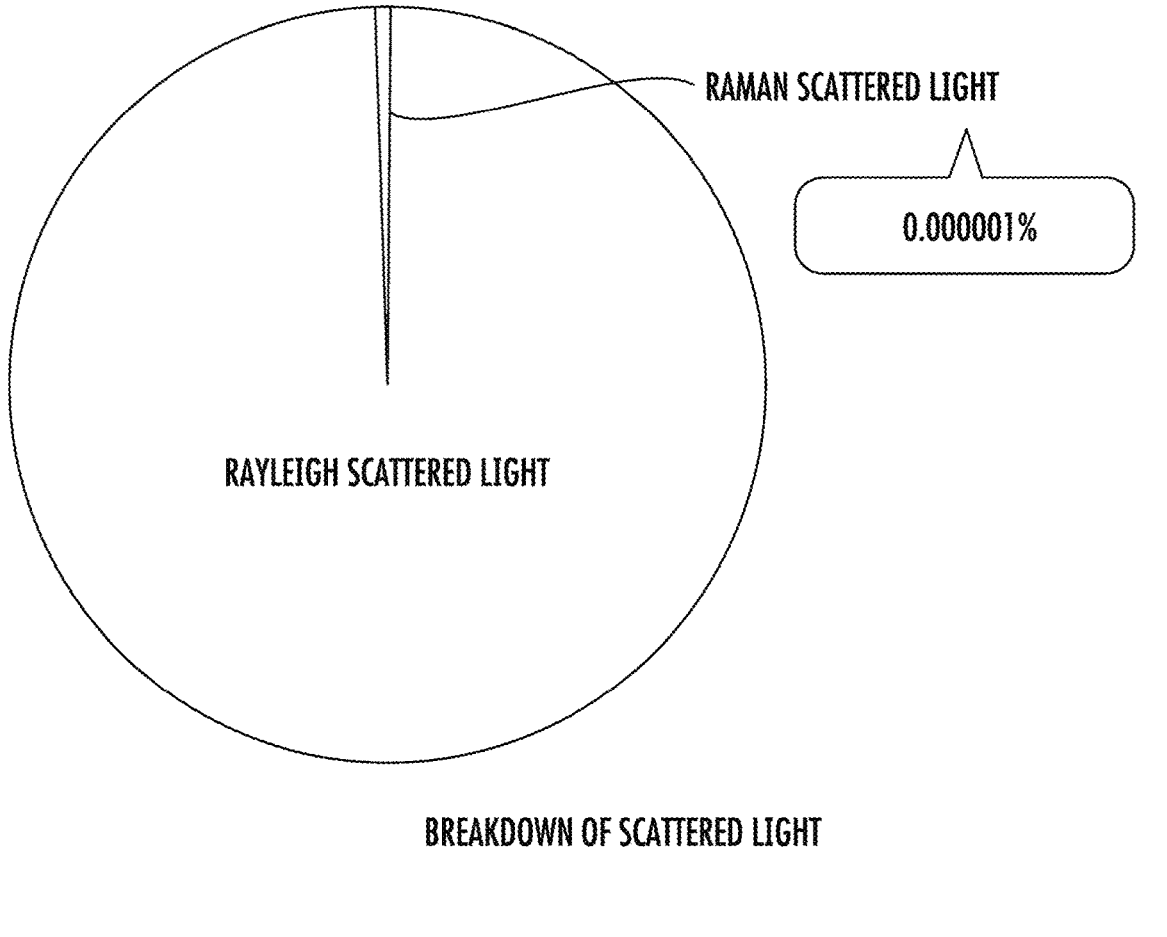
FIG. 5 illustrates a relative amount of Rayleigh scattered light and Raman scattered light for a typical analyte.

FIG. 5 illustrates a relative amount of scattered light. In this example, it is clear that the amount of Raman scattered light is a tiny fraction of the total amount of scattered light. Thus, if Raleigh scattered light represents more than 99.99 percent of all the scattered light, Raman scattered light can represent as little as 0.000001 percent of the scattered light. As such, the amount of Raman scattered light is much less than the total amount of scattered light. As a result, any technique to increase the amount of Raman scattered light can result in significant improvements in the ability of the detection system to determine whether or not an analyte is present.

Figure 6:
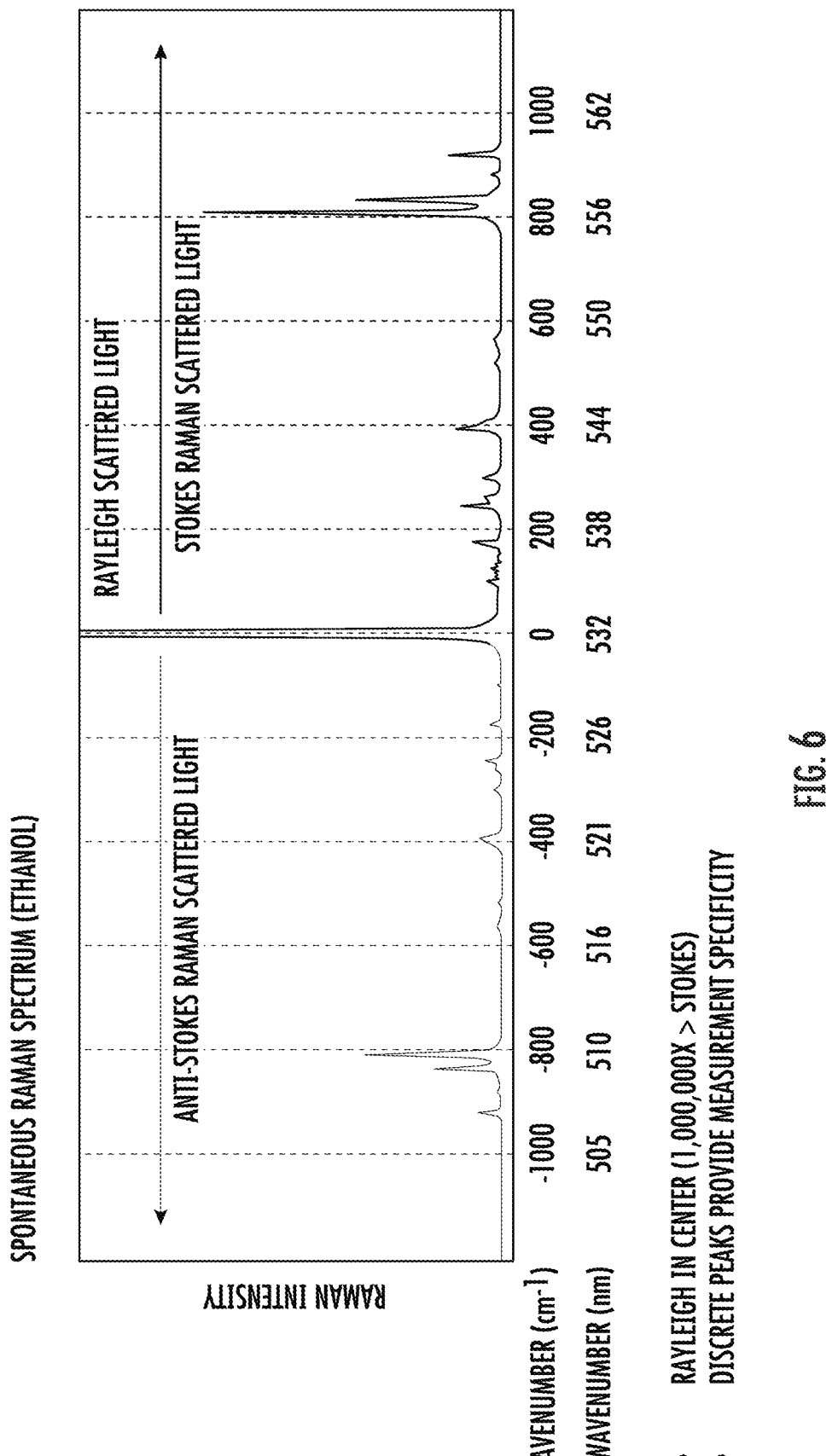
FIG. 6 illustrates a graph representing the wavelengths of scattered light in accordance with example embodiments of the present disclosure.

FIG. 6 illustrates a graph representing the wavelengths of scattered light in a Stokes range. In this example graph, the detected scattered light can be represented as a Stokes range that shows the wavelength of the detected light and its intensity. As can be seen, the majority of scattered light can be Rayleigh scattered light with the wavelength the same as the wavelength of the incident light generated by the pump laser. Thus, the peak at the 532-nanometer wavelength (wavenumber 0) is very high. Other peaks (e.g., at 800 nanometers and so on) can represent Stokes Raman scattered light (in which the light has lost energy) or anti-Stokes Raman scattered light (in which the light has gained energy) in a Stokes range associated with an analyte.

Figure 7:
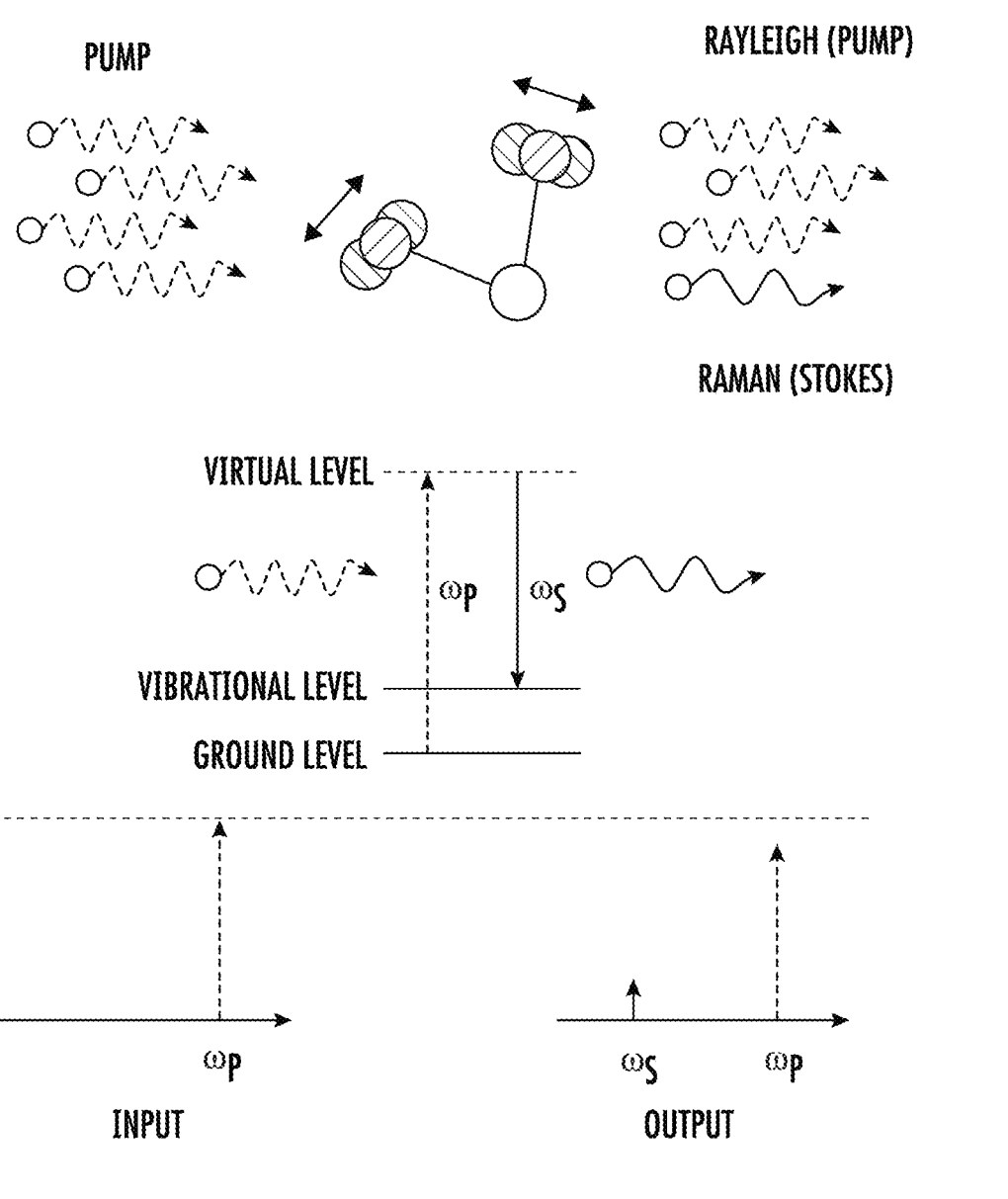
FIG. 7 illustrates spontaneous Raman scattering.

FIG. 7 illustrates spontaneous Raman scattering. For spontaneous Raman scattering, light generated by the first light source (or pump laser) can interact with a particular molecule. A small fraction of the photons that are emitted by the molecule(s) will have less energy and thus have a different wavelength than the incoming photons. As noted above, a particle in the molecule (e.g., an electron) can gain energy increasing from a ground level to a virtual level. In some cases, rather than returning to the ground level, one or more particles in the molecule can retain some energy as vibrational energy. Thus, the emitted photon has less energy than the incoming photon.

As a result, most of the emitted light retains the same wavelength as the incoming light. However, a small fraction of the incoming light is scattered such that the energy level of the scattered light and its wavelengths are different from the incoming light that excited the molecule. As noted above, the Raman signature of the scattered light can be used to determine what analytes are present in the target material.

Figure 8:
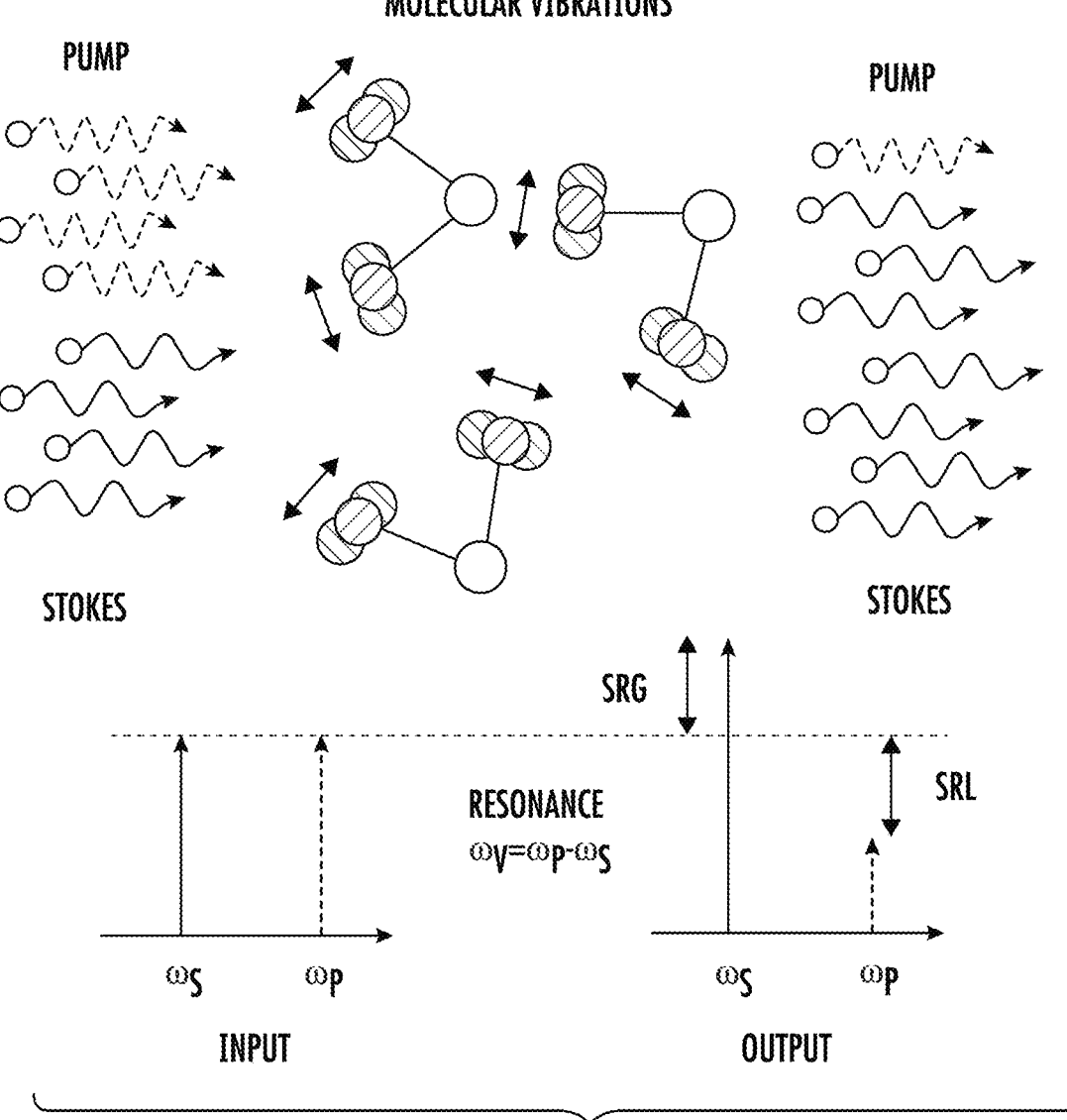
FIG. 8 illustrates stimulated Raman scattering.

FIG. 8 illustrates stimulated Raman scattering. In the case of stimulated Raman scattering, two or more light sources can be used to amplify or increase the amount of light that is scattered in by Raman scattering, thus increasing the average intensity of the Stokes range. In some examples, a pump laser can generate light with a first wavelength (as with spontaneous Raman scattering). In addition, one or more Stokes lasers can generate light with a second wavelength. The second wavelength can be a wavelength associated with the Raman signature of a particular analyte.

The light with the first wavelength and the light with the second wavelength can be combined and projected towards a target sample. A dichroic mirror (or one or more optical lenses) can be used but is not required. The light with a second wavelength can cause coherently driven molecular vibrations that have the effect of increasing the amount of Raman scattered light. As a result, less light is needed from the pump laser to result in a detectable amount of Raman scattered light.

In some examples, if the generated light can be equally split between the first wavelength and the second wavelength, the light emitted by molecules in the target sample can have more light that has the second wavelength. The difference between the amount of light with the second wavelength that is generated by the one or more Stokes lasers and the amount of light with the second wavelength that is measured after emission can be the amount of light that has been emitted with a different wavelength due to stimulated Raman scattering.

The light generated by the pump laser (or first light source) can excite a particular molecule to a higher energy level. A small fraction of the photons that are emitted by the molecule will be emitted with less energy (e.g., a particle in the molecule can retain some energy as vibrational energy) and with a different wavelength. As noted above, a particle (e.g., an electron) in the molecule can gain energy increasing from a base level of energy to a higher virtual energy level. In some cases, rather than returning to the base level, the one or more particles in the molecule can retain some vibrational energy and thus the photon emitted when the energy level of the electron returns to a lower level has less energy than the incoming photon.

As a result, most of the emitted light retains the same wavelength as the incoming light. However, a small fraction of the incoming light is Raman scattered such that the emitted light has a different energy level and thus a different wavelength. As noted above, the wavelength detected for the emitted light can be used to determine what analytes are present in the target material.

Figure 9A:
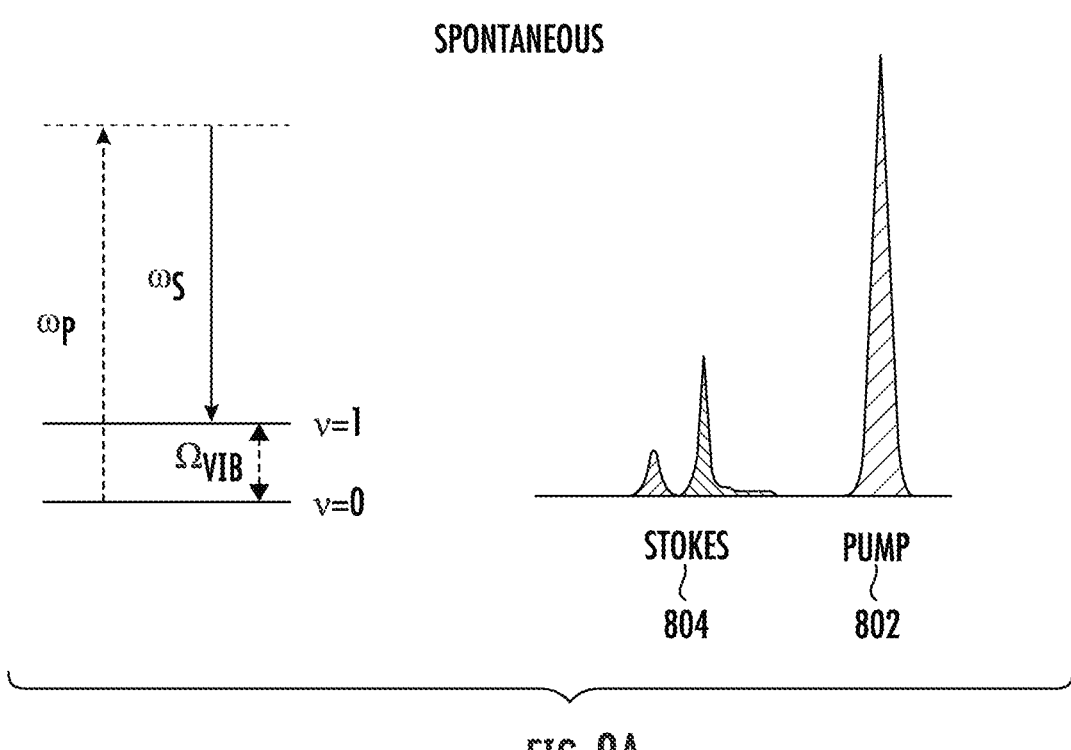
FIG. 9A illustrates an example graph representing the amount of light that is Raman scattered with spontaneous Raman scattering.

FIG. 9A illustrates an example graph representing the amount of light that is Raman scattered with spontaneous Raman scattering. As noted above, during spontaneous Raman scattering, a single light source can provide light with a first wavelength 802. A small portion of the light provided at the first wavelength 802 can excite a molecule to a higher energy level. Light with a second wavelength 804 can be emitted because some of the energy is retained by particles within one or more target molecules as vibrational energy.

Figure 9B:
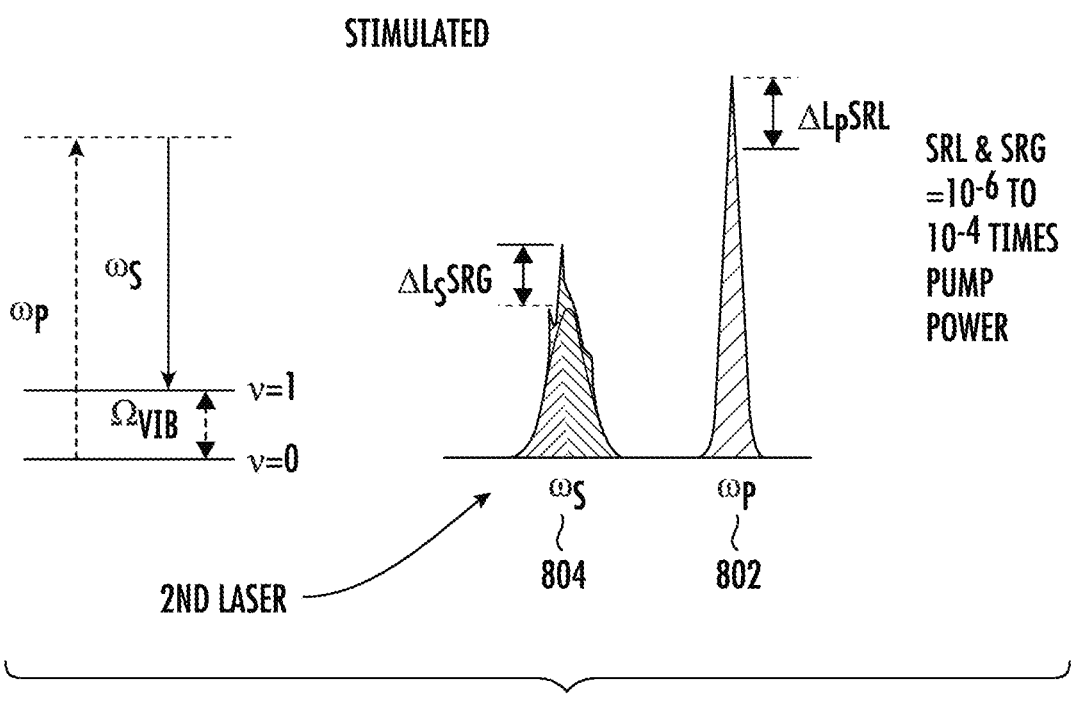
FIG. 9B illustrates an example graph representing the amount of light that is Raman scattered with stimulated Raman scattering.

FIG. 9B illustrates an example graph representing the amount of light that is Raman scattered with stimulated Raman scattering. In this example, a pump laser generates light at a first wavelength 802 and a Stokes laser can generate light whose wavelength is the second wavelength 804. As a result of resonance, the amount of Raman scattered light is increased by a first amount 806, making detection of the scattered light more efficient and requiring less power.

Figure 10A:
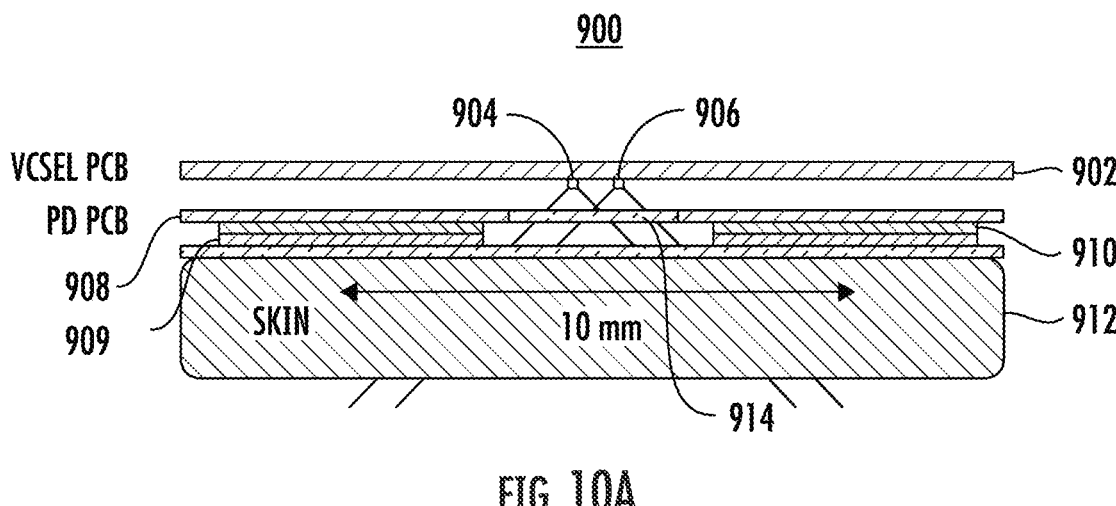
FIG. 10A illustrates an example configuration of a system for detecting analytes in a user's skin in accordance with example embodiments of the present disclosure.

FIG. 10A illustrates an example configuration of a system 900 for detecting analytes in a user's skin in accordance with example embodiments of the present disclosure. In this example, the relevant portion of an analyte estimation system 110 includes two printed circuit boards (PCBs). A first PCB 902 can include two light sources (VCSELs). The first light source 904 can be a pump laser that produces light at one or more first wavelengths and the second light source 906 can be a Stokes laser that produces light at one or more second wavelengths. The second wavelength(s) can be associated with the Raman signature associated with a target analyte.

The second printed circuit board 908 can include one or more photodiodes 910 that are configured to detect light. The one or more photodiodes 910 can produce a signal based on the detected light. In some examples, the signal produced by the photodiode(s) can be processed to remove a modulated portion of the signal generated in response to light produced by the Stokes laser 906. In this manner, the processed signal can represent light produced by Raman scattering of the pump laser 904. The analyte estimation system 110 can be pressed against the skin 912 of a user such that the light is projected down into the skin of a user and molecules included in the skin and/or tissue of the user can emit light into the photodiode 910. It should be noted that two PCBs are used in this example, but in some example embodiments, only a single PCB is used. If so, the photodiodes can be slightly raised from the surface.

The analyte estimation system 110 includes a single window 914 through which the light from both sources passes to interact with the skin 912 of a user. The light interacts with molecules in the user and in response light is emitted from the skin 912 of the user. The emitted light can pass through an optical filter 909 to the photodiode 910.

Figure 10B:
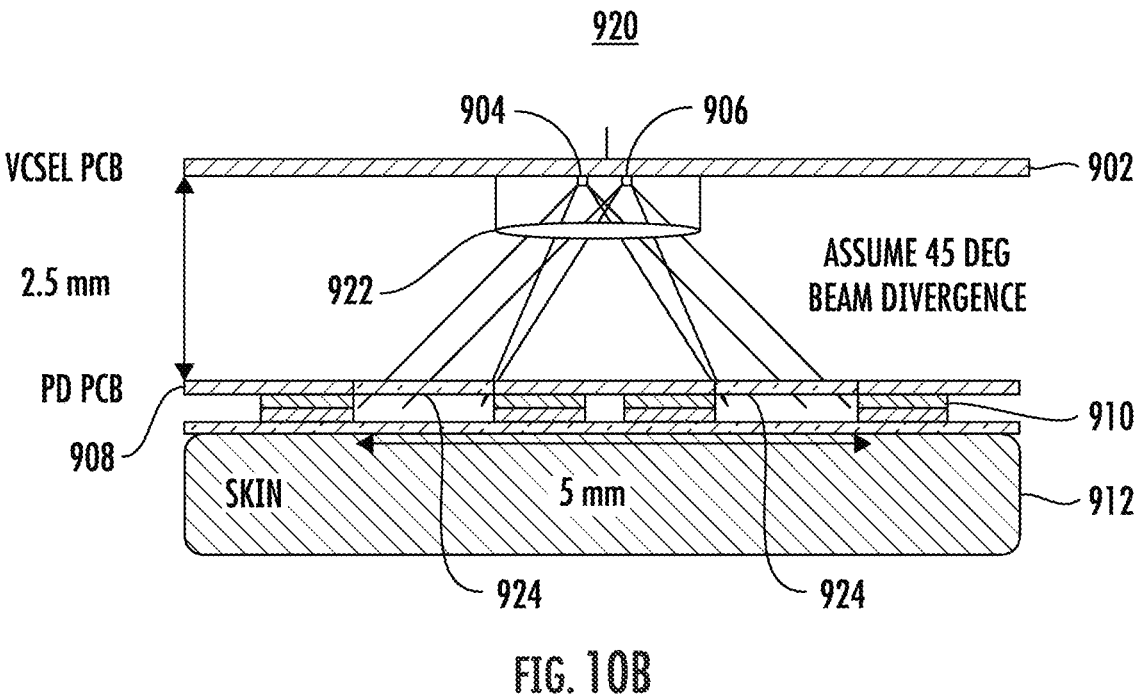
FIG. 10B illustrates an example configuration of a system for detecting analytes in the user's skin in accordance with example embodiments of the present disclosure.

FIG. 10B illustrates an example configuration of a system 920 for detecting analytes in the user's skin in accordance with example embodiments of the present disclosure. In this example, the relevant portion of the computing system includes two printed circuit boards (PCBs). A first PCB 902 can include two light sources (VCSELs). A first light source 904 can include a pump laser that can produce light at one or more first wavelengths and a second light source 906 can include a Stokes laser that can produce light at one or more second wavelengths. The second wavelength(s) can be associated with the Raman signature of a target analyte. The light from both light sources passes through an optical element 922 (e.g., a lens) before passing through two or more windows 924.

The second printed circuit board 908 can include one or more photodiodes 910 that are configured to detect light. One or more optical filters can be used to filter the received light for one or more target frequencies. For example, a long pass optical filter can be used to pass Stokes frequencies and reject pump frequencies. The one or more photodiodes 910 can produce a signal based on the detected light. In some examples, the signal produced by the photodiode(s) can be processed to remove a modulated portion of the signal generated in response to light produced by the Stokes laser 906. In this manner, the processed signal can represent light produced by Raman scattering of the pump laser 904. The analyte estimation system 110 can be pressed against the skin 912 of a user such that the light is projected into the skin of a user and molecules included in the skin and/or tissue of the user can emit light into the photodiode 910.

In this example, the analyte estimation system 110 can include two or more windows 924. The light from both sources 904 and 906 can be projected with beam divergence of 45 degrees through the two or more windows 924. Other angles can be used.

Figure 10C:
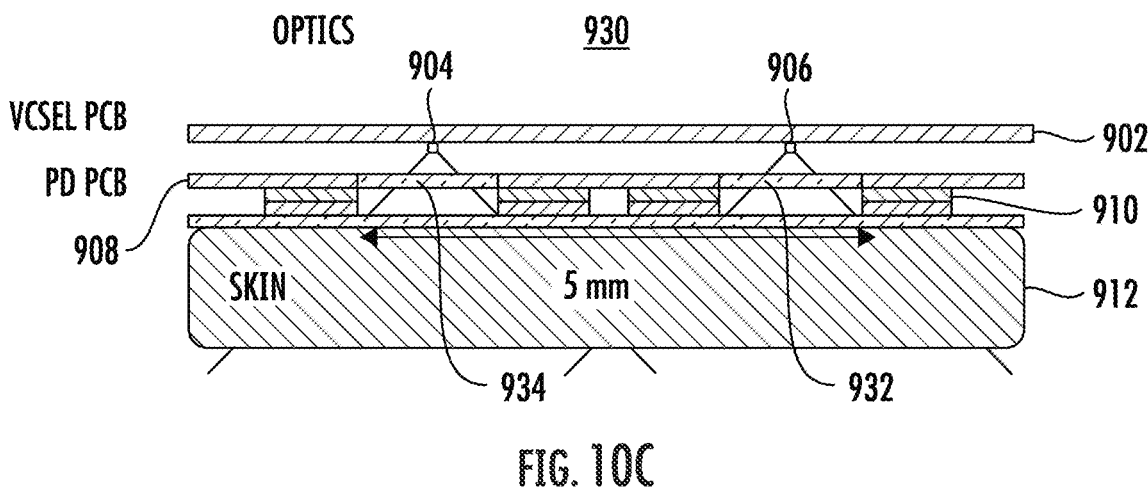
FIG. 10C illustrates an example configuration of a system for detecting molecules in the user's skin in accordance with example embodiments of the present disclosure.

FIG. 10C illustrates an example configuration of a system for detecting analytes in the user's skin in accordance with example embodiments of the present disclosure. In this example, the relevant portion of the computing system includes two printed circuit boards (PCBs). A first PCB 902 can include two light sources (VCSELs). A first light source 904 can include a pump laser that can produce light at one or more first wavelengths and a second light source 906 can include a Stokes laser that can produce light at one or more second wavelengths. The second wavelength(s) can be associated with the Raman signature of a target analyte. The analyte estimation system 110 includes two or more windows and each source passes their associated light through a respective window 932 or 934.

The second printed circuit board 908 can include one or more photodiodes 910 that are configured to detect light. The one or more photodiodes 910 can produce a signal based on the detected light. In some examples, the signal produced by the photodiode(s) can be processed to remove a modulated portion of the signal generated in response to light produced by the Stokes laser 906. In this manner, the processed signal can represent light produced by Raman scattering of the pump laser 904. The analyte estimation system 110 can be pressed against the skin 912 of a user such that the light is projected into the skin of a user and molecules included in the skin and/or tissue of the user can emit light into the photodiode 910.

Figure 10D:
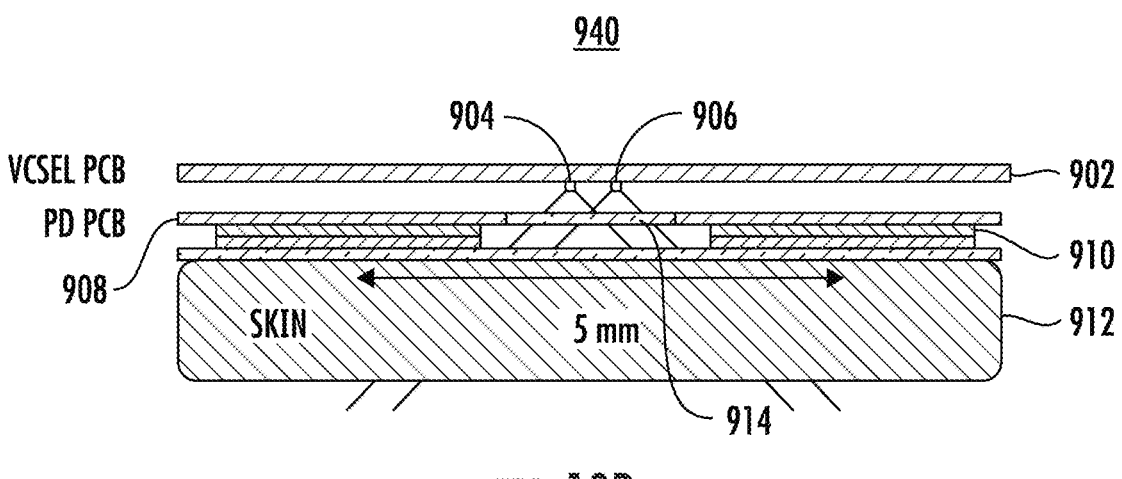
FIG. 10D illustrates an example configuration of a system 940 for detecting analytes in the user's skin in accordance with example embodiments of the present disclosure.

FIG. 10D illustrates an example configuration of a system 940 for detecting analytes in the user's skin in accordance with example embodiments of the present disclosure. In this example, the relevant portion of the computing system includes two printed circuit boards (PCBs). A first PCB 902 can include two light sources (VCSELs). A first light source 904 can include a pump laser that can produce light at one or more first wavelengths and a second light source 906 can include a Stokes laser that can produce light at one or more second wavelengths. The second wavelength(s) can be associated with the Raman signature of a target analyte.

The second printed circuit board 908 can include one or more photodiodes 910 that are configured to detect light. The one or more photodiodes 910 can produce a signal based on the detected light. In some examples, the signal produced by the photodiode(s) can be processed to remove a modulated portion of the signal generated in response to light produced by the Stokes laser 906. In this manner, the processed signal can represent light produced by Raman scattering of the pump laser 904. The analyte estimation system 110 can be pressed against the skin 912 of a user such that the light is projected into the skin of a user and molecules included in the skin and/or tissue of the user can emit light into the photodiode 910.

The analyte estimation system 110 includes a single window 914 through which the light from both sources passes to interact with the skin 912 of a user and light emitted from the skin 912 of the user can pass through to the photodiode 910. Thus, the light is projected through the window towards a user's skin 912. Light can be emitted from the skin 912 of a user such that it passes through one or more filters to the photodiode 910. The width of the area in which the analyte estimation system 110 contacts the skin 912 is 5 millimeters.

Figure 11:
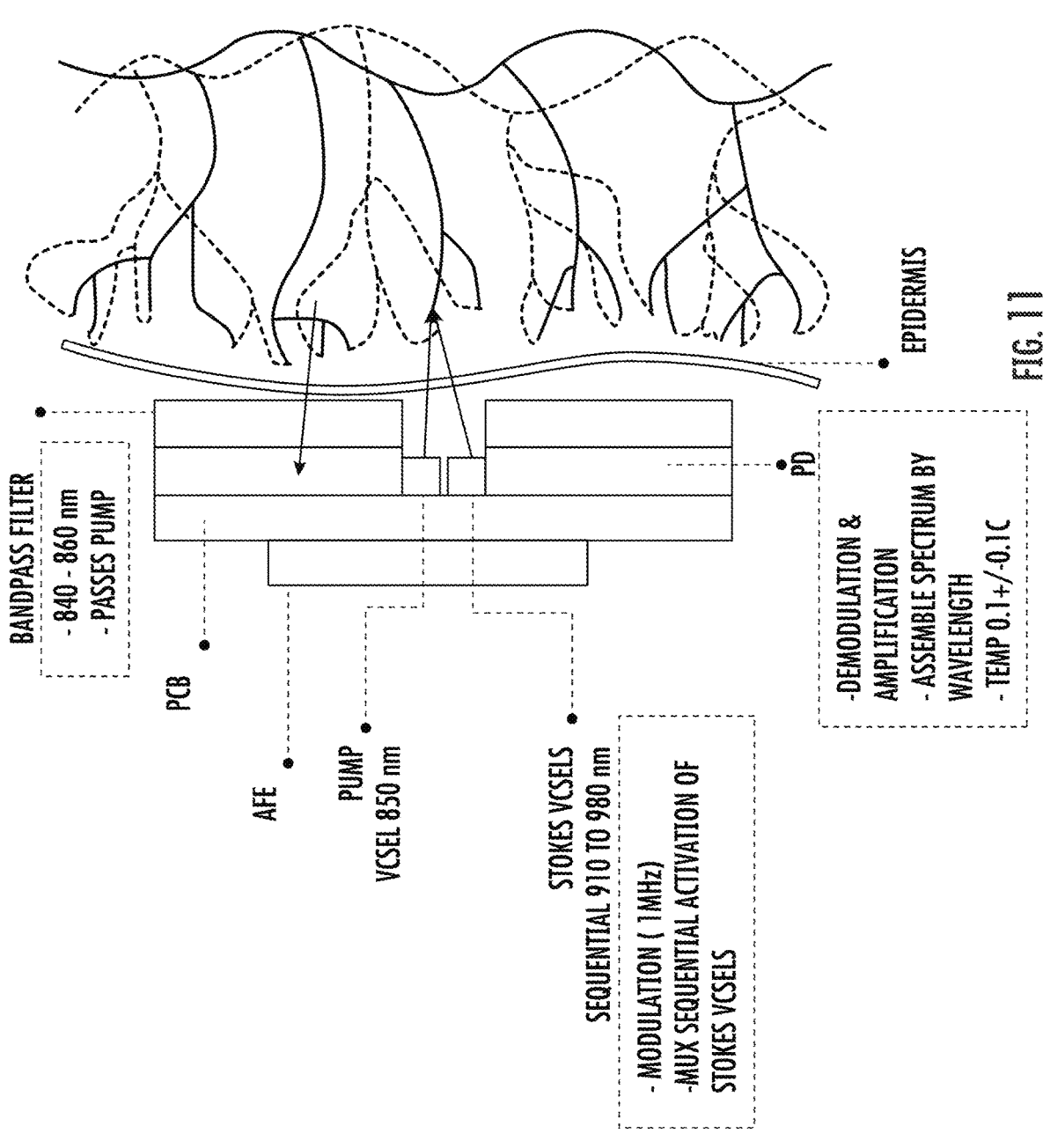
FIG. 11 illustrates an example system for detecting the presence of a molecule in the skin of the user in accordance with example embodiments of the present disclosure.

FIG. 11 illustrates an example system for detecting the presence of an analyte in the skin of the user in accordance with example embodiments of the present disclosure. The system can include a pump laser (e.g., a VCSEL) that produces light with a wavelength of 850 nanometers.

A second light source can be one or more Stokes lasers that can produce light in the range of 910 to 980 nanometers. Light from both the pump laser and the one or more Stokes lasers can be projected towards the skin of a user where it will encounter cells and blood vessels that contain a plurality of molecules. At least some of the light produced by the pump laser can excite a molecule in the skin of the users and be Raman scattered such that the photons emitted by the molecule have a different wavelength than the incoming light.

The system can include a bandpass filter that filters out light emitted from the epidermis of the user to remove light in a wavelength that is outside of the Stokes range. By filtering out wavelengths outside the Stokes range, the system can ensure that the measured light can be used to identify the Raman signature of any analytes in the skin and/or blood of the user. The nonfiltered light can then be sensed by a photodiode. The photodiode can generate an electrical signal. The electrical signal can be demodulated (e.g., using a lock-in amplifier) and amplified. In addition, if the Stokes lasers produce light at a plurality of wavelengths, the photodiode can assemble a spectrum from the various wavelengths. The amplified, demodulated, and assembled information can be analyzed to determine what molecules are present in the skin of the user and in what concentration.

Figure 12A:
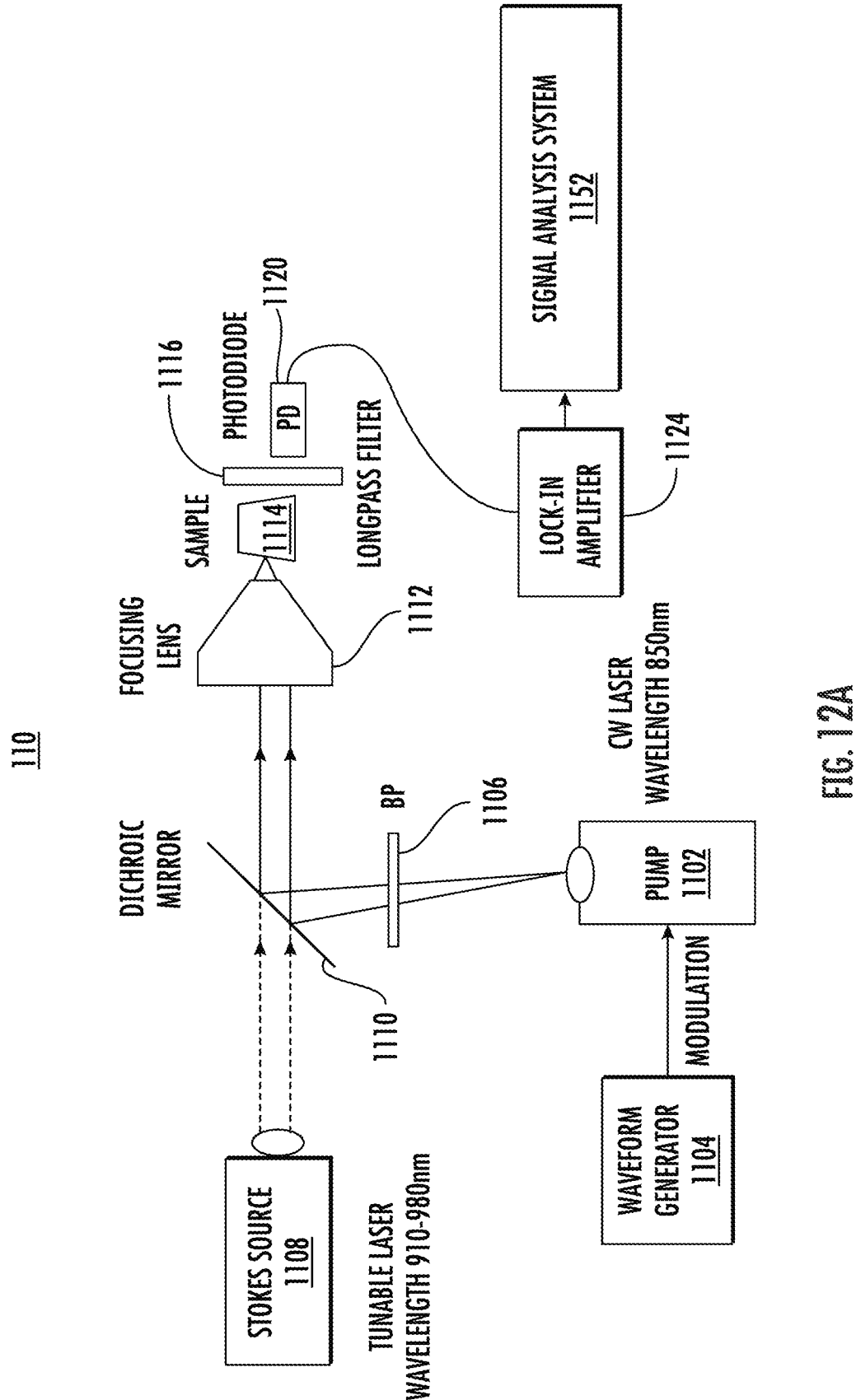
FIGS. 12A and 12B represent example molecule detection systems in accordance with example embodiments of the present disclosure.

FIG. 12A represents an example analyte estimation system 110 in accordance with example embodiments of the present disclosure. In this example, the analyte estimation system 110 can include a pump laser 1102. The pump laser 1102 can be referred to as a first light source. In some examples, the pump laser 1102 can produce light with a wavelength of 850 nanometers although other wavelengths may be used. In some examples, the pump laser 1102 can take the output of a waveform generator 1104 as input. The waveform generator 1104 can produce a signal to modulate the amplitude of the light produced by the pump laser 1102. In this way, the light produced by the pump laser 1102 can be distinguished from light produced from other light sources. Thus, the analyte estimation system 110 can determine whether the wavelength of particular light is the result of Raman scattering based on the modulation.

The light produced by the pump laser 1102 can pass through a bandpass filter 1106. The bandpass filter 1106 can ensure that only light within a particular frequency (e.g., the frequency associated with 850 nanometers) passes through the filter to the sample tissue. For example, the bandpass filter can ensure that only light with a wavelength of 850 nanometers passes through the filter to the sample tissue. The analyte estimation system 110 can also include a Stokes laser 1108 (e.g., referred to as a second light source) that produces light at a narrowband around one or more second wavelengths.

In some examples, the Stokes laser 1108 can be a tunable light source. A tunable light source can be controlled to produce light at a narrowband of wavelengths around any wavelength (e.g., within 0.1 nanometers of the target wavelength) within a given predetermined range. In some examples, the tunable light source can be controlled to produce a narrowband light that sweeps through a range of wavelengths from 910 nanometers to 980 nanometers. In another example, the Stokes laser 1108 can include a plurality of different light sources (e.g., laser diodes or other light-emitting diodes), each configured to output light with a particular wavelength associated with a Raman signature of a particular analyte. For example, the Stokes lasers 1108 can include a set of VCSELs, each tuned to provide light at a different wavelength within a Stokes range of an analyte.

In some examples, the plurality of Stokes lasers 1108 can be activated one at a time such that only one Stokes laser 1108 is activated at any particular point. In other examples, a plurality of Stokes lasers 1108 can be activated simultaneously.

In this example, respective Stokes lasers 1108 at different respective light wavelengths can be amplitude-modulated at different respective time frequencies, and then the response for each different respective light wavelength can be extracted from the combined-wavelength measured signal using time-based Fourier transform or other demodulation techniques, Exemplary time modulation frequencies for amplitude-modulating the different Stokes lasers 1108 can be in the range of 10 kHz-1 MHz, although the scope of the present teachings is not so limited.

The analyte estimation system 110 can include a dichroic mirror 1110 that is configured to ensure that light emitted from the pump laser 1102 and the Stokes laser 1108 is projected in the same direction. The dichroic mirror 1110 can, for example, allow light from either the pump laser 1102 or the Stokes laser 1108 to pass through while reflecting the light from the other source. By orienting the dichroic mirror 1110 correctly, the light from both sources can be caused to be projected in the same direction.

The analyte estimation system 110 can include a focusing lens 1112 that causes the light from both the pump laser 1102 and the Stokes laser 1108 to be focused and ensure it is directed towards the target sample. Once the light from the pump laser 1102 and the Stokes laser 1108 has interacted with the sample 1114, the sample 1114 can emit light that can be filtered by one or more filters 1116. For example, the emitted light can pass through a long pass filter, which can filter out light with the first wavelength that was produced by the pump laser 1102 and allow light with the second wavelength(s) to pass through. In this way, the light from the Stokes laser 1108 and any light from the pump laser 1102 that has been Raman scattered can be passed through the filter 1116.

The analyte estimation system 110 can include a photodiode 1120 that detects light that passes through the long-pass filter. In some examples, the photodiode 1120 can be configured to measure light at any wavelength within a predetermined range of wavelengths. The light detected by the photodiode 1120 can be used to generate an electrical signal. The electrical signal can retain characteristics of the light based on which it was generated. For example, if a portion of the detect light is modulated by amplitude, the resulting electrical signal can include both a direct current portion (e.g., associated with the unmodulated light) and an alternating current (AC) portion, associated with the modulated light).

In some examples, the amount of Raman scattering can be determined by using a lock-in amplifier to distinguish the modulated portion of the electrical signal from the unmodulated portion of the electric signal. The modulated portion of the light can be determined to be associated with stimulated Raman gain (SRG) that represents the amount of light from the pump laser 1102 that was scattered (e.g., emitted from the target material at a different wavelength than the light generated by the pump laser) through Raman scattering such that the emitted light has a different wavelength than the incoming light.

The remaining electrical signal can be passed from the lock-in amplifier 1124 to the rest of the computing device for analysis. Removing the light generated by the pump laser 1102 can allow the analyte estimation system 110 to accurately calculate the stimulated Raman gain. In some examples, the stimulated Raman gain can be calculated using a signal analysis system 1152. This method can allow noninvasive measurement of a variety of different analytes including but not limited to glucose, ethanol, lipids, hemoglobin, lactate, cortisol, and so on. In other examples, a spectrograph is not used.

Figure 12B:
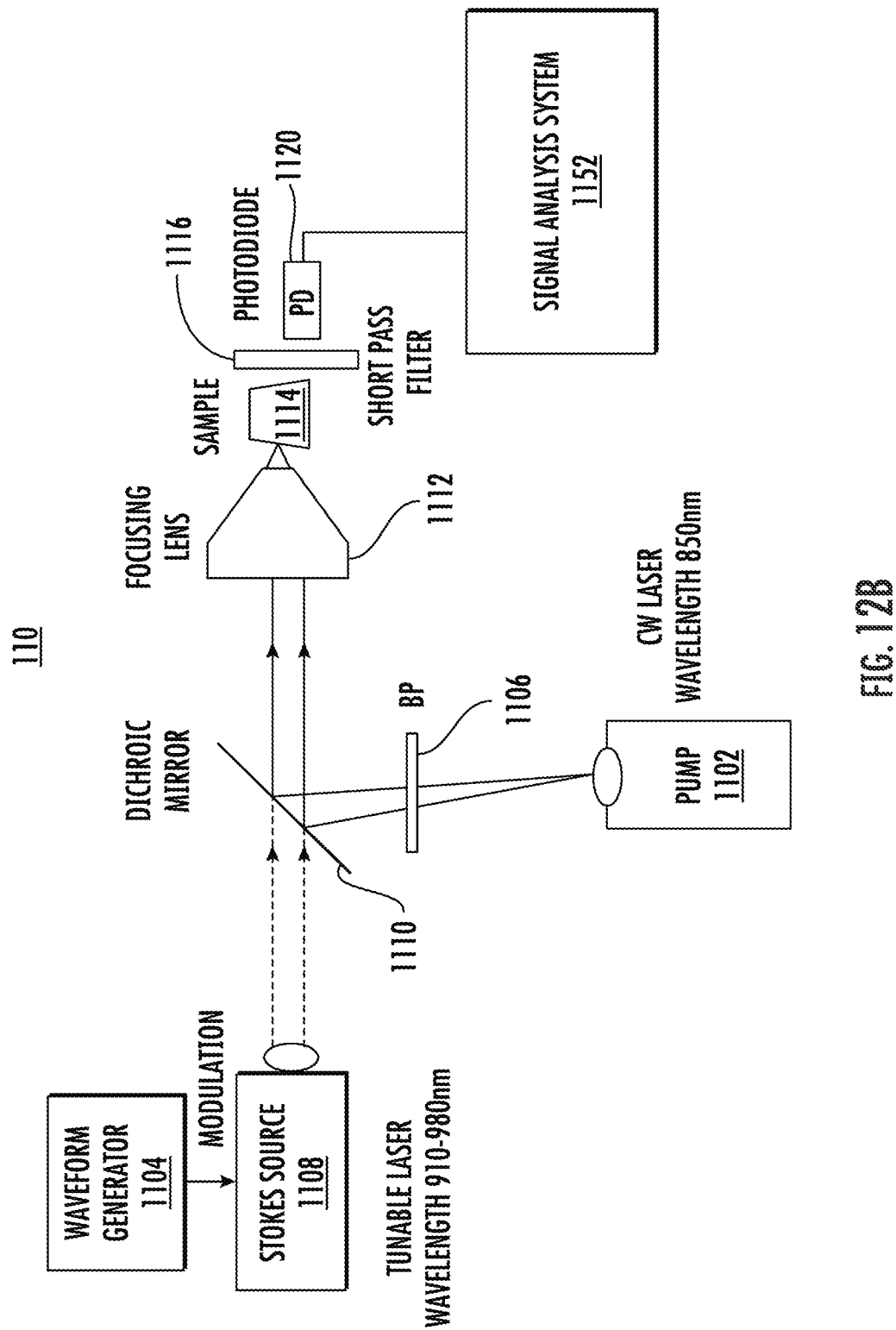

FIG. 12B represents an example analyte estimation system 110 in accordance with example embodiments of the present disclosure. In this example, the Stokes source 1108 is modulated, rather than the pump laser 1102. Similar to the configuration in FIG. 11A, the light from the pump laser 1102 and the modulated light from the Stokes source 1108 can pass through a dichroic mirror 1110 and a focusing lens 1112 into the sample material 1114.

In this configuration, the system includes a short pass filter 1150, which can filter out light with the second wavelength(s) (e.g., light from the Stokes source 1108) and allow light with the first wavelength from the pump laser 1102 to pass through.

The light detected by the photodiode 1120 can be used to generate an electrical signal. The electrical signal can be passed to a signal analysis system 1152 for analysis. The electrical signal is generated based on Rayleigh scattered light emitted from the target material. As noted above, the Rayleigh scattered light has the same wavelength as light generated by the pump laser 1102. As the Stokes source 1108 is modulated, the intensity of the Rayleigh scattered light can vary. In one specific example, if the amplitude of the Stokes source 1108 is at a low point (e.g., when the modulated amplitude reaches zero), the amount of Rayleigh scattered light emitted by the target material can reach a high intensity level (because less light is Raman scattered without the Stokes source 1108). Similarly, when the amplitude of the Stokes source 1108 reaches its high value during modulation, the intensity of Rayleigh scattered light emitted by the target material at the wavelength associated with the pump source 1102 may reach a low point (as more light is Raman scattered with the Stokes source 1108 being at peak intensity). The electrical signal that represents the intensity of light at the pump wavelength (because other wavelengths are filtered out by the short pass filter 1108) can be measured at the high point (e.g., when the intensity of the Rayleigh scattered light is at its maximum) and at the low point (e.g., when the intensity of the Rayleigh scattered light is at its minimum).

The difference in the electric signal between the high point and the low point can be measured by the signal analysis system 1152 to determine the amount of light that is Raman scattered. This amount can be referred to as the stimulated Raman loss (SRL). The stimulated Raman loss can represent the amount of light that, after exciting a molecule to a higher energy level in the target tissue, was emitted with a different wavelength.

Figure 13:
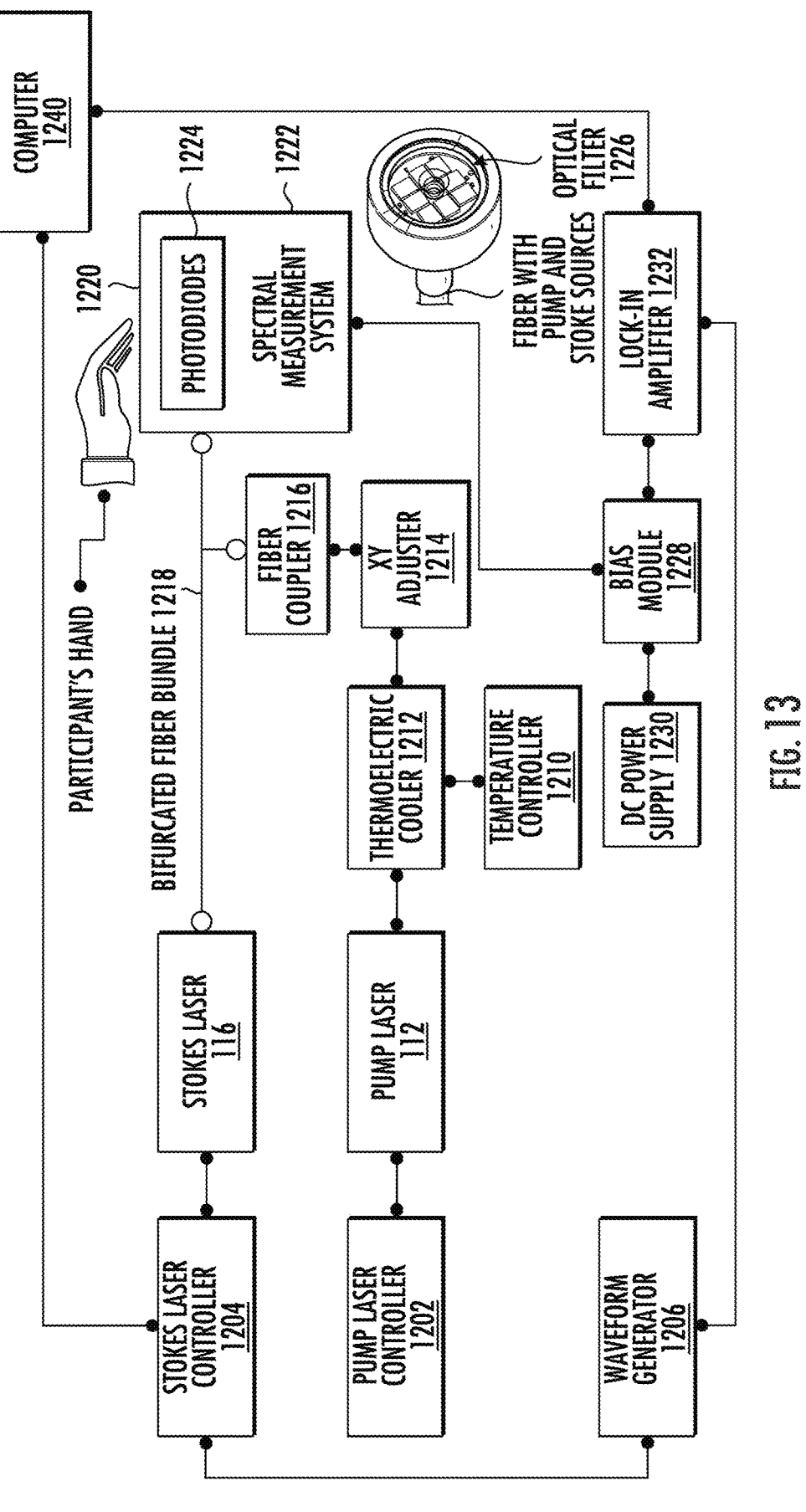
FIG. 13 illustrates an example system for non-invasively measuring molecules within a user's body in accordance with example embodiments of the present disclosure.

FIG. 13 illustrates an example system for non-invasively measuring analytes within a user's body in accordance with some example embodiments of the present disclosure. In accordance with example embodiments of the present disclosure. In this example, the analyte estimation system 110 can include two light sources. The first light source can be a pump laser 112 that can generate light with a first wavelength. The second light source can be one or more Stokes lasers 116. In FIG. 12, the Stokes laser 116 can be a single tunable laser that can generate a narrowband of light around any wavelength in a range of wavelengths. In another example, the Stokes lasers 116 can include a plurality of different laser diodes that each generate light at a particular wavelength and can be selectively turned on and off as needed during the detection process.

A pump laser controller 1202 can be associated with a pump laser 112. The pump laser controller 1202 can determine when the pump laser 112 is turned on and how long it remains on. A Stokes laser controller 1204 can be associated with the Stokes laser 116 and can control when the Stokes laser is 1204 turned on and, if the Stokes laser 116 is a tunable laser, what wavelength of light the Stokes laser 116 is outputting at any particular time.

A waveform generator 1206 can generate a waveform that is provided to the Stokes laser controller 1204. This waveform can be used to modulate the light produced by the Stokes laser 116. Modulating the output of the Stokes laser 116 can ensure that the light emitted by the Stokes laser 116 and the light emitted by the pump laser 112 can be separated from one another at a later point in the process.

A temperature controller 1210 can control a thermoelectric cooler 1212. The thermoelectric cooler 1212 can adjust the output of the pump laser 112 as directed by the temperature controller 1210. An XY adjuster 1214 can control the direction of the light emitted by the pump laser 112 and allow a fiber coupler 1216 to provide the light generated by the pump laser 112 into a bifurcated fiber bundle associated with the Stokes laser 116.

The light combined in the bifurcated fiber bundle 1218 can be projected towards the target sample 1220 which in this case is a participant's hand. The light can be emitted from the participant's hand towards a spectral measurement system 1222. The spectral measurement system 1222 can include one or more photodiodes 1224. In some examples, the photodiodes 1224 have an associated optical filter 1226. The optical filter 1226 can remove wavelengths of light that are not needed by the spectral measurement system 1222. The output of the spectral measurement system 1222 is provided to a bias module 1228. The biased module has a DC power supply 1230. A lock-in amplifier 1232 can remove modulated light such that the unmodulated light can be isolated and analyzed.

The output of the lock-in amplifier can be provided to a computer 1240. The computer 1240 can analyze the data to determine the presence or absence of molecules of interest in the target tissue which is, in this case, the participant's hand.

Figure 14:
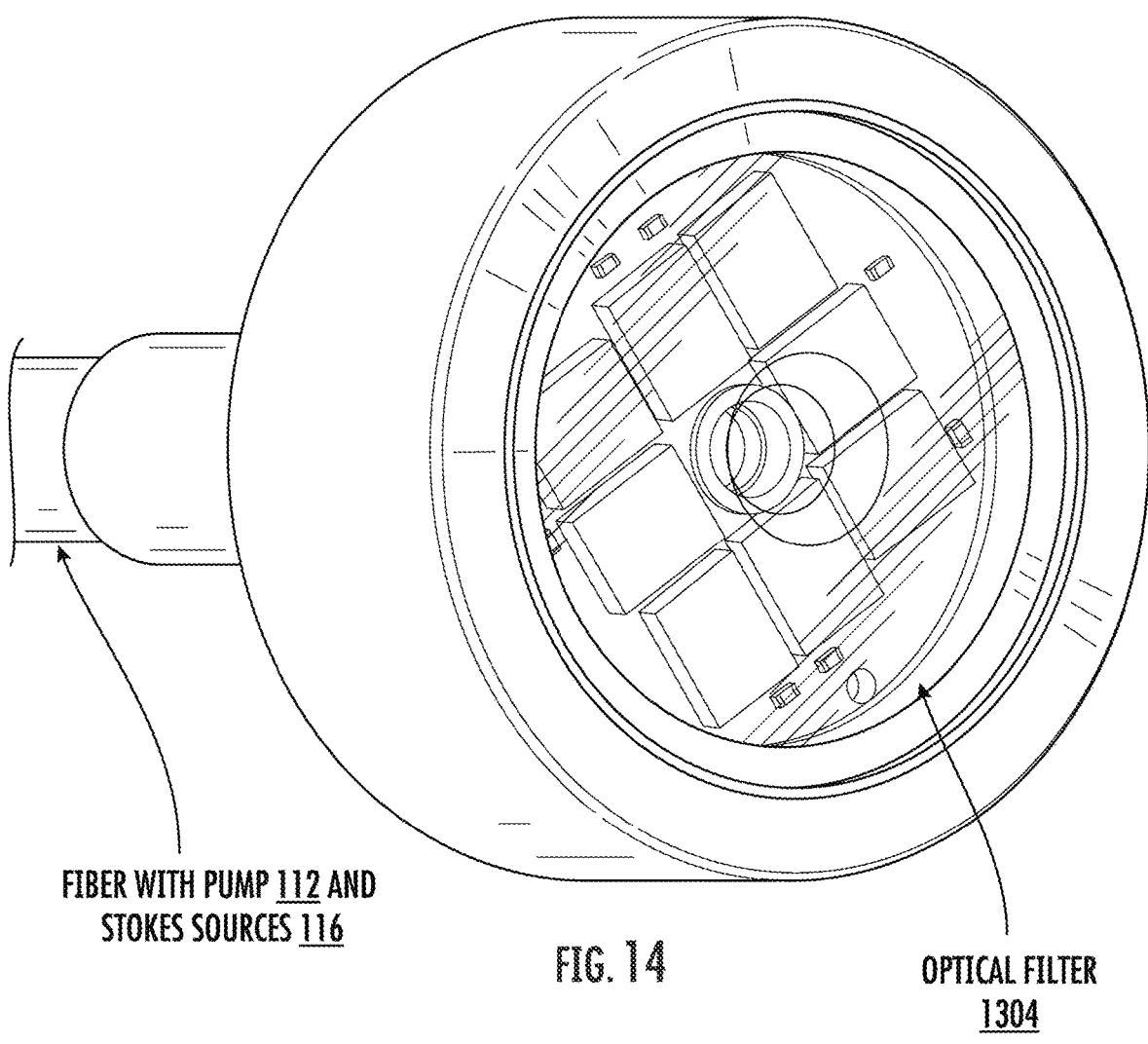
FIG. 14 illustrates an example system with light sources and photodiodes in accordance with example embodiments of the disclosure.

FIG. 14 illustrates an example system with light sources and photodiodes in accordance with example embodiments of the disclosure. As can be seen, the two light sources can include a pump laser 112 and a Stokes laser 116 that are positioned to project light through a fiber 1302 in a detecting unit. The light passes forward through the opening into the skin of a user. The skin of a user can emit light towards the sensor unit. The sensing unit includes an optical filter 1304 that can filter out light of certain wavelengths. The plurality of photodiodes can then detect the emitted light that has not been filtered. Information gathered by the photodiodes can be transmitted back to a computing system to be analyzed to determine the contents of the tissue into which the light was projected.

Figure 15:
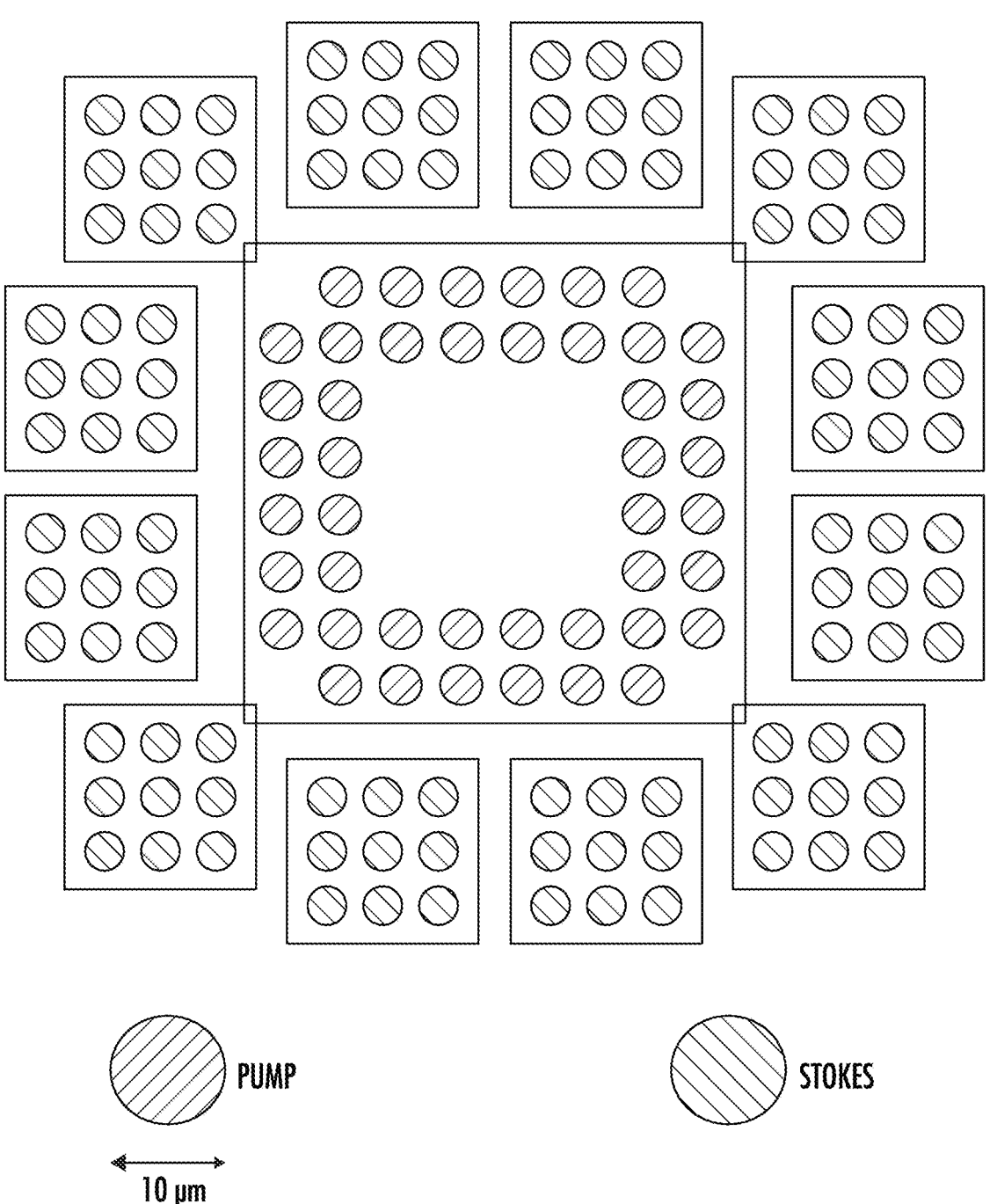
FIG. 15 illustrates a layout of a plurality of light-producing sources in accordance with example embodiments of the present disclosure.

FIG. 15 illustrates a layout of a plurality of light-producing sources in accordance with some example embodiments of the present disclosure. A plurality of pump lasers can be centered in the middle providing light at a consistent wavelength. A pump laser and one or more Stokes lasers can be arranged in a pattern such that the Stokes lasers provide a plurality of different wavelengths of light. In some examples, the wavelengths of light provided by the Stokes lasers are associated with molecules of interest.

Figure 16:
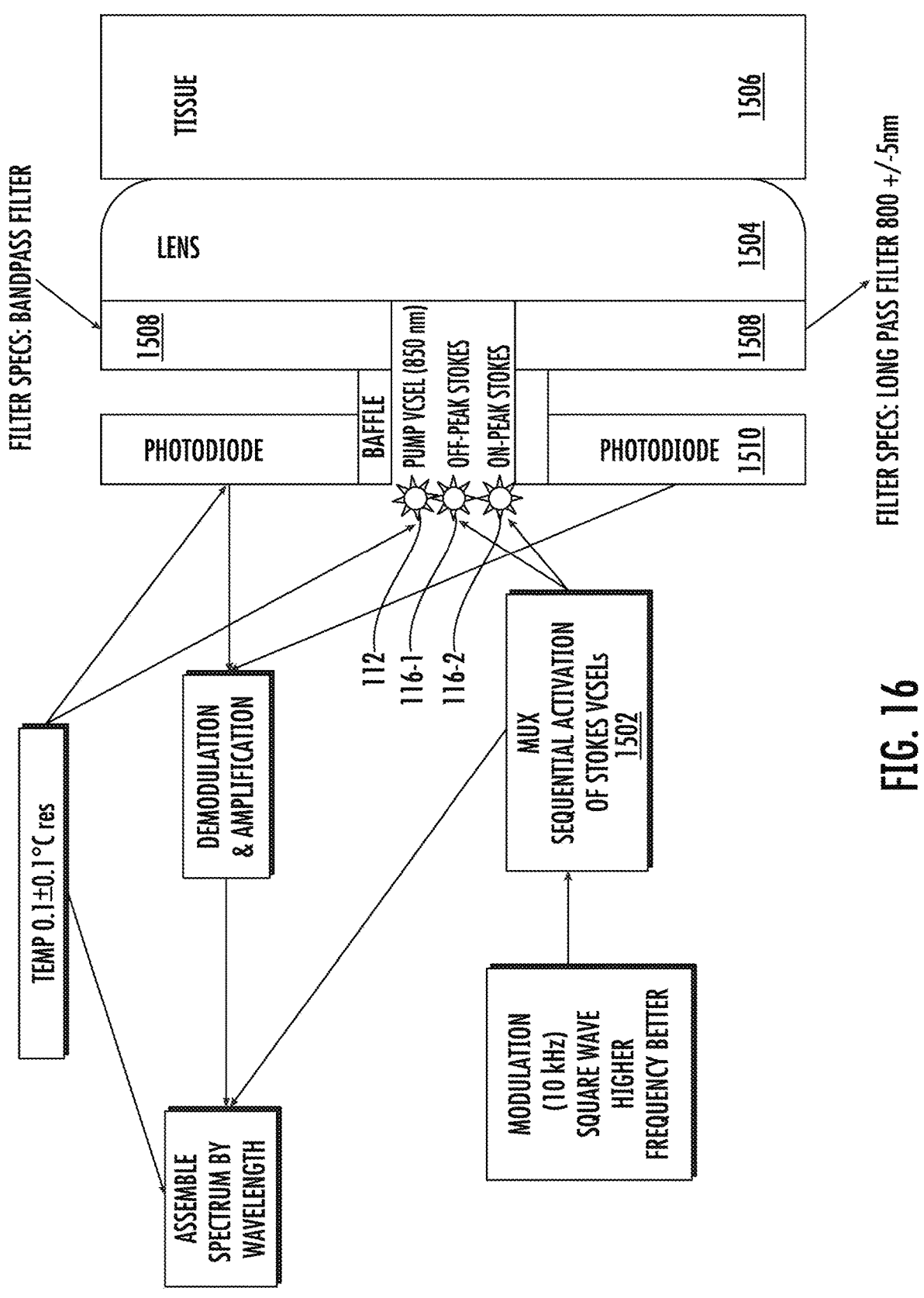
FIG. 16 illustrates an example analyte detection system in accordance with example embodiments of the present disclosure.

FIG. 16 illustrates an example analyte detection system 110 in accordance with some example embodiments of the present disclosure. The analyte estimation system 110 can include a pump laser 112 (e.g., a VCSEL) and two Stokes lasers 116 (e.g., an off-peak Stokes laser 116-1 and an on-peak Stokes laser 116-2). However, in other configurations, the Stokes laser 116 can include a plurality of Stokes lasers, each one configured to generate light with a particular wavelength. One or more outputs of the pump laser 112 and/or the Stokes lasers 116 may be modulated using a square wave at 10 kilohertz or higher. In general, a higher frequency is better when using modulation to distinguish light from different sources. A multiplexer (MUX) 1502 can be used to sequentially activate the two or more Stokes lasers 116.

Thus, the pump laser 112 consistently produces light at 850 millimeters and the two or more Stokes lasers 116 can be sequentially activated to produce light with a narrowband centered around specific wavelengths. The light from the pump lasers 112 and two or more Stokes lasers 116 are projected forward through a focusing lens 1504 to the tissue of a user 1506. The tissue of a user can emit light that passes through one or more filters 1508. For example, the light can pass through a bandpass filter 1508 that restricts the light that passes through to a predefined band of wavelengths or a long pass filter that filters out one or more wavelengths of light.

Once the light has passed through the filters, one or more photodiodes 1510 can detect the light (e.g., detecting the intensity of light with a particular wavelength or the number of photons with a particular wavelength). The photodiodes can generate electrical signals based on the interaction of photons with the photodiode 1510. The electrical signals can be demodulated, amplified, and transmitted to the computing device that can assemble an entire spectrum of light by wavelength. The spectrum can be analyzed to determine, based on the amounts of light at various points in the spectrum (e.g., the Raman signature), whether one or more analytes are present in the tissue of the user. As noted above, if a plurality of laser diodes are simultaneously activated and provide light at a respective plurality of Stokes frequencies, each laser diode can be modulated at a different respective frequency. The resulting signal can be analyzed using a Fourier transform (e.g., fast Fourier transform) to determine the intensity of light at each different wavelength.

FIG. 17 is a flowchart depicting an example process of detecting molecules within a target in accordance with example embodiments of the present disclosure. One or more portion(s) of the method can be implemented by one or more computing devices such as, for example, the computing devices described herein. Moreover, one or more portion(s) of the method can be implemented as an algorithm on the hardware components of the device(s) described herein. FIG. 17 depicts elements performed in a particular order for purposes of illustration and discussion. Those of ordinary skill in the art, using the disclosures provided herein, will understand that the elements of any of the methods discussed herein can be adapted, rearranged, expanded, omitted, combined, and/or modified in various ways without deviating from the scope of the present disclosure. The method can be implemented by one or more computing devices, such as one or more of the computing devices depicted in FIGS. 1, 11-14.

The computing device can project light from a first light source and a second light source towards a portion of a user's body. The first light source can project, at 1714, light with the first wavelength, and the one or more second light sources can generate light with a second wavelength. The light sources (e.g., lasers) can project the generated light onto the skin of a user. The light can interact with molecules in the skin. The molecules in the skin can emit light to the system. In some examples, the light is Raman scattered by interacting with the molecules in the user's skin.

The computing device can detect, at 1716, using a photodiode, an intensity of emitted light with a particular wavelength. For example, the photodiode can measure the intensity of light in the second wavelength. The computing device can, at 1718, determine, based on the emitted light, a concentration of each of a plurality of molecules in a user's body.

The computing device can generate, at 1724, based on the concentration of each of the plurality of molecules in the user's body, a user profile. For example, the computing device can determine the relative concentrations of hemoglobin, glucose, lipids, and so on in a particular user's body based on information from the photodiodes. This information can be compiled into a standard user profile format.

In some examples, with the user's permission, the computing device can access locally stored user profiles or user profiles available via a computer network. The computing system can compare, at 1726, the user profile to a plurality of stored user profiles to identify the user. For example, the specific concentrations of various molecules and chemicals in the user's body can serve as a fingerprint to uniquely identify each user. However, in consideration of user privacy, no profile will be generated and no comparison be done unless the user has consented.

In some examples, once the system has determined the identity of the user based on the matching user profile, the computer system can access data associated with the user account and provide that information and services to the user.

Figure 18:
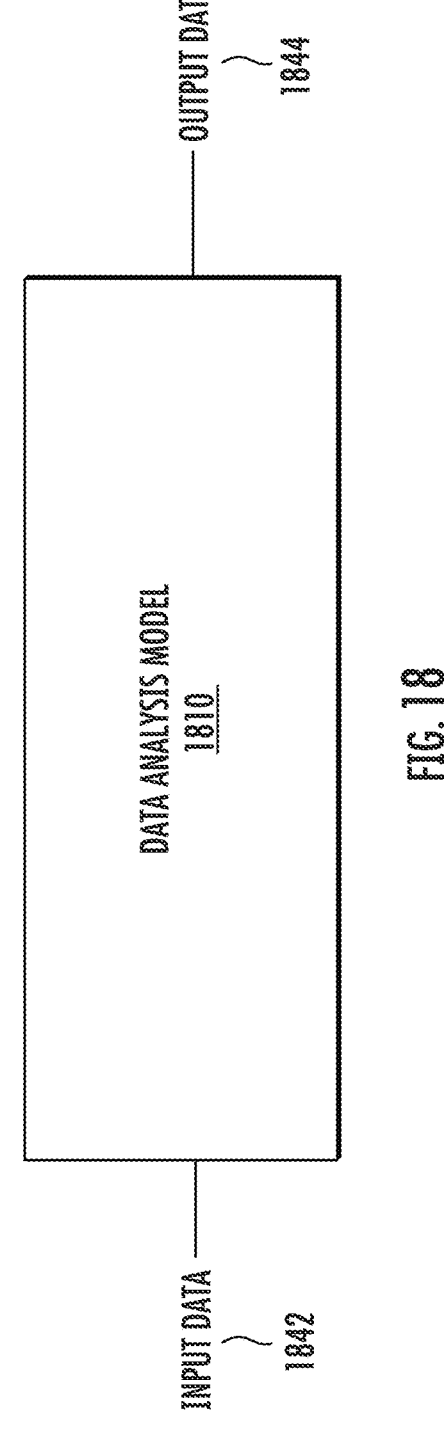
FIG. 18 depicts a block diagram of an example data analysis model according to example embodiments of the present disclosure.

FIG. 18 depicts a block diagram of an example data analysis model 1810 according to example embodiments of the present disclosure. A machine-learned data analysis model can take information about the intensity of late at a variety of wavelengths as input 1842. For example, the data analysis model 1810 can identify the values at the expected wavelengths for glucose. Once trained, the machine-learned data analysis model can achieve a good accuracy of R2=0.84, which corresponds to approximately 30 mg/dl mean absolute error. Thus, data analysis model 1810 can output 1844 information describing whether a particular analyte is present and in what concentration.

In some examples, glucose concentrations found in human blood (<300 mg/dl, usually <140 mg/dl), result in glucose peaks that are not easily separable from the background, since the Raman signal is very weak. The model picks up the important features which align with some of the expected Raman peaks of Glucose at wavenumbers 514, 1060, 1025, 1366 cm$^{-1}$, which can be clearly visible for the spectrum measured for very high Glucose concentration (>5000 mg/dl). This model can then be used to predict the glucose level for 200 new measurements with an R2 of 0.84. This corresponds to approximately 30 mg/dl mean absolute error.

In some examples, the machine-learned data analysis model 1810 can otherwise include various machine-learned models such as neural networks (e.g., deep neural networks), other types of machine-learned models, including non-linear models, and/or linear models, or binary classifiers. Neural networks can include feed-forward neural networks, recurrent neural networks (e.g., long short-term memory recurrent neural networks), convolutional neural networks, or other forms of neural networks.

A variety of training techniques can be used to train the machine-learned data analysis model 1810. Specifically, the machine-learned data analysis model 1810 can be trained using one of a plurality of semi-supervised training techniques. The machine-learned data analysis model 1810 can also be trained using a supervised training technique, such as, for example, backward propagation of errors. For example, a loss function can be backpropagated through the model(s) to update one or more parameters of the model(s) (e.g., based on a gradient of the loss function). Various loss functions can be used such as mean squared error, likelihood loss, cross-entropy loss, hinge loss, and/or various other loss functions. Gradient descent techniques can be used to iteratively update the parameters over several training iterations. In some implementations, performing backward propagation of errors can include performing truncated backpropagation through time. Generalization techniques (e.g., weight decays, dropouts, etc.) can be performed to improve the generalization capability of the models being trained.

Figure 19:
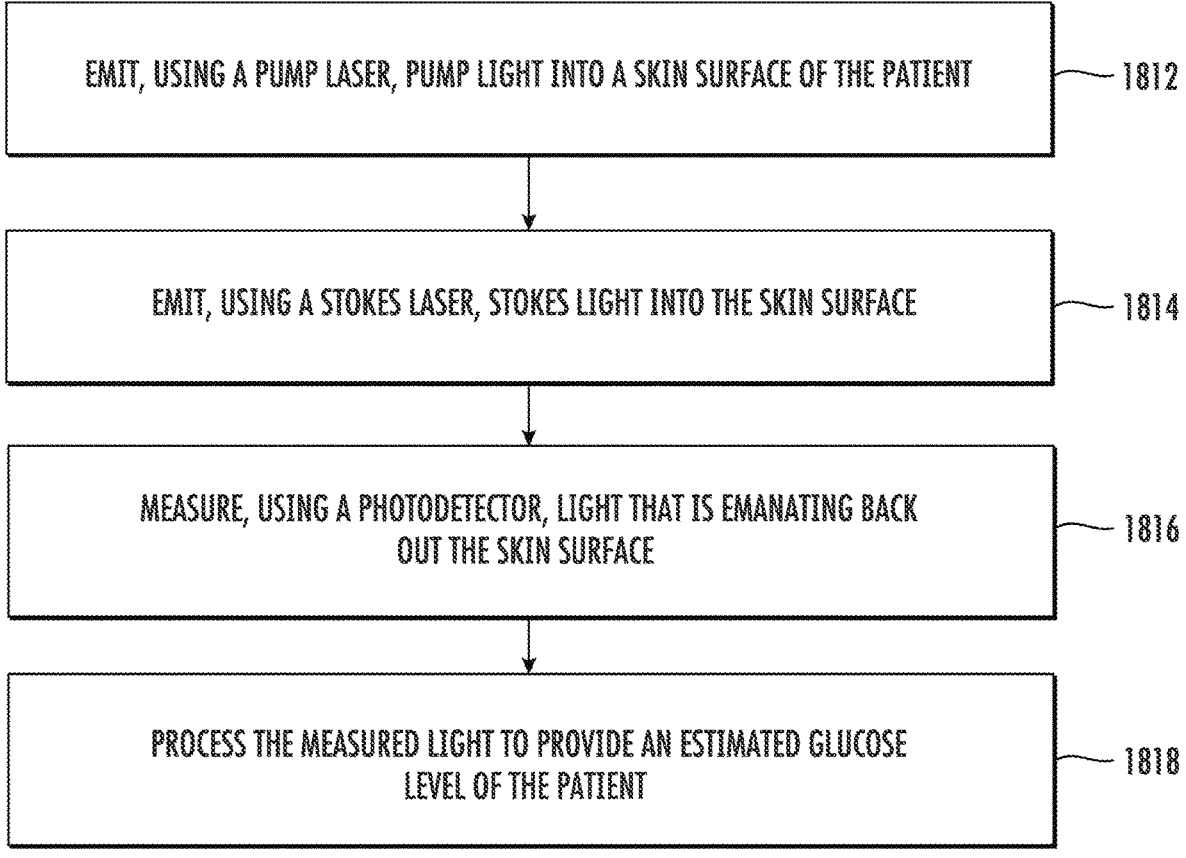
FIG. 19 is a flowchart depicting an example process of detecting analytes within a target tissue in accordance with example embodiments of the present disclosure.

FIG. 19 is a flowchart depicting an example process of detecting analytes within a target tissue in accordance with example embodiments of the present disclosure. One or more portion(s) of the method can be implemented by one or more computing devices such as, for example, the computing devices described herein. Moreover, one or more portion(s) of the method can be implemented as an algorithm on the hardware components of the device(s) described herein. FIG. 19 depicts elements performed in a particular order for purposes of illustration and discussion. Those of ordinary skill in the art, using the disclosures provided herein, will understand that the elements of any of the methods discussed herein can be adapted, rearranged, expanded, omitted, combined, and/or modified in various ways without deviating from the scope of the present disclosure. The method can be implemented by one or more computing devices, such as one or more of the computing devices depicted in FIGS. 1, 11-14.

A computing device for non-invasively measuring glucose levels in a user using Stimulated Raman Scattering can comprise a Ramp pump laser, a Stokes laser, and a photodetector. The computing device can, at 1812, using a pump laser emit pump light into a skin surface of the user, the pump light being at a fixed wavelength. It should be noted that while the light can be directed towards the surface of the skin, the light can be focused at a subdermal area of the user such that the light is more likely to interact with the molecules in the blood of a user. Thus, when the present disclosure indicates that light is directed to or received from the surface of the skin of a user, the target of the light can be below the surface of the skin of the user. The computing device can, at 1814, using a Stokes laser, emit Stokes light into the skin surface at a plurality of Stokes wavelengths within a window of Raman measurement wavelengths.

The Stokes source can comprise a variable wavelength narrowband laser swept continuously from one end to the other end of the window of Raman measurement wavelengths during said non-invasive glucose measuring. In some examples, the Stokes source can comprise a plurality of fixed-wavelength narrowband laser sources, each having a different center wavelength lying within the window of Raman measurement wavelengths.

In some examples, the Raman pump source and the fixed-wavelength narrowband laser sources of the Stokes source are VCSELs, and wherein no optical fibers or mirrors are used anywhere in the device. The computing device can, at 1816 and using a photodetector, measure light that is emanating back out the skin surface.

In some examples, the photodetector can detect light across a range of wavelengths including both said Raman pump source wavelength and said window of Raman measurement wavelengths, and wherein time modulation of Raman pump source, time modulation of said Stokes source, and/or different time modulations of both said Raman pump source and said Stokes source are used to allow differentiation of Raman pump wavelength light from the light having the wavelengths lying within the window of Raman measurement wavelengths.

In some examples, the photodetector is a photodiode that detects light across the entire window of Raman measurement wavelengths, and wherein the plurality of fixed-wavelength narrowband laser sources are activated one-at-a-time during said non-invasive glucose measuring.

The computing device can, at 1818, process the measured light to provide an estimated glucose level of the user. In some examples, the Stokes source emits light that is narrowband relative to said window of Raman measurement wavelengths, wherein said Stokes light comprises a plurality of emissions of said narrowband light at a respective plurality of center wavelengths ranging across said window of Raman measurement wavelengths.

Figure 20:
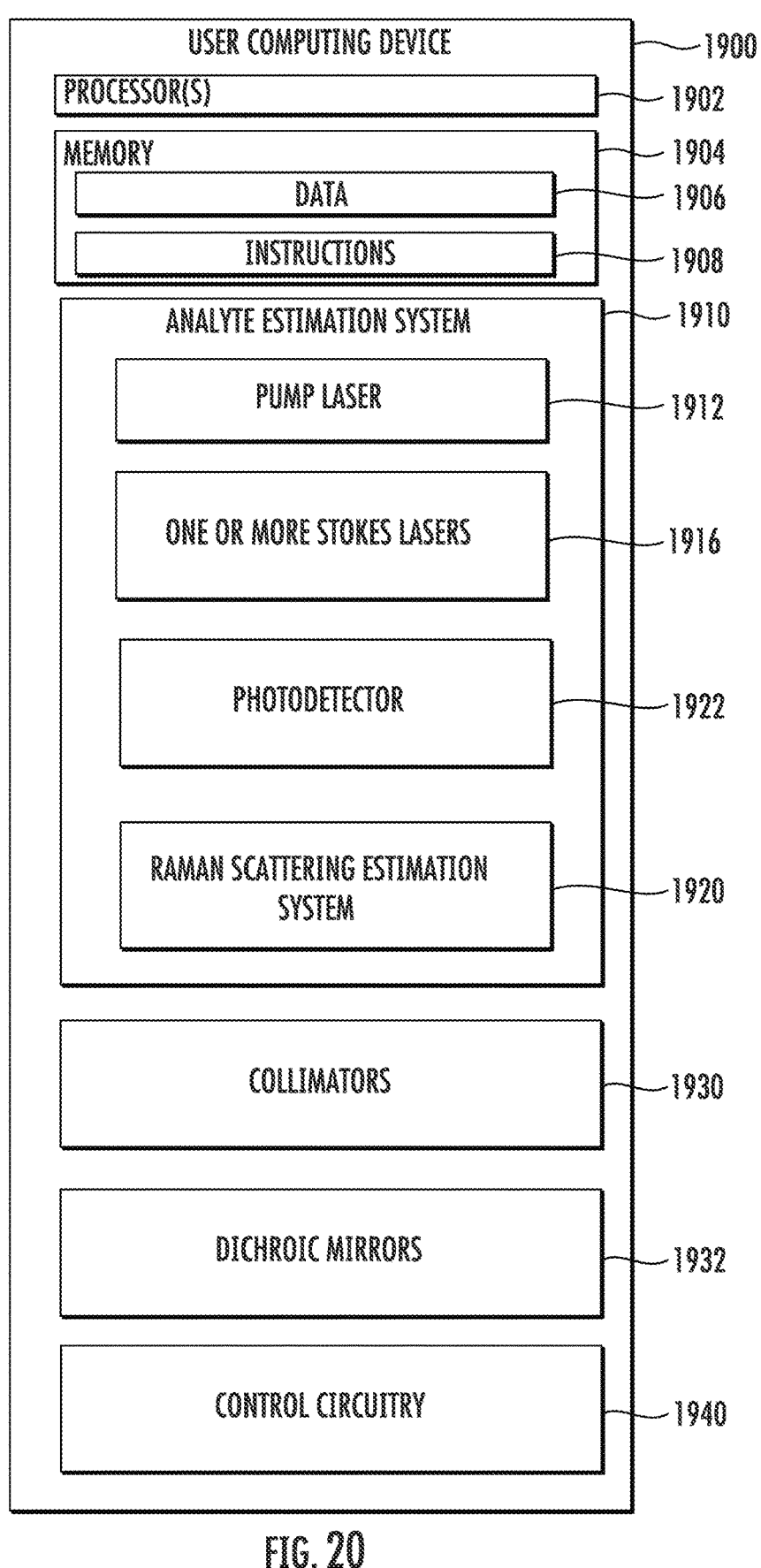
FIG. 20 illustrates an example computing environment including a user computing device in accordance with example embodiments of the present disclosure.

FIG. 20 illustrates an example computing environment including a user computing device 1900 in accordance with example embodiments of the present disclosure. The computing device 1900 can include an analyte estimation system 1910 for non-invasively determining the presence and amount of one or more analytes internal to a user. In some examples, the computing device 1900 can be a user computing device such as a smartphone or a wearable computing device. In other examples, the computing device 1900 can be a computing device intended for home use and not for portability. In this example, the user computing device 1900 can include one or more processors 1902, memory 1904, an analyte estimation system 1910, one or more collimators 1930, and control circuitry 1940.

In more detail, the one or more processors 1902 can be any suitable processing device for a computing device 1900. For example, such a processor can include one or more of: one or more processor cores, a microprocessor, an ASIC, an FPGA, a controller, a microcontroller, etc. The one or more processors can be one processor or a plurality of processors that are operatively connected. The memory 1904 can include one or more non-transitory computer-readable storage media, such as RAM, ROM, EEPROM, EPROM, flash memory devices, etc., and combinations thereof.

In particular, in some devices, memory 1904 can store instructions 1908 for implementing the analyte estimation system 1910. It will be appreciated that the term "system" can refer to specialized hardware, computer logic that executes on a more general processor, or some combination thereof. Thus, a system can be implemented in hardware, application-specific circuits, firmware, and/or software controlling a general-purpose processor. In one embodiment, the system can be implemented as program code files stored on the storage device, loaded into memory, and executed by a processor or can be provided from computer program products, for example, computer-executable instructions, that are stored in a tangible computer-readable storage medium such as RAM, hard disk or optical or magnetic media.

Memory 1904 can also include data 1906 that can be retrieved, manipulated, created, or stored by the one or more processor(s) 1902. In some example embodiments, such data can be accessed and used as input to the analyte estimation system 1920. In some examples, the memory 1904 can include data used to perform one or more processes and instructions that describe how those processes can be performed.

In some examples, the analyte estimation system 1920 can include a pump laser 1912, one or more Stokes lasers 1916, a photodetector 1922, and a Raman scattering estimation system 1910. Although not pictured, the analyte estimation system 1920 can also include an optical filter and one or more optical lenses (e.g., micro lenses) to focus the lasers on the same area (e.g., the same portion of the user's skin). The pump laser 1912 (e.g., a first light source) can be a laser diode that emits light (e.g., a stream of photons) at the target wavelength. In some examples, the pump laser can produce light with an average wavelength of 780 nanometers. Other wavelengths of a pump laser 1912 may be used, with the wavelengths of the one or more Stokes lasers 1916 being determined based, at least in part, on the wavelength of the pump laser 1912. In some examples, the pump laser 1912 can be a vertical-cavity surface-emitting laser (VC-SEL) included in a semiconductor chip. In some examples, the wavelength of the light emitted by the pump laser 1912 is 850 nanometers. Other wavelengths can be used.

The pump laser 1912 can be control by control circuitry which can send signals to engage or turn off the pump laser in accordance with at least one duty cycle. In some examples, the pump laser 1912 can be pulse modulated. Pulse modulating the pump laser 1912 can include controlling the pump laser 1912 to generate square wave pulses.

The pump laser 1912 can include (or be associated with) a modulation system. The modulation system can, in coordination with the control circuitry, be used to modulate the light produced by the pump laser 1912. The pump laser can be referred to as a first light source. By modulating the light produced by the pump laser 1912, the analyte estimation system 1920 can differentiate (e.g., using a filter or lock-in amplifier) between light that the target material emits after being excited by the light that originated from the pump laser 1912 and the light that the target material emits after being excited by light that originates from the one or more Stokes lasers 1916.

The one or more Stokes lasers 1916 can include a tunable laser that can produce light with a wavelength within a predetermined range as needed. Thus, the tunable laser can be adjusted such that the wavelength of the light produced by the light source can change within a range. For example, in some examples, the tunable laser can be adjusted to emit light with a wavelength that can vary from 910 nanometers to 980 nanometers. In some examples, the wavelength of the light produced by the tunable laser can be determined based on the Raman signature of a particular analyte that the analyte estimation system 1920 is trying to identify. In some examples, both the pump laser and the one or more Stokes lasers can use about 40 milliwatts of power to operate.

The one or more Stokes lasers 1916 can be control by control circuitry which can send signals to engage or turn off the pump laser in accordance with at least one duty cycle. In some examples, the one or more Stokes lasers 1916 can be pulse modulated. Pulse modulating the pump laser 1912 can include controlling the one or more Stokes lasers 1916 to generate square wave pulses.

In some examples, the one or more Stokes lasers can include a modulation system. Thus, in some configurations, the pump laser 1912 can be modulated to distinguish the light produced by the pump laser 1912 from the light produced by the one or more Stokes lasers 1916. In other examples, the one or more Stokes lasers 1916 are modulated to distinguish between the two light sources.

In some examples, the one or more Stokes lasers 1916 can provide light with a wavelength tuned to the Raman signature of a particular analyte that the analyte estimation system 1920 is trying to identify (e.g., glucose). By providing additional light (e.g., a stream of photons) with a wavelength determined based on the Raman signature of the analyte, the analyte estimation system 1920 can enable stimulated Raman scattering to occur. Stimulated Raman scattering can result in the light provided by the one or more Stokes lasers 1916 stimulating more Raman scattering than would be expected without the additional light provided by the one more Stokes lasers 1916. Thus, introducing the light provided by the one or more Stokes lasers 1916 can increase the detectability of a particular analyte in the sample material because the probability of Raman scattering is increased.

In some examples, the analyte estimation system 1920 can include a photodetector 1922. The photodetector 1922 can be a sensor (e.g., a semiconductor device that converts light (e.g., photons) into electrical current) such as a photodiode. The photodiode can be configured to detect light over a range of wavelengths. In some example embodiments, light can be optically filtered such that only light within a specific wavelength range is detected by the photodetector. An amount of light can also be understood to be the number of photons detected and/or the intensity of the light measured at a particular wavelength.

In some examples, a filter can be employed to remove target-emitted light that is associated with the one or more Stokes lasers 1916 such that only light originating from the pump laser 1912 is detected. Similarly, an optical filter can filter out light with a wavelength associated with the pump laser 1912 such that only target-emitted light that results from the Stokes lasers 1916 or Raman scattering is detected by the photodetector. In some examples, a filter (or a lock-in amplifier) can remove modulated light, if the one or more Stokes lasers 1916 were modulated, or unmodulated light, if the pump laser 1912 was modulated.

The Raman analyte estimation system 1910 can be used to detect the amount of light (e.g., the intensity of the light or the number of photons) generated by Raman scattering associated with an analyte in the sample material. In some examples, the Raman scattering estimation system 1910 can determine the amount of light (e.g., either the number of photons or the intensity of the light) that has been Raman scattered to identify an analyte in the target material. In a first example, the user computing device can determine the amount of light at the pump wavelength (e.g., a first wavelength) that is lost (stimulated Raman loss). Alternatively, the user computing device can determine the amount of light at the Stokes associated wavelength that is gained (e.g., stimulated Raman gain). Either measurement or their combination can be used to estimate the amount of a particular analyte in the target material (e.g., a user's skin). A detected Stokes range can be compared to a reference spectrum to noninvasively measure the presence or absence of a target analyte.

For example, the sample material can be a portion of a user's body. The analyte can be, for example, glucose. Based on the amount of light having the predetermined second wavelength, the analyte estimation system 1910 can estimate the amount of the analyte in the target sample. In some examples, the estimated amount of the analyte can be presented for display to a user.

In some examples, the user computing device 1900 can include one or more collimators 1930. The collimators can be used, along with mirrors (e.g., dichroic mirrors 1932) to cause the light from the Pump lasers 1912 and the one or more stokes lasers 1916 to be made to be collinear such that the beams do not diverge (or diverge less). Using one or more collimators 1930 can enable the user computing device 1900 to focus the laser beams on a portion of target tissue that is smaller than would otherwise be possible. Focusing the light on a small area (e.g., less than 10 microns in diameter results in an increase in power density of the light. Power density in this context can be measured based on the amount of light projected per unit of area over which the light is projected. Thus, focusing the light on a smaller area can result in a higher power density without needing to increase the total amount of projected light.

The user computing device 1900 can include one or more dichroic mirrors 1932. A dichroic mirror 1932 can be configured such that light at one or more frequencies are reflected off the dichroic mirror 1932. In addition, light at one or more other frequencies can pass through the dichroic mirror 1932 without being affected. Thus, dichroic mirrors 1932 can be used to combine light from two or more light sources (e.g., a pump laser 1912 and the one or more stokes lasers 1916) into a single light beam. Combining light from multiple light sources can result in the light being more densely focused such that it is targeted on a relatively small area, increasing the power density of the light.

The user computing device 1900 can include control circuitry 1940. The control circuitry 1940 can be used to increase the amount of light projected into the area of the target tissue (e.g., the power density of the light). Specifically, the control circuitry can be used to turn the light sources on and off in accordance with a duty cycle. By turning the light sources on and off the light sources can be operated at a higher power level than would be possible if the light sources were operated continuously. Specifically, operating the light sources for short durations but higher power can result in higher power density during the periods in which the light sources are turned on without exceeding the maximum permissible exposure for the light sources. The maximum permissible exposure limit can describe the maximum amount of light (or other electromagnetic radiation) that tissue (or other material) can be exposed to without hazardous effects or biological changes. The maximum permissible exposure can be determined by the wavelength of the light, the energy of the light, and the duration of exposure.

Thus, by pulse modulating the light sources, the control circuitry 1940 can reduce the duration of exposure and allow higher power (energy of the light) to be used during the times in which the light sources are turned on. The control circuitry 1940 can be configured such that it turns on one or more of the light sources during particular periods of time and turns them off during other periods of time. By only having the light source active for a portion of the total time, the control circuitry 1940 can ensure that the power usage of the system remains low and that the amount of light to which the tissue is exposed does not exceed the predetermined exposure limits for any of the light sources.

The control circuitry 1940 can operate the light sources (e.g., the Raman light source and the Stokes light source) according to at least one duty schedule. For example, the control circuitry can control the light sources such that they are activated in accordance with a 1% duty cycle. Thus, the light sources can be engaged for 10 nanoseconds followed by 990 nanoseconds in which the light sources were not engaged. By only engaging the light sources for a small fraction of time, the light sources can have a higher power (when engaged) than would be possible if the light sources were engaged continuously. Thus, during the time in which the light sources are engaged, the analyte detection system can have a high accuracy while remaining within the exposure limits.

In some examples, different light sources can have different duty cycles. For example, the control circuitry 1940 can pulse modulate one or more Stokes sources at 10 Mhz and pulse module the pump source at 5 MHz. In this way, the stokes signal spectrum can have a center frequency at 10 MHz and the pump signal spectrum can have a center frequency at 5 MHz. Having a first center frequency for the one or more Stokes sources and a second center frequency for the pump signal spectrum can allow the analyte estimation system to distinguish more easily between the two using signal processing.

Figure 21:
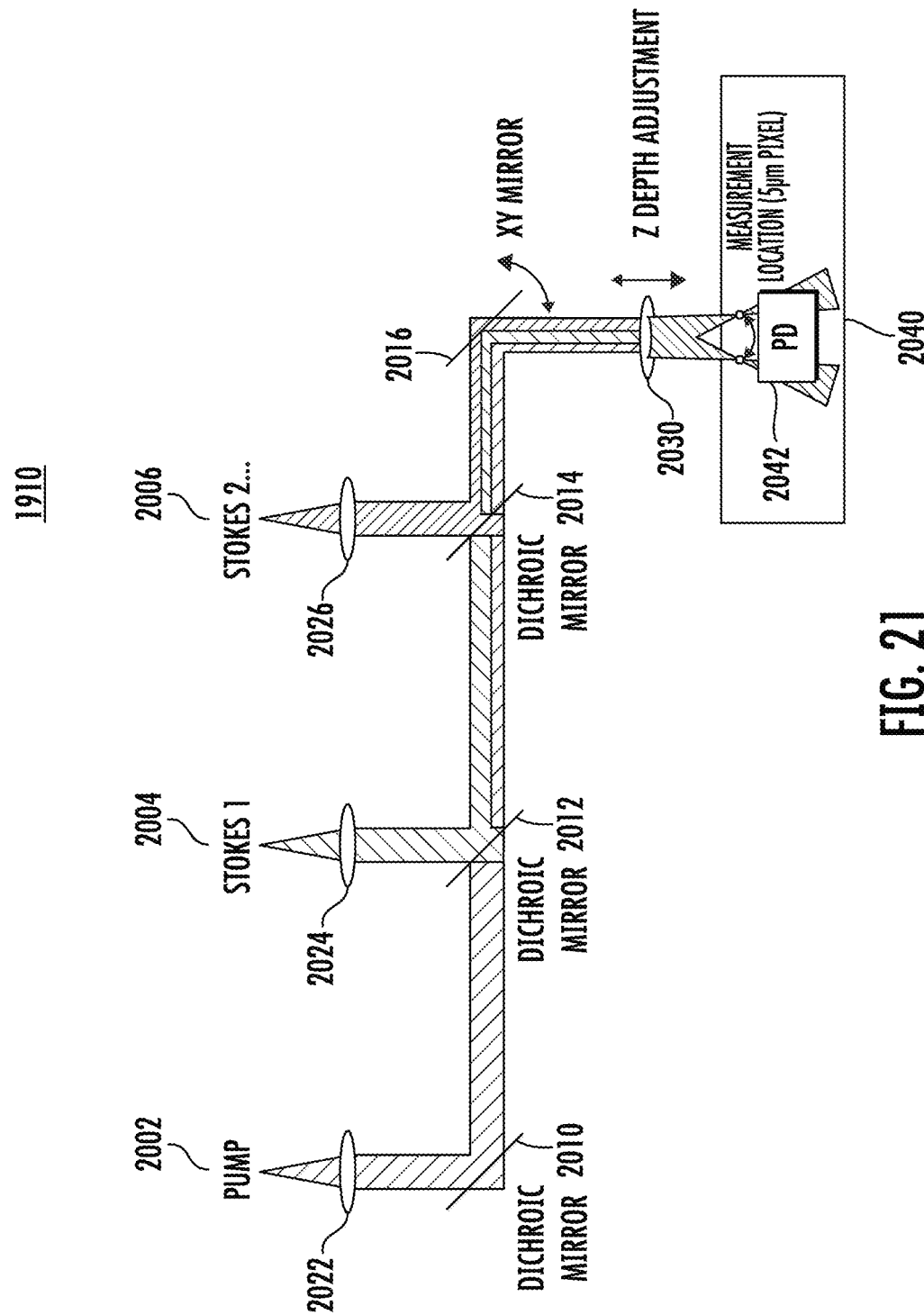
FIG. 21 is a diagram illustrating the effect of polarity in generated light in accordance with example embodiments of the present disclosure.

FIG. 21 is a diagram of an analyte detection system that causes light from different sources to be collinear in accordance with example embodiments of the present disclosure. In some examples, an analyte detection system 1910 can include a pump source 2002, a first stokes source 2004, and a second stokes source 2006. In order to ensure that the light from all three sources combines into one light stream such that the light from all three sources is effectively focused on the same area of the target tissue the analyte detection system 1910 includes a plurality of dichroic mirrors and collimators. These components can be used to combine the light from each light source into a combined light stream. Thus, light from pump source 2002 can be directed towards a first dichroic mirror 2010. This dichroic mirror 2010 can be configured such that light at the frequency of the pump source 2002 reflects off the mirror 2010. The dichroic mirror 2010 can be configured such that it directs the reflected light towards a second dichroic mirror 2012. The second dichroic mirror 2012 can be configured to allow the light from the pump source 2002 to pass through without altering its trajectory.

The first Stokes source 2004 can project light towards the second dichroic mirror 2012. The second dichroic mirror 2012 can be configured such that light with the frequency associated with the first Stokes source 2004 reflects off the dichroic mirror 2004 towards the third Stokes source 2016 but light with a frequency associated with the pump source passes through the dichroic mirror and joins into the beam of the light projected from the first Stokes source 2004. The light from the first Stokes source 2004 can be reflected into the same path as the light from the pump source 2002. The light from the pump source 2002 and the first Stokes source can be effectively combined into a single light stream.

The combined light stream can be directed towards a third dichroic mirror 2014. The third dichroic mirror 2014 can be configured such that light with frequencies associated with both the pump source 2002 and the first Stokes source 2004 pass through unaltered. Light from the second Stokes 2006 source is directed towards the third dichroic mirror 2014. The third dichroic mirror 2014 is configured to reflect the light from the second Stokes source 2006 directing it along the same path as the combined light from the pump source 2002 and the first Stokes source. In this way, the light from the pump source 2002, the first stokes source 2004, and the second Stokes source 2006 can be effectively combined into a single stream that is now collinear. The analyte estimation system 1910 also includes lenses associated with each source (2022, 2024, and 2026).

The combined light can be directed towards an x/y mirror 2016 that reflects all frequencies of light. The x/y mirror 2016 can direct the combined collinear light towards a target area on the measurement location 2040. The measurement location 2040 can include a photodetector 2042. The x/y mirror 2016 can be tilted to direct the beam along the surface of the tissue and change the area that is targeted.

One or more lenses 2030 can be adjusted such that the target depth at which is light beam is focused at a desired depth. In some examples, the lenses can be circular and adjusted by rotating a screw to move one or more lenses up or down to adjust the focal depth of the mirror.

Figure 22:
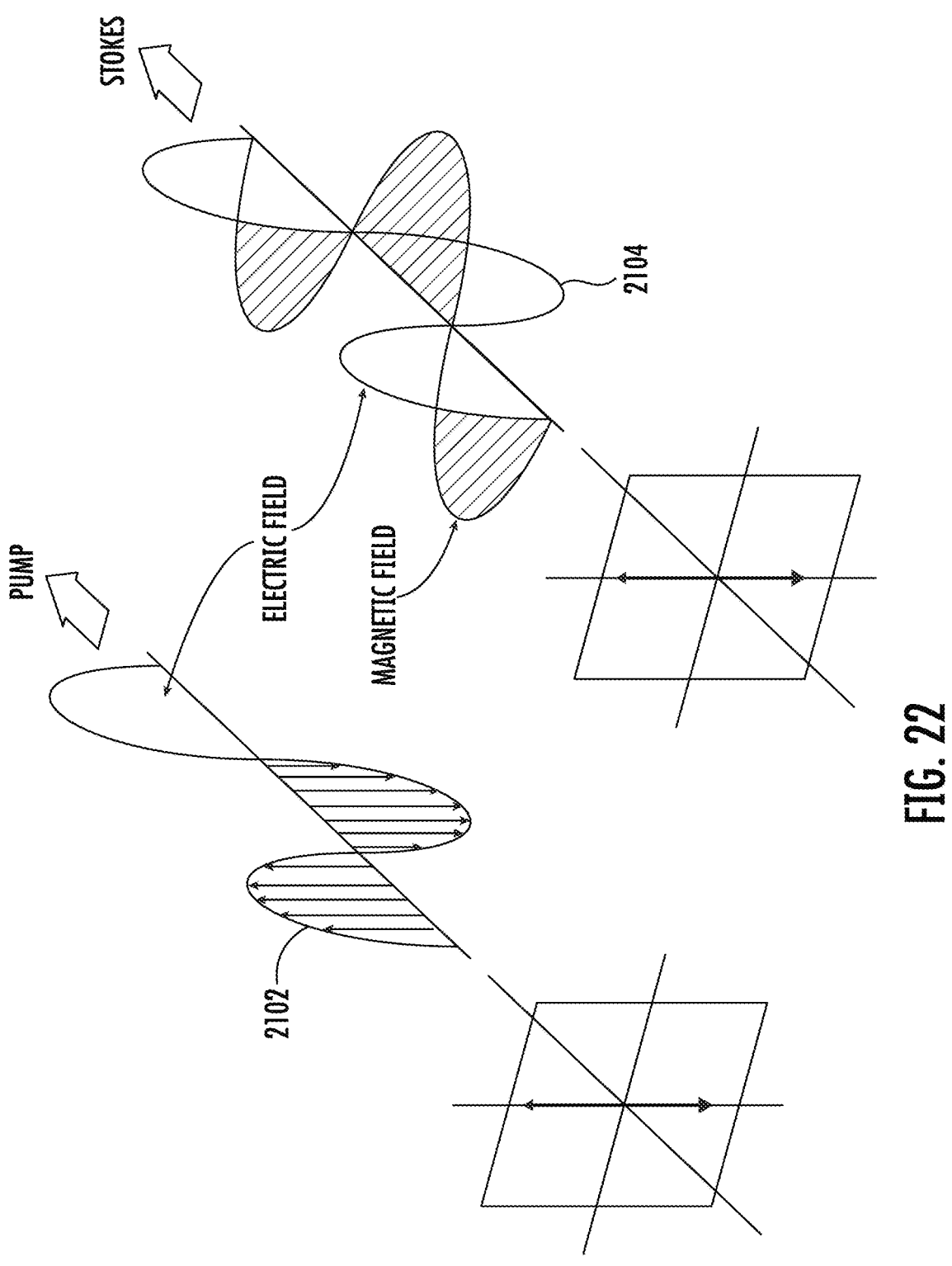
FIG. 22 is a graph illustrating the effect of parallel and orthogonal polarization in generated light in accordance with example embodiments of the present disclosure.

FIG. 22 is a diagram illustrating the effect of polarity in generated light in accordance with example embodiments of the present disclosure. In this example, the light 2102 produced by the pump source and the light 2104 produced by the one or more Stokes sources (both examples of electromagnetic radiation) are displayed with their respective component electric fields and magnetic field.

Figure 23:
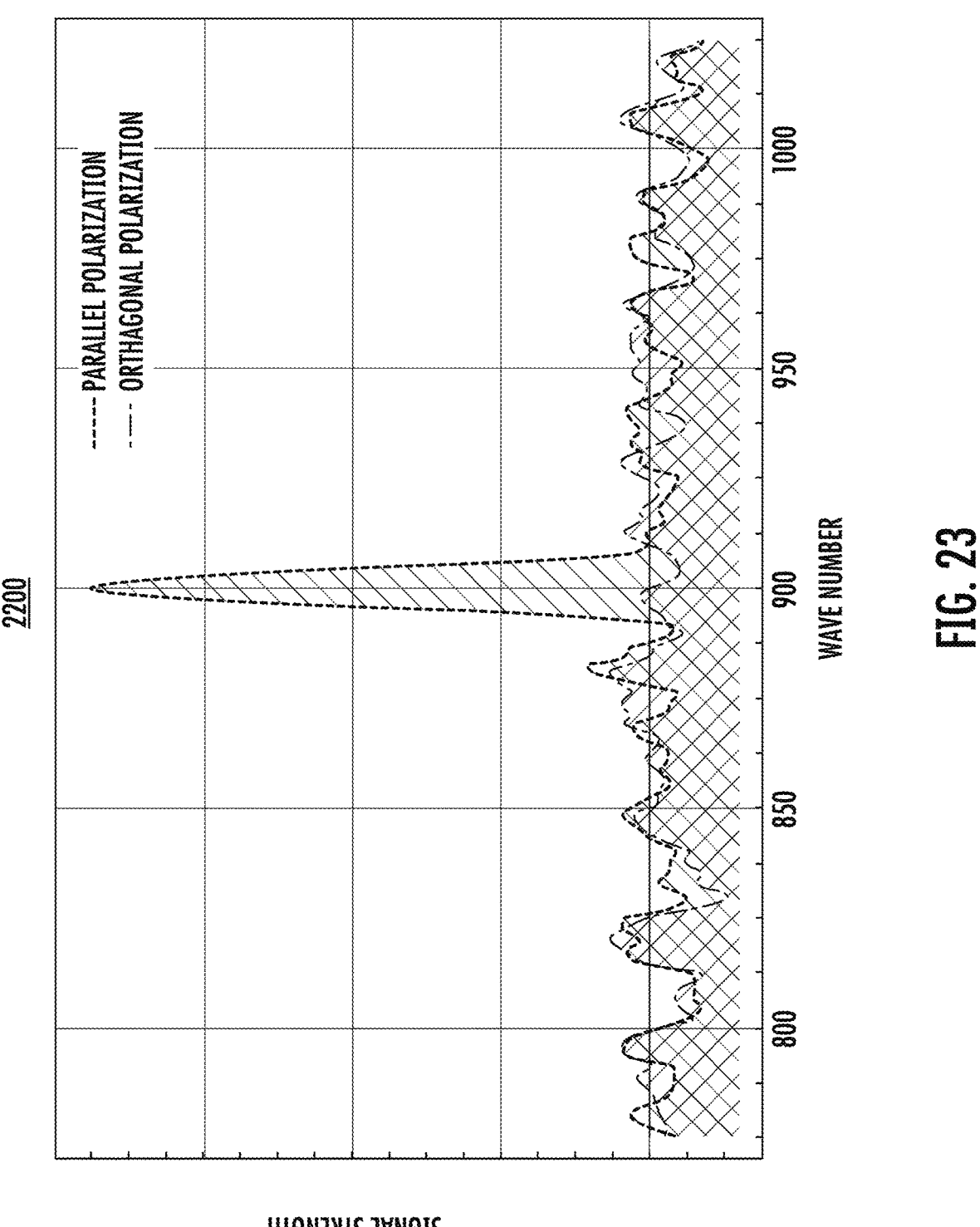
FIG. 23 includes two graphs illustrating light sources being pulsed in accordance with a specific duty cycle in accordance with example embodiments of the present disclosure.

FIG. 23 is a graph 2200 illustrating the effect of parallel and orthogonal polarization in generated light in accordance with example embodiments of the present disclosure. As can be seen in this graph, when the Stokes light and the Pump light have parallel polarization, the resulting power is significantly higher than the power resulting when the light has orthogonal polarization. Thus, the analyte estimation system can ensure the light produced by the Pump light source and the one or more Stokes light sources have a parallel polarization.

Figure 24:
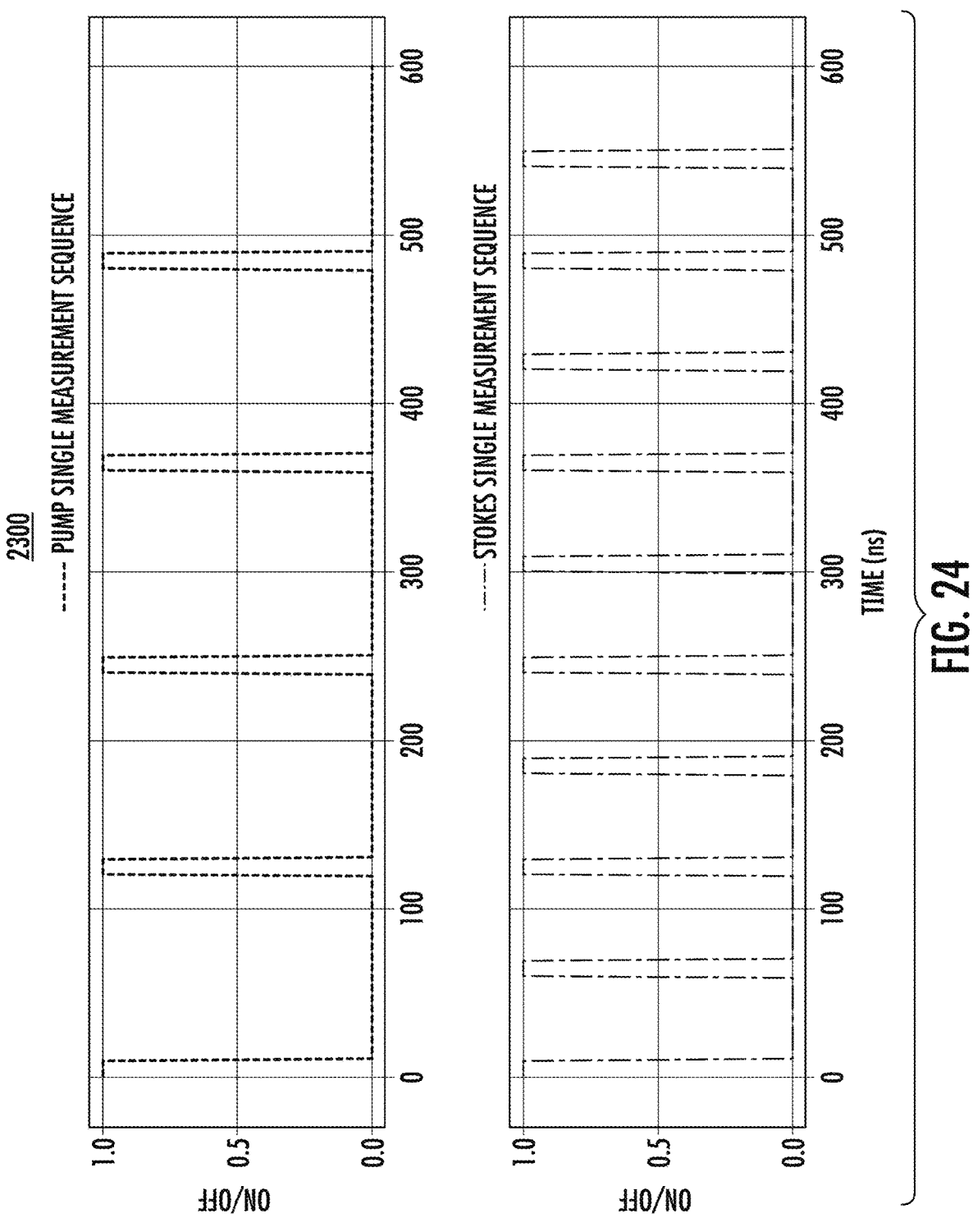
FIG. 24 is a flowchart depicting an example process of detecting analytes within a target tissue in accordance with example embodiments of the present disclosure.

FIG. 24 includes two graphs 2300 illustrating light sources being pulsed in accordance with a specific duty cycle in accordance with example embodiments of the present disclosure. In this example, the Pump source can be controlled in accordance with a first duty cycle and the one or more Stokes sources can be controlled in accordance with a second duty cycle. For example, the one or more Stokes sources can be operated at a duty cycle such that it is turned on twice as often as the Pump source. Importantly, whenever the pump source is pulsed, the one or more Stokes sources are also pulsed on.

FIG. 25 is a flowchart depicting an example process of detecting analytes within a target tissue in accordance with example embodiments of the present disclosure. One or more portion(s) of the method can be implemented by one or more computing devices such as, for example, the computing devices described herein. Moreover, one or more portion(s) of the method can be implemented as an algorithm on the hardware components of the device(s) described herein. FIG. 25 depicts elements performed in a particular order for purposes of illustration and discussion. Those of ordinary skill in the art, using the disclosures provided herein, will understand that the elements of any of the methods discussed herein can be adapted, rearranged, expanded, omitted, combined, and/or modified in various ways without deviating from the scope of the present disclosure. The method can be implemented by one or more computing devices, such as one or more of the computing devices depicted in FIG. 20.

A device for non-invasively measuring a level of an analyte in a user using Stimulated Raman Scattering can include a Raman pump source that, when engaged, emits, at 2402, pump light toward a skin surface of the user at a pump wavelength. The device can further include a Stokes source that, when engaged, emits, at 2404, Stokes light toward the skin surface at one or more Stokes wavelengths. The device can further include a photodetector that measures, at 2406, light that emanates from the skin surface.

In some examples, the Raman pump source and the Stokes source can be laser diodes. For example, the laser diodes can be vertical-cavity surface-emitting lasers (VCSELs). The Raman pump source and the Stokes source can be single-mode VCSELs. In another example, the laser diode can be an edge emitting diode laser. Thus, the Raman pump source and the Stokes sources can be light edge emitting diode lasers, VCSELs, or another type of laser diode. In some examples, both the Raman pump source and the Stokes source can be the same type of laser diode. In other examples, the Raman pump source and the Stokes source can be different The device can further include control circuitry that controls a Raman pump source and a Stokes source in accordance with at least one duty cycle associated with maximizing power associated with the light produced by the Raman pump source and the Stokes source while staying within predetermined exposure limits. The at least one duty cycle can engage the Raman pump source and the Stokes source for a first time period followed by a longer second time period in which the Raman pump source and the Stokes source are not engaged. The device can further include a processor that processes, at 2408, the measured light to provide an estimated analyte level of the analyte in the user.

In some examples, wherein the at least one duty cycle can direct the control circuitry to engage the Raman pump source and the Stokes source for less than one percent of the time in a particular period. More specifically, the at least one duty cycle can be a 0.1 percent duty cycle. In some examples, the light sources can be engaged for a period of 10 nanoseconds or less followed by a period of 990 nanoseconds or more in which the light sources are not engaged. In a specific example, the at least one particular duty cycle can engage the Raman pump source and the Stokes source for a 1 ns pulse duration followed by 999 ns in which the Raman pump source and the Stokes source are not engaged.

In some examples, the at least one duty cycle includes a first duty cycle and a second duty cycle. For example, the Raman pump source is pulse modulated in accordance with the first duty cycle and the Stokes source is pulse modulated in accordance with the second duty cycle. In examples in which the Raman pump sources is pulse modulated in accordance with a different duty cycle that the one or more Stokes sources, at least one Stokes source is engaged whenever the Pump source is engaged.

In some examples, the control circuitry can use pulse modulation to control the Raman pump source and the Stokes source. In some examples, a first pulse frequency can be associated with the Raman pump source and a second pulse frequency can be associated with one or more Stokes sources. In some examples, the first pulse frequency can be less that the second pulse frequency. For example, the first pulse frequency can be 5 MHz and the second pulse frequency can be 10 Mhz. In some examples, the second pulse frequency can be less than the second pulse frequency. In some examples, the control circuitry can control the Raman pump source and the Stokes source to produce pulsed signals in phase.

In some examples, the device can include a collimator to ensure the light emitted by the Raman pump source and the light emitted by the Stokes source are projected in parallel to the skin surface of the user. In some examples, one or more dichroic mirrors can combine the light from the Raman pump source and the Stokes source into a single light beam. The device can include focusing optics that focuses the single light beam onto particular area of the targeted sample (e.g., an area of the skin of a user with a diameter less than 10 microns. The focusing optics can include one or more lenses. In some examples, the device can include a wave guide rather than a dichroic mirrors. In some examples, the device can include both a wave guide and one or more dichroic mirrors.

The Raman pump light produced by the Raman Pump source and Stokes light produced by the Stokes source can be polarized. The light produced by the Raman pump source and the light produced by the Stokes source can be polarized in such that the light beams are parallel.

In some examples, the Raman pump source and the Stokes sources can be configured to project light onto an area with a diameter less than 10 microns. The Raman pump source and the Stokes source, while operated in pulsed mode, can be operated at a higher power level than is possible during continuous operation mode. In some examples, the predetermined exposure limits can be based on maximum permissible exposure for the Raman pump source and the Stokes source. In some examples, the Stokes light comprises a plurality of narrowband emissions at a plurality of respective center wavelengths within the window of Raman measurement wavelengths.

Figure 26:
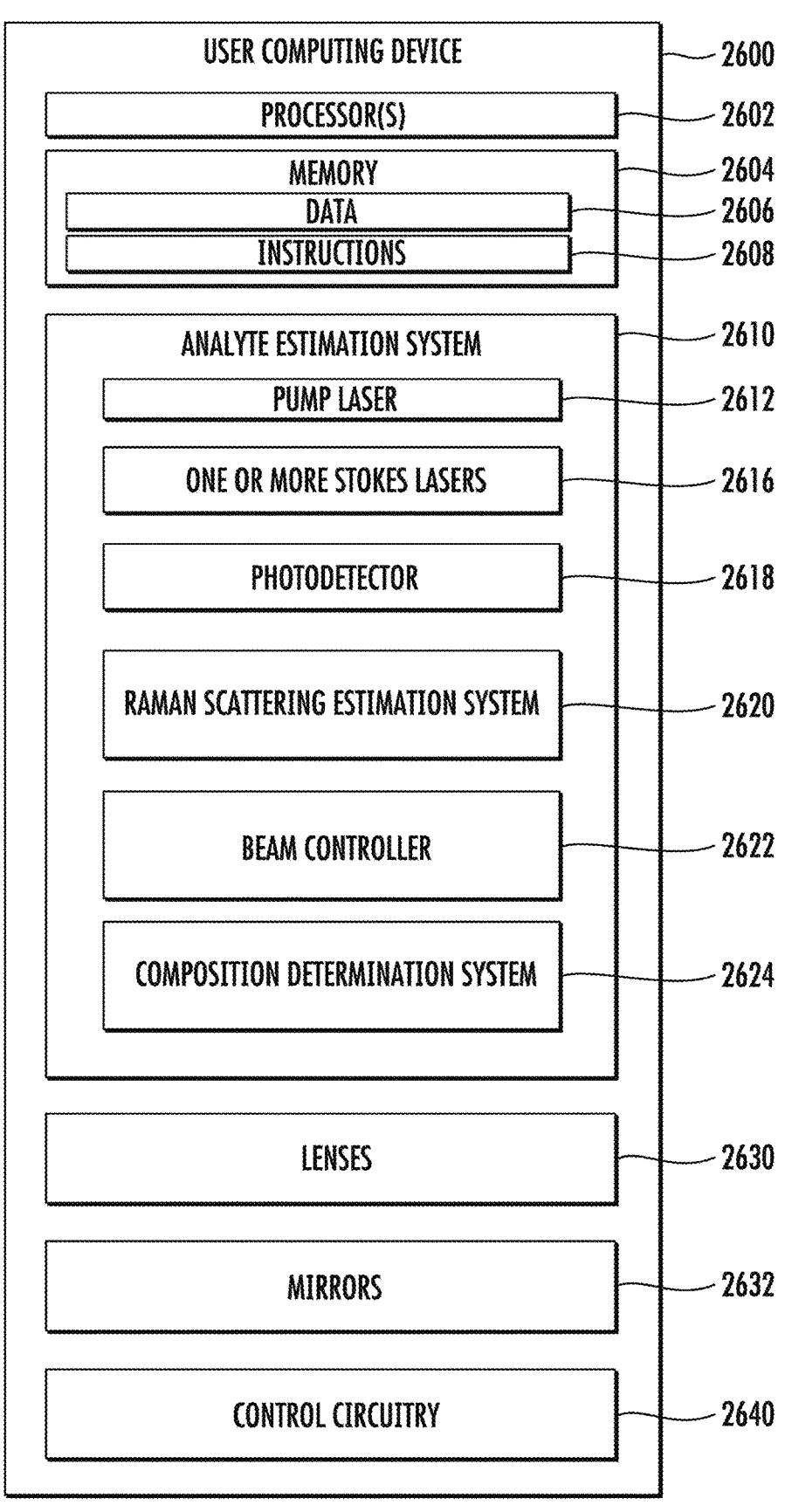
FIG. 26 illustrates an example computing environment including a user computing device 2600 in accordance with example embodiments of the present disclosure.

FIG. 26 illustrates an example computing environment including a user computing device 2600 in accordance with example embodiments of the present disclosure. The computing device 2600 can include an analyte estimation system 2610 for non-invasively determining the presence and amount of one or more analytes internal to a user. In some examples, the computing device 2600 can be a user computing device such as a smartphone or a wearable computing device. In other examples, the user computing device 2600 can be a computing device intended for home use and not for portability. In this example, the user computing device 2600 can include one or more processors 2602, memory 2604, an analyte estimation system 2610, one or more lenses 2630, one or more mirrors 2632, and control circuitry 2640.

In more detail, the one or more processors 2602 can be any suitable processing device for a computing device 2600. For example, such a processor can include one or more of: one or more processor cores, a microprocessor, an ASIC, an FPGA, a controller, a microcontroller, etc. The one or more processors can be one processor or a plurality of processors that are operatively connected. The memory 2604 can include one or more non-transitory computer-readable storage media, such as RAM, ROM, EEPROM, EPROM, flash memory devices, etc., and combinations thereof.

In particular, in some devices, memory 2604 can store instructions 2608 for implementing the analyte estimation system 2610. It will be appreciated that the term "system" can refer to specialized hardware, computer logic that executes on a more general processor, or some combination thereof. Thus, a system can be implemented in hardware, application-specific circuits, firmware, and/or software controlling a general-purpose processor. In one embodiment, the system can be implemented as program code files stored on the storage device, loaded into memory, and executed by a processor or can be provided from computer program products, for example, computer-executable instructions, that are stored in a tangible computer-readable storage medium such as RAM, hard disk or optical or magnetic media.

Memory 2604 can also include data 2606 that can be retrieved, manipulated, created, or stored by the one or more processor(s) 2602. In some example embodiments, such data can be accessed and used as input to the analyte estimation system 2610. In some examples, the memory 2604 can include data used to perform one or more processes and instructions that describe how those processes can be performed.

In some examples, the analyte estimation system 2610 can include a pump laser 2612 (also referred to as a Raman pump laser), one or more Stokes lasers 2616, a photodetector 2622, a Raman scattering estimation system 2620, a beam controller 2622, and a composition determination system 2624. The pump laser 2612 (e.g., a first light source) can be a laser diode that emits light (e.g., a stream of photons) at the target wavelength. In some examples, the pump laser can produce light with an average wavelength of 780 nanometers. Other wavelengths may be produced by the pump laser. The wavelengths of the one or more Stokes lasers 2616 can be determined based, at least in part, on the wavelength of the pump laser 2612. In some examples, the pump laser 2612 can be a vertical-cavity surface-emitting laser (VCSEL) included in a semiconductor chip. In some examples, the wavelength of the light emitted by the pump laser 2612 is 850 nanometers. Other wavelengths can be used.

The light produced by the pump laser 2612 can be directed by the beam controller 2622. The beam controller can 2622 control the one or more mirrors and the one or more lenses to ensure that the light emitted by the pump laser 2612 is directed towards the optimal target area and focused at the appropriate depth. The optimal target area can be determined by the composition determination system 2624.

The pump laser 2612 can include (or be associated with) a modulation system. The modulation system can, in coordination with the control circuitry, can be used to modulate the light produced by the pump laser 2612. The pump laser can be referred to as a first light source. By modulating the light produced by the pump laser 2612, the analyte estimation system 2610 can differentiate (e.g., using a filter or lock-in amplifier) between light that the target material emits after being excited by the light that originated from the pump laser 2612 and the light that the target material emits after being excited by the light that originates from the one or more Stokes lasers 2616.

The one or more Stokes lasers 2616 can include a tunable laser that can produce light with a wavelength within a predetermined range as needed. Thus, the tunable laser can be adjusted such that the wavelength of the light produced by the light source can change within a range. For example, the tunable laser can be adjusted to emit light with a wavelength that can vary from 910 nanometers to 980 nanometers. In some examples, the wavelength of the light produced by the tunable laser can be determined based on the Raman signature of a particular analyte that the analyte estimation system 2620 is trying to identify. In some examples, both the pump laser and the one or more Stokes lasers can use about 40 milliwatts of power to operate.

In some examples, the pump laser 2612 and the one or more Stokes lasers 2616 can be operated at more than one power level. For example, the lasers (e.g., the pump laser 2612 and the one or more Stokes lasers 2616) can have a lower power level used when determining the type of tissue found at one or more points within the user's tissue. The lasers (e.g., the pump laser 2612 and the one or more Stokes lasers 2616) can have a higher power level that is used when analyzing tissue to determine whether it contains a particular analyte and, if so, at what concentrations.

The light produced by the one or more Stokes lasers 2616 can be directed by a beam controller 2622. The beam controller can 2622 control the one or more mirrors 2632 and the one or more lenses 2630 to ensure that the light emitted by the one or more Stokes lasers 2616 is directed towards the optimal target area and focused at the appropriate depth. The optimal target area can be determined by the composition determination system 2624.

In some examples, the one or more Stokes lasers 2616 can include a modulation system. Thus, in some configurations, the pump laser 2612 can be modulated to distinguish the light produced by the pump laser 2612 from the light produced by the one or more Stokes lasers 2616. In other examples, the one or more Stokes lasers 2616 are modulated to distinguish between the two light sources.

In some examples, the one or more Stokes lasers 2616 can provide light with a wavelength tuned to the Raman signature of a particular analyte that the analyte estimation system 2620 is trying to identify (e.g., glucose). By providing additional light (e.g., a stream of photons) with a wavelength determined based on the Raman signature of the analyte, the analyte estimation system 2620 can enable stimulated Raman scattering to occur. Stimulated Raman scattering can result in the light provided by the one or more Stokes lasers 2616 stimulating more Raman scattering than would be expected without the additional light provided by the one more Stokes lasers 2616. Thus, introducing the light provided by the one or more Stokes lasers 2616 can increase the detectability of a particular analyte in the sample material because the probability of Raman scattering is increased.

In some examples, the analyte estimation system 2610 can include a photodetector 2618. The photodetector 2618 can be a sensor (e.g., a semiconductor device that converts light (e.g., photons) into electrical current) such as a photodiode. The photodiode can be configured to detect light over a range of wavelengths. In some example embodiments, light can be optically filtered such that only light within a specific wavelength range is detected by the photodetector. An amount of light can also be understood to be the number of photons detected and/or the intensity of the light measured at a particular wavelength.

In some examples, a filter can be employed to remove target-emitted light that is associated with the one or more Stokes lasers 2616 such that only light originating from the pump laser 2612 is detected. Similarly, an optical filter can filter out light with a wavelength associated with the pump laser 2612 such that only target-emitted light that results from the Stokes lasers 2616 or Raman scattering is detected by the photodetector. In some examples, a filter (or a lock-in amplifier) can remove modulated light, if the one or more Stokes lasers 2616 were modulated, or unmodulated light, if the pump laser 2612 was modulated.

The Raman scattering estimation system 2620 can be used to detect the amount of light (e.g., the intensity of the light or the number of photons) generated by Raman scattering associated with an analyte in the sample material. In some examples, the Raman scattering estimation system 2620 can determine the amount of light (e.g., either the number of photons or the intensity of the light) that has been Raman scattered to identify an analyte in the target material. In a first example, the user computing device can determine the amount of light at the pump wavelength (e.g., a first wavelength) that is lost (stimulated Raman loss). Alternatively, the user computing device can determine the amount of light at the Stokes associated wavelength that is gained (e.g., stimulated Raman gain). Either measurement or their combination can be used to estimate the amount of a particular analyte in the target material (e.g., a user's skin). A detected Stokes range can be compared to a reference spectrum to noninvasively measure the presence or absence of a target analyte.

For example, the sample material can be a portion of a user's body. The analyte can be, for example, glucose. Based on the amount of light having the predetermined second wavelength, the Raman scattering estimation system 2620 can estimate the amount of the analyte in the target sample. In some examples, the estimated amount of the analyte can be presented for display to a user.

In some examples, the user computing device 2600 can include a beam controller 2622. The beam controller can comprise a system capable of controlling the direction of the beams produced by the pump laser 2612 and the one or more Stokes lasers 2616. The beam controller 2622 can control the direction of the beam via the one or more lenses 2630 and the one or more mirrors 2632. Specifically, the one or more mirrors can be tilted to direct the beams along the surface of the target area. In this way, the direction of the beam can be modified in the x and y axes (length and height along a user's skin).

The one or more lenses 2630 can be adjusted to update the focal depth at which the beams are focused. Thus, the z-axis of the targeted location can be adjusted. in this way, the beam controller can adjust the target location of the beans to target any location within a three-dimensional space accessible to the analyte detection system 2610. For example, if the user computing device 2600 is a wearable device that is held against the user's skin by a band or other means, the three-dimensional location which is accessible to the analyte detection system 2610 can be approximately equal to the area of skin underneath the device with a width approximately equal to the width of the analyte detection system 2610 and a depth associated with the maximum focus depth of the analyte detection system 2610. This maximum focus depth can be based on the degree to which the lenses can be adjusted and the characteristics of the tissue itself. In this way, the being controller in 2622 can enable the analyte detection system 2610 to target the optimal target location within the user's tissue wherever it may occur.

The user computing device 2600 can include a composition determination system 2624. The composition determination system 2624 can determine the type of tissue at a plurality of locations within an area of interest. The area of interest can be determined based on the range of the user's tissue that can be targeted by the beam controller. To determine the type of tissue throughout the area of interest, the composition determination system 2624 can generate a target sampling grid. The sampling can include a plurality of points to be sampled by the composition determination system 2624.

Once the target sampling grid has been established, the composition determination system 2624 can, for each point in the target sampling grid, project light at that point. The projected light can be from the pump laser 2612 and/or the one or more Stokes lasers 2616. The amount and duration of the emitted light can be lower than is projected when attempting to detect analytes through Raman scattering because detecting the type of tissue is possible based on the absorption of the skin without needing the high-power density used to induce Raman Scattering at a detectable level. Once the lower level of light has been projected at a respective point within the target sampling grid, the composition determination system 2624 can analyze the absorption of light by the respective point. By determining which wavelengths of light are absorbed by the material at that target point, the composition determination system 2624 can estimate the type of the material at that point. For example, different types of tissue will absorb different wavelengths of light. The type of tissue can be one or more of: interstitial fluid, cells associated with the epidermis, cells associate with the dermis, fat cells, glands, nerve cells, blood vessels, follicles, and so on.

Once the composition determination system 2624 has analyzed each point within the target sampling grid, the composition determination system 2624 can determine the optimal target location. In some examples, the optimal target location can be based on the specific type of tissue at the location. In other examples, the optimal target location can be based on the analyte to be detected.

In some examples, the user computing device 2600 comprises one or more lenses 2630. The one or more lenses can focus the light beams at different depths. The depth at which the beam(s) are focused can be adjusted by moving the lenses up or down. In some examples, the focus depth of the lens(es) 2630 are moved by being attached to a rotatable screw that can adjust the lens up or down without affecting any other aspect of the light beam because the lens is circular.

The user computing device 2600 can include one or more mirrors 2632. The one or more mirrors 2632 can be configured such that light is directed towards a particular portion of the target tissue. In some examples, the one or more mirrors 2632 can be tilted to such that it is targeted location The user computing device 2600 can include control circuitry 2640. The control circuitry 2640 can be used to increase the amount of light projected into the area of the target tissue (e.g., the power density of the light). In some examples, the control circuitry 2640 can reduce the intensity of light when determining the type of tissue at particular locations.

Figure 27:
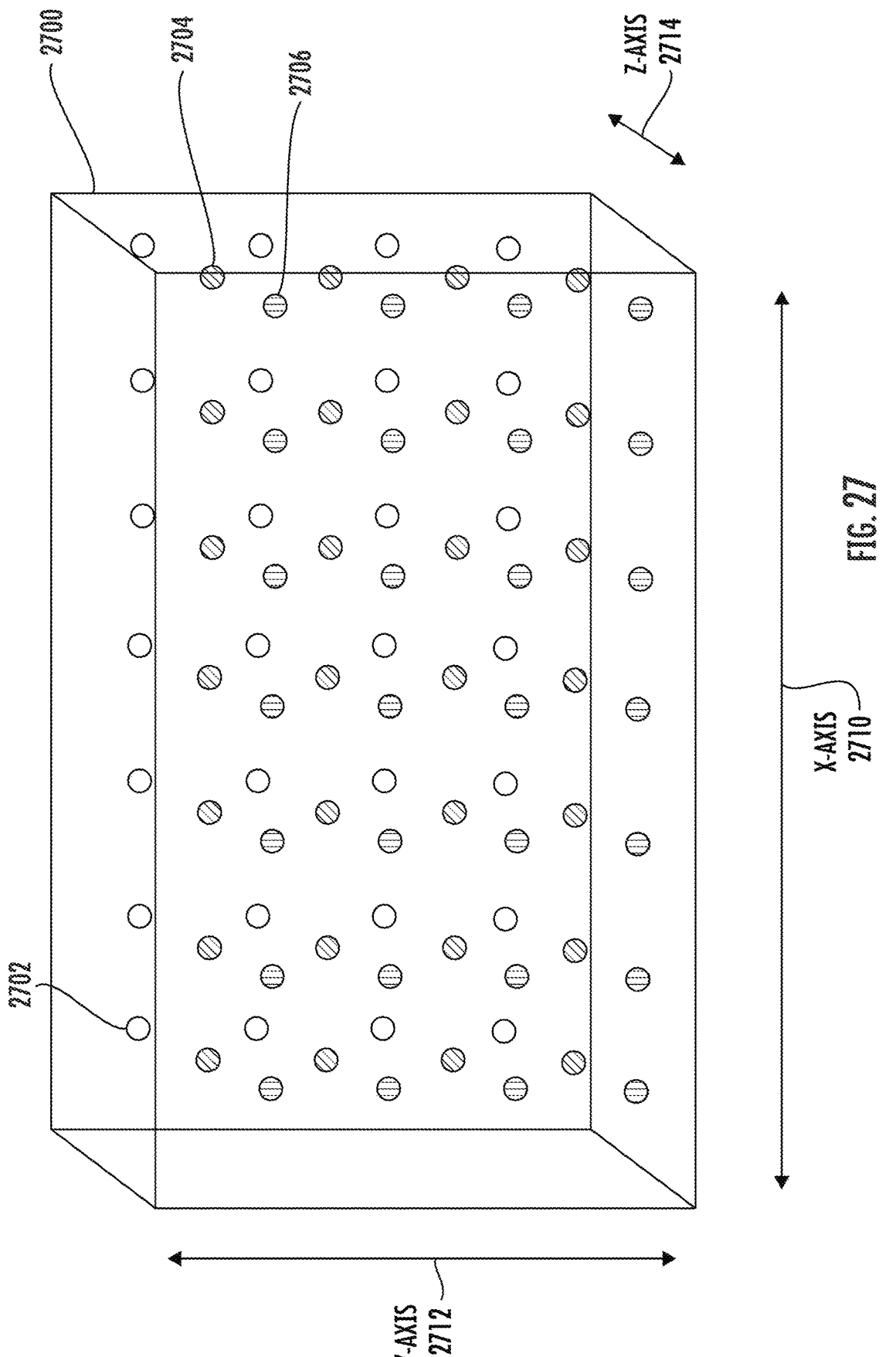
FIG. 27 is a diagram illustrating a target sampling grid in accordance with example embodiments of the present disclosure.

FIG. 27 is a diagram illustrating a sampling using a target sampling grid 2700. The area associated with the target sampling grid 2700 is determined based on the characteristics of the analyte detecting system. Specifically, the dimensions of the target sampling grid 2700 represent the area that it is possible to be targeted by the analyte detection system. Thus, the x-axis 2710 and the y-axis 2712 are determined based on the degree to which the one or more mirrors can adjust the light beams along the surface of the user's skin. The z-axis 2714 depth represents the depth that is possible to be targeted by adjusting the one or more lenses. In some examples, the depth to which the laser can penetrate the tissue can be determined, at least in part, based on the makeup of that tissue.

The target sampling grid 2700 can include a plurality of points (e.g., 2702, 2704, and 2706) that are targeted to be analyzed. The targets can be spaced out in three-dimensional space. Thus, some of the target points are deeper in the target tissue than others. In this example, the target points can be arranged in three layers of depth. Layer 1 (the deepest layer) is denoted by black dots and includes point 2702. Layer 2 (the middle layer) is denoted by right slanted lines and includes point 2704. Layer 3 (the uppermost layer) is denoted by vertical lines and includes point 2706. By orienting the potential target points at different layers of depth, the analyte estimation system can determine the type of tissue that makes up the entire section of the user's tissue.

FIG. 28 is a flowchart depicting an example process of detecting analytes within a target tissue in accordance with example embodiments of the present disclosure. One or more portion(s) of the method can be implemented by one or more computing devices such as, for example, the computing devices described herein. Moreover, one or more portion(s) of the method can be implemented as an algorithm on the hardware components of the device(s) described herein. FIG. 28 depicts elements performed in a particular order for purposes of illustration and discussion. Those of ordinary skill in the art, using the disclosures provided herein, will understand that the elements of any of the methods discussed herein can be adapted, rearranged, expanded, omitted, combined, and/or modified in various ways without deviating from the scope of the present disclosure. The method can be implemented by one or more computing devices, such as one or more of the computing devices depicted in FIG. 26.

A device for non-invasively measuring a level of an analyte in a user using Stimulated Raman Scattering can include a Raman pump source that emits, at 2802, pump light toward a skin surface of the user at a pump wavelength. The device can further include a Stokes source that emits, at 2804, Stokes light toward the skin surface at one or more Stokes wavelengths. The device can further comprise one or more mirrors that are controlled to determine an area of the skin surface at which the pump light and the Stokes light are targeted. The mirrors can be controlled to tilt the one or more mirrors. Each mirror can be tilted independently. In other examples, the mirrors may be connected such that the tilt of one mirror is dependent on that of one or more other mirrors. Tilting the mirrors can result in changing the location at which the light projected by the Stokes source and the Raman pump laser is targeted.

In some examples, the Raman pump source and the Stokes source can be laser diodes. For example, the laser diodes can be vertical-cavity surface-emitting lasers (VCSELs). The Raman pump source and the Stokes source can be single-mode VCSELs. In another example, the laser diode can be an edge-emitting diode laser. Thus, the Raman pump source and the Stokes sources can be light edge-emitting diode lasers, VCSELs, or another type of laser diode. In some examples, both the Raman pump source and the Stokes source can be the same type of laser diode. In other examples, the Raman pump source and the Stokes source can be different types of laser diodes.

In some examples, the device includes one or more lenses that are controlled to determine a focus depth of the Raman pump source and the Stokes source within the skin of a user. The one or more lenses can be moved up and down (relative to the device and/or relative to each other). For example, the one or more lenses can be attached or otherwise connected to a screw that can be rotated to adjust the position of the lenses. As long as the lenses are circular, the rotation of the screw may not alter any characteristics of the projected light other than the focus depth.

The device includes a beam controller that controls, at 2806, the one or more mirrors and the one or more lenses to target the pump light emitted by the Raman pump source and the Stokes light emitted by the Stokes source at an optimal target location. To do so, the beam controllers can control the tilt of one or more mirrors and the focus depth of the one or more lenses.

The device can further include a photodetector that measures, at 2808, light that emanates from the skin surface. In some examples, the device can include a collimator to ensure the light emitted by the Raman pump source and the light emitted by the Stokes source are projected in parallel to the skin surface of the user. In some examples, one or more dichroic mirrors can combine the light from the Raman pump source and the Stokes source into a single light beam. The device can include focusing optics that focus the single light beam onto a particular area of the targeted sample (e.g., an area of the skin of a user with a diameter less than 10 microns. The focusing optics can include one or more lenses. In some examples, the device can include a wave guide rather than a dichroic mirrors. In some examples, the device can include both a wave guide and one or more dichroic mirrors.

In some examples, the Raman pump source and the Stokes sources can be configured to project light onto an area with a diameter of less than 10 microns. In some examples, the area onto which the light is projected is 1 micron in diameter.

The device can include a target analysis system that identifies an optimal target location in the tissue of the user for measuring an analyte. Identifying the optimal target location in the tissue of the user can comprise generating a target sampling grid, the target sampling grid includes a plurality of potential target points within an area of the tissue able to be targeted by the beam controller. In some examples, the points in the target sampling grid are arranged in a three-dimensional array. Thus, the target sampling grid includes points at different depths within a three-dimensional space within the tissue.

In some examples, for a respective point in the plurality of potential target points, the device targets, using the beam controller, one or more light sources at the respective point. One or more of the light sources are initiated at a lower power. The lower power can be defined as being lower than the power at which the light sources are set when detecting analytes. The device can determine one or more frequencies absorbed by the respective point. The frequencies which are absorbed can be determined based on a comparison of the frequencies of light projected by the one or more light sources to the frequencies of light detected by the photodetectors. The one or more light sources include one or more of the Raman pump sources and the Stokes source.

In some examples, the frequencies of light selected to be projected can be determined based on the one or more particular tissue types. For example, the device can select one or more frequencies most useful to distinguish between two or more tissue types most likely to be found at the current target location. If the device determines (based on past measurements of the type of tissue from nearby measurements) that the two most likely tissue types are an artery and interstitial fluid, the device can select one or more frequencies that are most useful in distinguishing between these two tissue types. In this way, the device can minimize the number of frequencies used to detect the type of tissues.

Once the device determines one or more frequencies absorbed by a respective target point, the device can determine a type of tissue at the target point. In some examples, the device can determine that the type of tissue at the target point can be one of: a blood vessel, interstitial space, nerve tissue, hair or hair follicles, and so on.

Once the type of tissue has been determined for each of the target points, the device can rank the one or more potential target points based, at least in part, on the type of tissue associated with each of the one or more potential target points. The device can select an optimal target point from the one or more potential target points based on the ranking. In some examples, the one or more potential target points are ranked based, at least in part, on the analyte being detected. For example, certain analytes are more easily detected in different types of tissue. Thus, the device can select an optimal target point in a location with a type of tissue that is useful for detecting the current target analyte.

The technology discussed herein refers to servers, databases, software applications, and other computer-based systems, as well as actions taken and information sent to and from such systems. One of ordinary skill in the art will recognize that the inherent flexibility of computer-based systems allows for a great variety of possible configurations, combinations, and divisions of tasks and functionality between and among components. For instance, server processes discussed herein may be implemented using a single server or multiple servers working in combination. Databases and applications may be implemented on a single system or distributed across multiple systems. Distributed components may operate sequentially or in parallel.

While the present subject matter has been described in detail with respect to specific example embodiments thereof, it will be appreciated that those skilled in the art, upon attaining an understanding of the foregoing may readily produce alterations to, variations of, and equivalents to such embodiments. Accordingly, the scope of the present disclosure is by way of example rather than by way of limitation, and the subject disclosure does not preclude inclusion of such modifications, variations and/or additions to the present subject matter as would be readily apparent to one of ordinary skill in the art.

What is claimed is:

1. A device for non-invasively measuring a level of an analyte in a user using Stimulated Raman Scattering, comprising:
   a Raman pump source that emits pump light toward a tissue of the user at a pump wavelength;
   a Stokes source that emits Stokes light toward the tissue at one or more Stokes wavelengths;
   one or more mirrors;
   one or more lenses;
   a beam controller that controls the one or more mirrors and the one or more lenses to target the pump light emitted by the Raman pump source and the Stokes light emitted by the Stokes source at an optimal target location;
   a photodetector that measures light that emanates from the tissue;
   a processor that processes the measured light to provide an estimated analyte level of the analyte in the user; and
   a target analysis system that identifies an optimal target location in the tissue of the user for measuring an analyte, wherein identifying the optimal target location in the tissue of the user comprises:
      generating a target sampling grid, the target sampling grid including a plurality of potential target points within an area of the tissue able to be targeted by the beam controller;
      for a respective point in the plurality of potential target points, determining, based on information light that emanates from the tissue at the respective point, a type of tissue at the respective point; and
      determining, based on the type of tissue at each of the plurality of potential target points, an optimal target location.

2. The device of claim 1, wherein determining, based on information light that emanates from the tissue at the respective point, the type of tissue at the respective point further comprises:
   for a respective point in the plurality of potential target points:
      targeting, by the beam controller, one or more light sources at the respective point;
      initiating the one or more light sources at a lower power; and
      determining one or more frequencies absorbed by the respective point.

3. The device of claim 2, wherein the one or more light sources includes one or more of the Raman pump source and the Stokes source.

4. The device of claim 2, further comprising:
   determining, based on the one or more frequencies absorbed by the respective point, the type of tissue at the target point.

5. The device of claim 3, further comprising:

ranking one or more potential target points based, at least in part, on a type of tissue associated with each of the one or more potential target points; and selecting an optimal target point from the one or more potential target points based on the ranking.

6. The device of claim 5, wherein the one or more potential target points are ranked based, at least in part, on the analyte being detected.

7. The device of claim 1, wherein the points in the target sampling grid are arranged in a three-dimensional array.

8. The device of claim 1, wherein the one or more lenses are adjusted by moving them up and down to adjust a focal depth.

9. The device of claim 1, wherein the one or more mirrors are adjusted by tilting a mirror to direct the pump light and the Stokes light to a specific target on a surface of the tissue of a user.

10. The device of claim 1, wherein the Raman pump source and the Stokes source are VCSELs.

11. The device of claim 1, wherein the Raman pump source and the Stokes source are single-mode VCSELs.

12. The device of claim 1, wherein the Raman pump source and the Stokes source are edge emitting diode lasers.

13. The device of claim 1, wherein the Stokes light comprises a plurality of narrowband emissions at a plurality of respective center wavelengths within a window of Raman measurement wavelengths.

14. The device of claim 1, wherein the beam controller controls the one or more lenses to adjust a focal depth of the pump light emitted by the Raman pump source and the Stokes light emitted by the Stokes source.

15. The device of claim 1, wherein the beam controller controls the one or more mirrors to point on a surface of the tissue at which the pump light emitted by the Raman pump source and the Stokes light emitted by the Stokes source is targeted.

16. A computer-implemented method for non-invasively measuring a level of an analyte in a user using Stimulated Raman Scattering, comprising:

emitting, by a Raman pump source, pump light toward a tissue of the user at a pump wavelength;

emitting, by a Stokes source, Stokes light toward the tissue at one or more Stokes wavelengths;

determining an optimal target location in the tissue of the user for measuring an analyte, wherein determining the optimal target location in the tissue of the user comprises:

generating a target sampling grid, the target sampling grid including a plurality of potential target points within an area of the tissue able to be targeted by the beam controller;

for a respective point in the plurality of potential target points, determining, based on information light that emanates from the tissue at the respective point, a type of tissue at the respective point; and selecting, based on the type of tissue at each of the plurality of potential target points, an optimal target location;

controlling, by a beam controller, one or more mirrors and one or more lenses to target the pump light emitted by the Raman pump source and the Stokes light emitted by the Stokes source at an optimal target location;

measuring, by a photodetector, light that emanates from the tissue; and processing, by a processor, the measured light to provide an estimated analyte level of the analyte in the user.

17. An analyte estimation system for non-invasively measuring a level of an analyte in a user using Stimulated Raman Scattering, the device comprising:

a Raman pump source that emits pump light toward a tissue of the user at a pump wavelength;

a Stokes source that emits Stokes light toward the tissue at one or more Stokes wavelengths;

one or more mirrors;

one or more lenses;

a beam controller that controls the one or more mirrors and the one or more lenses to target the pump light emitted by the Raman pump source and the Stokes light emitted by the Stokes source at an optimal target location;

a photodetector that measures light that emanates from the tissue;

a processor that processes the measured light to provide an estimated analyte level of the analyte in the user; and a target analysis system that identifies an optimal target location in the tissue of the user for measuring an analyte, wherein identifying the optimal target location in the tissue of the user comprises:

generating a target sampling grid, the target sampling grid including a plurality of potential target points within an area of the tissue able to be targeted by the beam controller;

for a respective point in the plurality of potential target points, determining, based on information light that emanates from the tissue at the respective point, a type of tissue at the respective point; and determining, based on the type of tissue at each of the plurality of potential target points, an optimal target location.

* * * * *